(12) United States Patent
Parham et al.

(10) Patent No.: US 11,535,619 B2
(45) Date of Patent: Dec. 27, 2022

(54) HEXACYCLIC HETEROAROMATIC COMPOUNDS FOR ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Dominik Joosten, Ober-Ramstadt (DE); Aurélie Ludemann, Frankfurt am Main (DE); Tobias Grossmann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 255 days.

(21) Appl. No.: 16/615,267

(22) PCT Filed: May 18, 2018

(86) PCT No.: PCT/EP2018/063031
§ 371 (c)(1),
(2) Date: Nov. 20, 2019

(87) PCT Pub. No.: WO2018/215318
PCT Pub. Date: Nov. 29, 2018

(65) Prior Publication Data
US 2020/0165252 A1    May 28, 2020

(30) Foreign Application Priority Data

May 22, 2017 (EP) .................................... 17172234

(51) Int. Cl.
| | | |
|---|---|---|
| *C07D 471/22* | (2006.01) |
| *C07D 471/16* | (2006.01) |
| *C07D 403/04* | (2006.01) |
| *H01L 51/00* | (2006.01) |

(52) U.S. Cl.
CPC ......... *C07D 471/22* (2013.01); *C07D 403/04* (2013.01); *C07D 471/16* (2013.01); *H01L 51/0067* (2013.01); *H01L 51/0072* (2013.01); *H01L 51/0073* (2013.01)

(58) Field of Classification Search
None
See application file for complete search history.

(56) References Cited

FOREIGN PATENT DOCUMENTS

| KR | 20180032347 A | 3/2018 |
|---|---|---|
| WO | WO-2005048315 A2 | 5/2005 |
| WO | WO-2013183327 A1 | 12/2013 |

OTHER PUBLICATIONS

Internatioanl Search Report for PCT/EP2018/063031 dated Jul. 5, 2018.
Mitsumori, T., et al., "Synthesis and Properties of Highly Fluorescent Indolizino[3,4,5-ab]isoindoles", Journal of the American Chemical Society, vol. 126, No. 51, (2004), pp. 16793-16803.
Mitsumori, T., et al., "Synthesis, properes, and LED performance of highly luminescent metal complexes containing indoiizino[3,4,5-ab]isoindoles", Journal of Materials Chemistry, vol. 19, No. 32, (2009), pp. 5826-5836.
Shen, Y.-M., et al., "Synthesis and Emitting Properties of the Blue-Light Fluorophores Indolizino[3,4,5-ab]isoindole Derivatives", European Journal of Organic Chemistry, vol. 2007, No. 22, (2007), pp. 3718-3726.
Written Opinion of the International Search Report for PCT/EP2018/063031 dated Jul. 5, 2018.

*Primary Examiner* — Jay Yang
(74) *Attorney, Agent, or Firm* — Faegre Drinker Biddle & Reath LLP

(57) ABSTRACT

The invention relates to heteroaromatic compounds, particularly for use in electronic devices. The invention further relates to a method for producing the compounds according to the invention and to electronic devices containing same.

19 Claims, No Drawings

HEXACYCLIC HETEROAROMATIC COMPOUNDS FOR ELECTRONIC DEVICES

CROSS-REFERENCE TO RELATED APPLICATIONS

This application is a national stage application (under 35 U.S.C. § 371) of PCT/EP2018/063031, filed May 18, 2018, which claims benefit of European Application No. 17172234.1, filed May 22, 2017, both of which are incorporated herein by reference in their entirety.

The present invention relates to heteroaromatic compounds, especially for use in electronic devices. The invention further relates to a process for preparing the compounds of the invention and to electronic devices comprising these compounds.

Emitting materials used in organic electroluminescent devices (OLEDs) are frequently organometallic complexes which exhibit phosphorescence.

For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of organic electroluminescent devices are not only determined by the emitters used. Also of particular significance here are especially the other materials used, such as host/matrix materials, hole blocker materials, electron transport materials, hole transport materials and electron or exciton blocker materials. Improvements to these materials can lead to distinct improvements to electroluminescent devices.

According to the prior art, indolizine derivatives are among the matrix materials used for phosphorescent compounds. For example, J. Am. Chem. Soc. Vol, 126, No. 51, 2004, 16793-16803, J. Mater. Chem., 2009, 19, 5826-5836, Eur. J. Org. Chem. 2007, 3718-3726, WO 2013/183327 and WO 2005/048315 describe corresponding compounds. However, the indolizine derivatives described do not have a further ring structure fused to the five-membered ring of the indolizine structure.

In general terms, in the case of these materials, for example for use as matrix materials, hole conductor materials or electron transport materials, there is still a need for improvement, particularly in relation to the lifetime, but also in relation to the efficiency and operating voltage of the device. Moreover, the compounds should have high color purity.

The problem addressed by the present invention is therefore that of providing compounds which are suitable for use in an organic electronic device, especially in an organic electroluminescent device, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials, the hole conductor materials or the electron transport materials too have an essential influence on the lifetime and efficiency of the organic electroluminescent device.

A further problem addressed by the present invention can be considered that of providing compounds suitable for use in a phosphorescent or fluorescent OLED, especially as a matrix material. A particular problem addressed by the present invention is that of providing matrix materials suitable for red-, yellow- and green-phosphorescing OLEDs, especially as matrix material for a red-phosphorescing compound.

In addition, the compounds, especially when they are used as matrix materials, as hole conductor materials or as electron transport materials in organic electroluminescent devices, should lead to devices having excellent color purity.

Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality. Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. The present invention therefore provides electronic devices, especially organic electroluminescent devices, containing such compounds, and the corresponding preferred embodiments.

The present invention therefore provides a compound comprising at least one structure of the following formula (I):

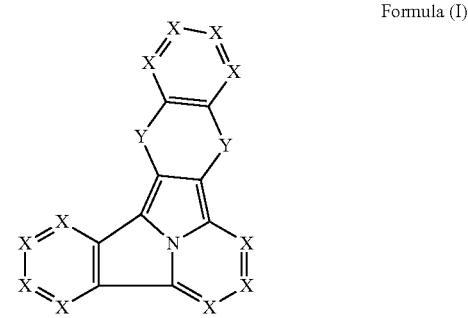

Formula (I)

where the symbols used are as follows:

Y is the same or different at each instance and is a bond or $NR^1$, NAr, O, S, $C(R^1)_2$, $CArR^1$, $C(Ar)_2$, $Si(Ar)_2$, $SiArR^1$ or $Si(R^1)_2$, where at least one Y group is selected from $NR^1$, NAr, O, S, $C(R^1)_2$, $CArR^1$, $C(Ar)_2$, $Si(Ar)_2$, $SiArR^1$ or $Si(R^1)_2$, preferably from $NR^1$ or NAr, more preferably NAr;

X is the same or different at each instance and is N or $CR^1$, preferably $CR^1$;

Ar is the same or different at each instance and is an aromatic or heteroaromatic ring system which has 5 to 60 aromatic ring atoms and may be substituted by one or more $R^1$ radicals; at the same time, two Ar radicals bonded to the same carbon atom or silicon atom may also be joined to one another by a single bond or a bridge selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$ and P(=O)$R^1$;

R¹ is the same or different at each instance and is H, D, OH, OR², F, Cl, Br, I, CN, NO₂, N(Ar¹)₂, N(R²)₂, C(=O)Ar¹, C(=O)R², P(=O)(Ar¹)₂, P(Ar¹)₂, B(Ar¹)₂, B(OR²)₂, Si(Ar¹)₃, Si(R²)₃, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more R² radicals, where one or more nonadjacent CH₂ groups may be replaced by —R²C=CR²—, —C≡C—, Si(R²)₂, Ge(R²)₂, Sn(R²)₂, C=O, C=S, C=Se, C=NR², —C(=O)O—, —C(=O)NR²—, NR², P(=O) (R²), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R² radicals, or an aryloxy or heteroaryloxy group which has 5 to 40 aromatic ring atoms and may be substituted by one or more R² radicals, or an aralkyl or heteroaralkyl group which has 5 to 40 aromatic ring atoms and may be substituted by one or more R² radicals, or a combination of these systems; at the same time, two or more preferably adjacent R¹ radicals may form a ring system with one another;

Ar¹ is the same or different at each instance and is an aromatic or heteroaromatic ring system which has 5 to 30 aromatic ring atoms and may be substituted by one or more nonaromatic R² radicals; at the same time, it is possible for two Ar¹ radicals bonded to the same silicon atom, nitrogen atom, phosphorus atom or boron atom also to be joined to one another by a single bond or a bridge selected from B(R²), C(R²)₂, Si(R²)₂, C=O, C=NR², C=C(R²)₂, O, S, S=O, SO₂, N(R²), P(R²) and P(=O) R²;

R² is the same or different at each instance and is H, D, F, Cl, Br, I, CN, B(OR³)₂, NO₂, C(=O)R³, CR³=C(R³)₂, C(=O)OR³, C(=O)N(R³)₂, Si(R³)₃, P(R³)₂, B(R³)₂, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, Ge(R³)₂, Sn(R³)₂, C=O, C=S, C=NR³, —C(=O)O—, —C(=O)NR³—, NR³, P(=O)(R³), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R³ radicals, or an aryloxy or heteroaryloxy group which has 5 to 40 aromatic ring atoms and may be substituted by one or more R³ radicals, or a combination of these systems; at the same time, two or more preferably adjacent R² substituents may also form a ring system with one another;

R³ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be substituted by D, F, Cl, Br, I or CN and which may be substituted by one or more alkyl groups each having 1 to 4 carbon atoms; at the same time, it is also possible for two or more, preferably adjacent R³ substituents to form a ring system with one another.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, should be understood to mean, inter alia, that the two radicals are joined to one another by a chemical bond with formal elimination of two hydrogen atoms. This is illustrated by the following scheme:

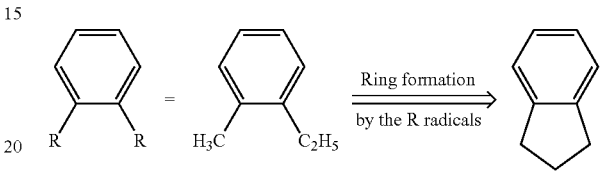

In addition, however, the abovementioned wording should also be understood to mean that, if one of the two radicals is hydrogen, the second radical binds to the position to which the hydrogen atom was bonded, forming a ring. This shall be illustrated by the following scheme:

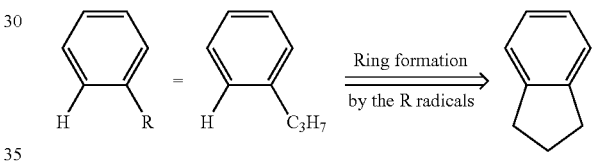

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

An aryl group in the context of this invention contains 6 to 60 carbon atoms, preferably 6 to 40 carbon atoms, more preferably 6 to 30 carbon atoms; a heteroaryl group in the context of this invention contains 2 to 60 carbon atoms, preferably 2 to 40 carbon atoms, more preferably 2 to 30 carbon atoms, and at least one heteroatom, with the proviso that the sum total of carbon atoms and heteroatoms is at least 5. The heteroatoms are preferably selected from N, O and/or S. Here, an aryl group or heteroaryl group is understood to mean either a simple aromatic ring, i.e. benzene, or a simple heteroaromatic ring, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms, preferably 6 to 40 carbon atoms, more preferably 6 to 30 carbon atoms, in the ring system. A heteroaromatic ring system in the context of this invention contains 1 to 60 carbon atoms, preferably 1 to 40 carbon atoms, more preferably 1 to 30 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5 to 60, preferably 5-40, aromatic ring atoms, more preferably 5 to 30 aromatic ring atoms, and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the present invention, one of the Y groups in formula (I) represents NAr or $NR^1$ and one of the Y groups represents O, S or $C(R^1)_2$. In a further embodiment, one of the Y groups in formula (I) represents NAr or $NR^1$ and one of the Y groups represents a bond, with preference for the embodiment in which one of the Y groups represents a bond over the embodiment in which both Y groups are selected from $NR^1$, NAr, O, S, $C(R^1)_2$, $CArR^1$, $C(Ar)_2$, $Si(Ar)_2$, $SiArR^1$ and $Si(R^1)_2$.

In a preferred configuration, the compounds of the invention may comprise at least one structure of the formula (IIa) or (IIb)

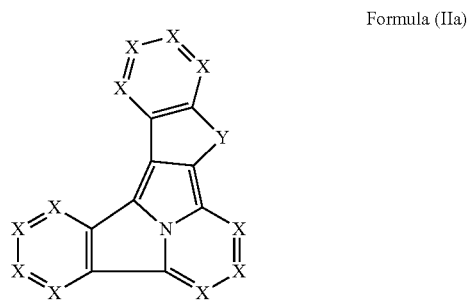

Formula (IIa)

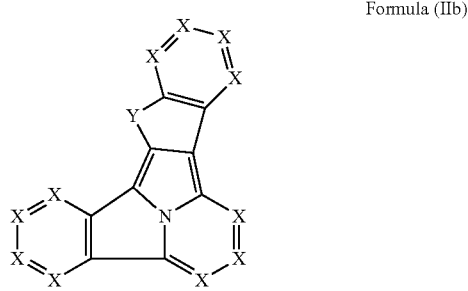

Formula (IIb)

where the symbols Y and X used have the definition given above, especially for formula (I).

Preferably, the compounds of the invention may comprise at least one structure of the formula (IIIa) or (IIIb)

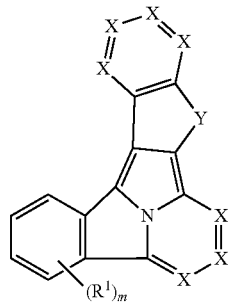

Formula (IIIa)

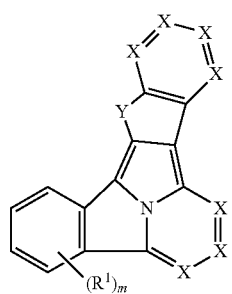

Formula (IIIb)

where the symbols $R^1$, Y and X have the definition given above, especially for formula (I), and m is 0, 1, 2, 3 or 4, preferably 0, 1, 2 or 3, more preferably 0, 1 or 2.

Preferably, the compounds of the invention may comprise at least one structure of the formula (IVa) or (IVb)

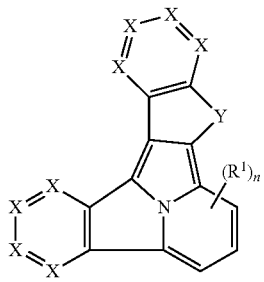

Formula (IVa)

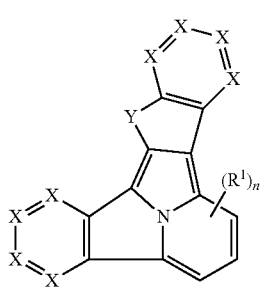

Formula (IVb)

where the symbols $R^1$, Y and X have the definition given above, especially for formula (I), and n is 0, 1, 2 or 3, preferably 0, 1 or 2, more preferably 0 or 1.

In a further preferred embodiment, the compounds of the invention may comprise at least one structure of the formula (Va) or (Vb)

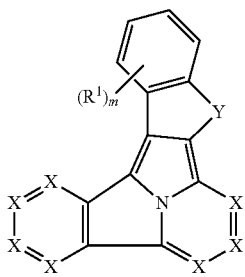

Formula (Va)

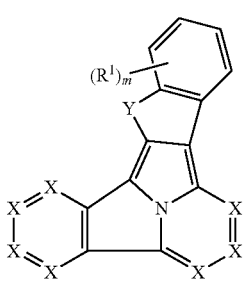

Formula (Vb)

where the symbols $R^1$, Y and X have the definition given above, especially for formula (I), and m is 0, 1, 2, 3 or 4, preferably 0, 1, 2 or 3, more preferably 0, 1 or 2.

It may further be the case that, in structures of formula (I), (IIa), (IIb), (IIIa), (IIIb), (IVa), (IVb), (Va) and/or (Vb), at least one of the Y groups or the Y group is NAr or $NR^1$, preferably NAr, and the X group of the six-membered ring that is in the para position to this Y group is a $CR^1$ group, where the $R^1$ radical in this $CR^1$ group is not H or D and is preferably an aromatic or heteroaromatic ring system which has 5 to 40 aromatic ring atoms and may in each case be substituted by one or more $R^2$ radicals.

It may also be the case that, in structures of formula (I), (IIa), (IIb), (IIIa), (IIIb), (IVa), (IVb), (Va) and/or (Vb), the X group of the nitrogen-containing six-membered ring that is in the para position to the nitrogen atom is a $CR^1$ group, where the $R^1$ radical in this $CR^1$ group is not H or D and is preferably an aromatic or heteroaromatic ring system which has 5 to 40 aromatic ring atoms and may in each case be substituted by one or more $R^2$ radicals.

Preference is also given to compounds having structures in which not more than two X groups per ring are N and preferably at least one, more preferably at least two, of the X groups per ring are selected from C—H and C-D.

Furthermore, preference is given to compounds having structures of formula (I), (IIa), (IIb), (IIia), (IIIb), (IVa), (IVb), (Va) and/or (Vb) in which not more than four, preferably not more than two, X groups are N, and more preferably all the X groups are $CR^1$, where preferably not more than four, more preferably not more than three and especially preferably not more than two of the $CR^1$ groups that X represents are not the CH group.

Preferably, the compounds of the invention may comprise at least one structure of the formula (VIa) or (VIb)

Formula (VIa)

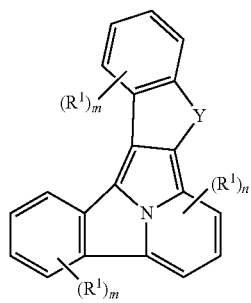

Formula (VIb)

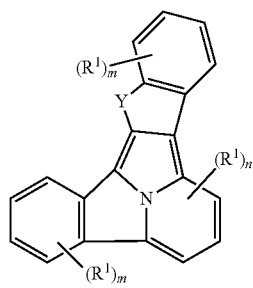

where the symbols $R^1$ and Y have the definition given above, especially for formula (I), m is the same or different at each instance and is 0, 1, 2, 3 or 4, preferably 0, 1, 2 or 3, more preferably 0, 1 or 2, and n is 0, 1, 2 or 3, preferably 0, 1 or 2, more preferably 0 or 1.

It may also be the case that, in structures of the formulae (VIa) and/or (VIb), the sum total of the indices m and n is not more than 6, preferably not more than 4 and more preferably not more than 2.

It may also be the case that, in the formulae (I), (IIa), (IIb), (IIc), (IId), (IIIa), (IIIb), (IVa), (IVb), (Va), (Vb), (VIa) and/or (VIb), there is exactly one $R^1$ radical or there are exactly two $R^1$ radicals that is/are not H or D, such that the other X groups are N, CH or CD, or the sum total of the indices m and n is exactly one or two. Preferably, at least one of these $R^1$ radicals is bonded to the nitrogen-containing aromatic six-membered ring in these formulae. If the Y group can be represented by an NAr radical, it is preferably possible for at least one of these $R^1$ radicals to be bonded to the aromatic six-membered ring that is bonded to the Y group. This substituent $R^1$ is preferably in the para position to the nitrogen atom of the six-membered ring or to the bonding site of the Y group.

In a further-preferred embodiment, the compounds of the invention may have at least one structure of the formula (VIIa) or (VIIb)

Formula (VIIa)

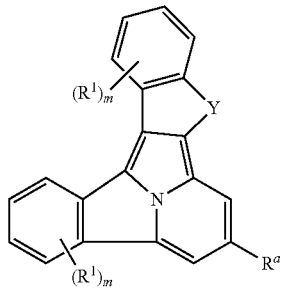

Formula (VIIb)

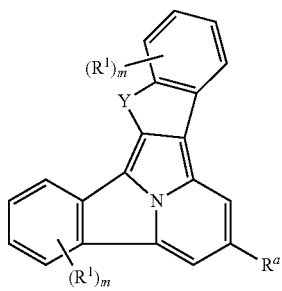

where the symbols $R^1$ and Y used have the definition given above, especially for formula (I), where the symbols $R^1$ and Y have the definition given above, especially for formula (I), $R^a$ is OH, $OR^2$, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, $R^a$ may form a ring system with one or more, preferably adjacent $R^1$ radicals; m is the same or different at each instance and is 0, 1, 2, 3 or 4, preferably 0, 1, 2 or 3, more preferably 0, 1 or 2, where $R^2$ has the definition given above, especially for formula (I). Y is preferably NAr.

In a further preferred embodiment, the compounds of the invention may comprise at least one structure of the formula (VIIIa) or (VIIIb)

Formula (VIIIa)

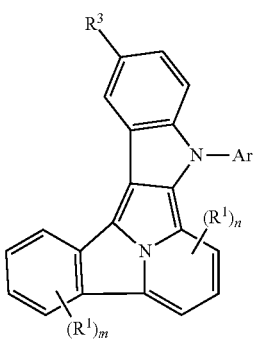

Formula (VIIIb)

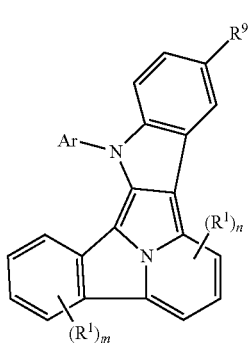

where the symbols $R^1$ and Ar have the definition given above, especially for formula (I), $R^a$ has the definition given above, especially for formula (VIIa) or (VIIb), m is 0, 1, 2, 3 or 4, preferably 0, 1, 2 or 3, more preferably 0, 1 or 2, and n is 0, 1, 2 or 3, preferably 0, 1 or 2, more preferably 0 or 1.

Preferably, the compounds of the invention may have at least one structure of the formula (IXa) or (IXb)

Formula (IXa)

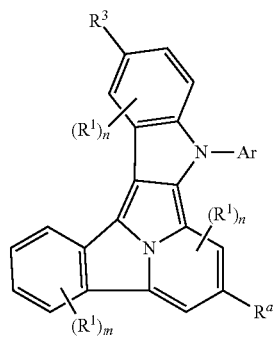

Formula (IXb)

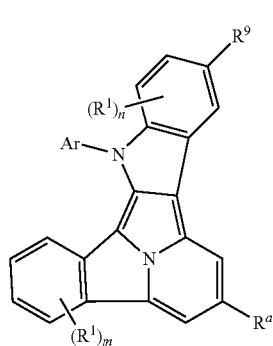

where the symbols $R^1$ and Ar used have the definition given above, especially for formula (I), $R^a$ has the definition given above, especially for formula (VIIa) or (VIIb), m is 0, 1, 2, 3 or 4, preferably 0, 1, 2 or 3, more preferably 0, 1 or 2, and n is 0, 1, 2 or 3, preferably 0, 1 or 2, more preferably 0 or 1, most preferably 0.

It may also be the case that, in structures of the formulae (VIIa), (VIIb), (VIIIa), (VIIIb), (IXa) and/or (IXb), the sum total of the indices m and n is not more than 6, preferably not more than 4 and more preferably not more than 2. Especially preferably, the sum total of the indices m and n in structures of the formulae (VIIa), (VIIb), (VIIIa), (VIIIb), (IXa) and/or (IXb) is 0, such that these structures, apart from the $R^a$ group, do not have any further substituents $R^1$.

Preferably, the $R^a$ radical is an aromatic or heteroaromatic ring system having 5 to 24 aromatic ring atoms, preferably having 6 to 13 aromatic ring atoms, which may be substituted in each case by one or more $R^2$ radicals, but is preferably unsubstituted. The preferred groups that the $R^a$ radical may represent especially include phenyl, ortho-, meta- or para-biphenyl, terphenyl, especially branched terphenyl, quaterphenyl, especially branched quaterphenyl, 1- or 2-naphthyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3-, 4- or N-carbazolyl and indenocarbazolyl, each of which may be substituted by one or more $R^2$ radicals, but are preferably unsubstituted.

In a further embodiment, the aforementioned structures of the formulae (I), (IIa), (IIb), (IIc), (IId), (IIIa), (IIIb), (IVa), (IVb), (Va), (Vb), (VIa) and/or (VIb) do not comprise any substituents on the base skeleton, such that X is N or CH/CD, more preferably CH, or the sum total of the indices n and m is 0.

In a further-preferred embodiment, the compounds of the invention may comprise at least one structure of the formula (Xa) or (Xb)

Formula (Xa)

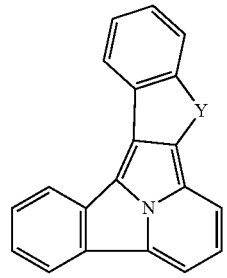

Formula (Xb)

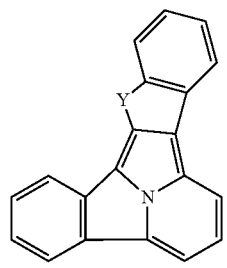

where the symbol Y has the definition given above, especially for formula (I), and is preferably $NR^1$ or NAr, more preferably NAr.

It may further be the case that the substituents $R^1$ and/or $R^a$ of the heteroaromatic ring system of the formulae (I), (IIa), (IIb), (IIc), (IId), (IIIa), (IIIb), (IVa), (IVb), (Va), (Vb), (VIa), (VIb), (VIIa), (VIIb), (VIIIa), (VIIIb), (IXa) and/or (IXb) do not form a fused aromatic or heteroaromatic ring system, preferably any fused ring system, with the ring atoms of the heteroaromatic ring system. This includes the formation of a fused ring system with possible $R^2$, $R^3$ substituents which may be bonded to the $R^1$ radicals.

In a preferred configuration, compounds of the invention can be represented by structures of the formula (I), (IIa), (IIb), (IIc), (IId), (IIIa), (IIIb), (IVa), (IVb), (Va), (Vb), (VIa), (VIb), (VIIa), (VIIb), (VIIIa), (VIIIb), (IXa), (IXb), (Xa) and/or (Xb). Preferably, compounds comprising structures of formula (I), (IIa), (IIb), (IIc), (IId), (IIIa), (IIIb), (IVa), (IVb), (Va), (Vb), (VIa), (VIb), (VIIa), (VIIb), (VIIIa), (VIIIb), (IXa), (IXb), (Xa) and/or (Xb) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

If a compound of the invention contains an Ar and/or $Ar^1$ group, the aromatic or heteroaromatic group of the aromatic or heteroaromatic ring system represented by the symbol Ar or $Ar^1$ is preferably bonded to the respective atom of the further group directly, i.e. via an atom of the aromatic or heteroaromatic group. Preferably, the symbol Ar or $Ar^1$ represents an aryl or heteroaryl group, where the configurations of these groups set out above and hereinafter are applicable to the further properties.

In a further embodiment, the compound of the invention may comprise a hole transport group, it being preferable that the Ar group or an $R^1$ group present in a Y group, or an $R^1$ group bonded to the base skeleton, comprises and preferably represents a hole transport group. Hole transport groups are known in the technical field, and they preferably include triarylamine or carbazole groups.

It may preferably be the case that the hole transport group comprises a group and preferably is a group selected from the formulae (H-1) to (H-3)

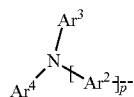

Formula (H-1)

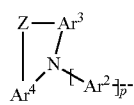

Formula (H-2)

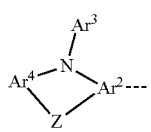

Formula (H-3)

where the dotted bond marks the position of attachment to the nitrogen atom and in addition:

$Ar^2$, $Ar^3$, $Ar^4$ is in each case independently an aromatic ring system having 6 to 40 carbon atoms or a heteroaromatic ring system having 3 to 40 carbon atoms, each of which may be substituted by one or more $R^1$ radicals;

Z is $C(R^1)_2$, $Si(R^1)_2$, C=O, N—$Ar^1$, $BR^1$, $PR^1$, $PO(R^1)$, SO, $SO_2$, Se, O or S, preferably $C(R^1)_2$, N—$Ar^1$, O or S, where the symbols $Ar^1$ and $R^1$ have the definition given above, especially for formula (I), where the presence of an N—N bond is preferably ruled out, and so, in the case that Y=NAr, the index p=1.

Accordingly, the Ar group may comprise a radical of the formulae (H-1), (H-2) and/or (H-3) and may preferably be a radical of the formula (H-1), (H-2) or (H-3).

It may further be the case that the Ar group comprises a group and preferably is a group selected from the formulae (H-4) to (H-26)

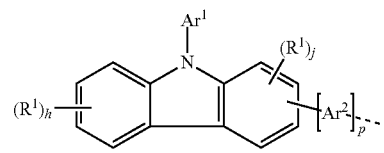

Formula (H-4)

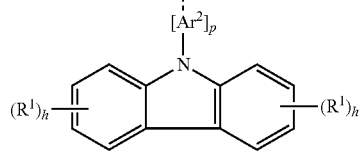

Formula (H-5)

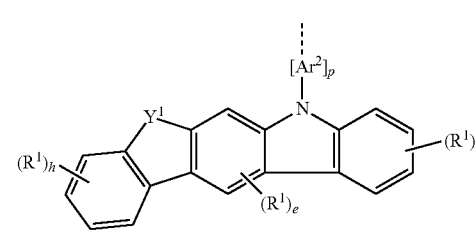

Formula (H-6)

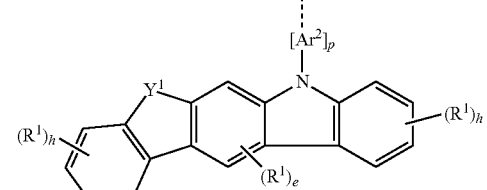

Formula (H-7)

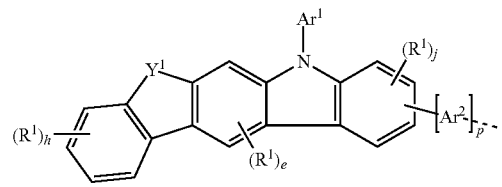

Formula (H-8)

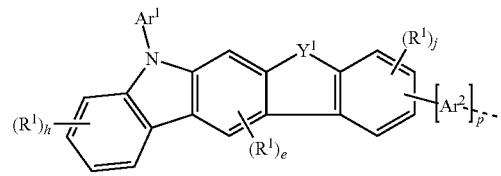

Formula (H-9)

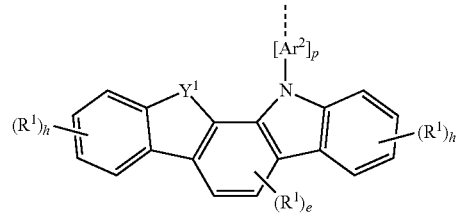

Formula (H-10)

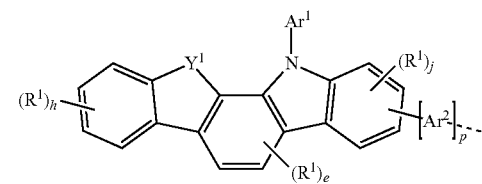

Formula (H-11)
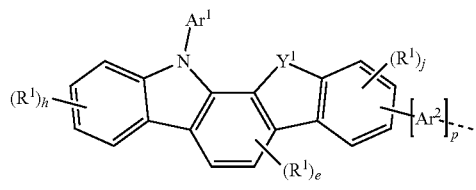
Formula (H-12)
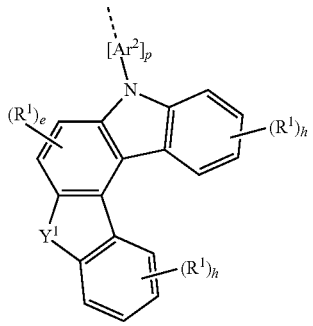
Formula (H-13)
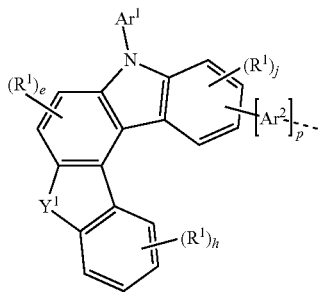
Formula (H-14)
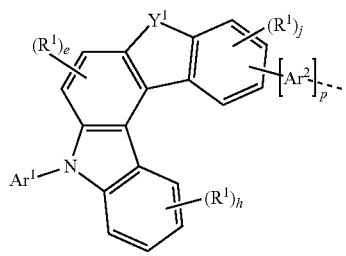
Formula (H-15)
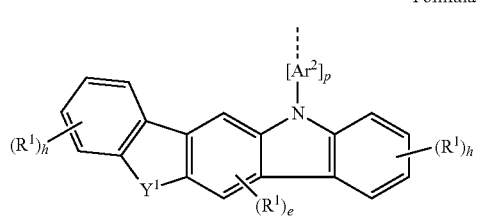
Formula (H-16)
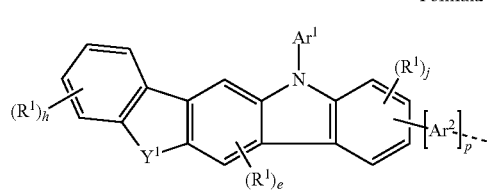
Formula (H-17)
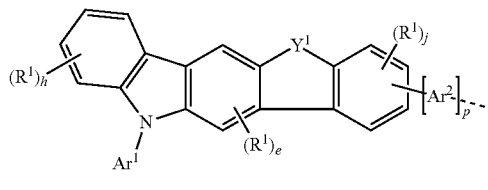
Formula (H-18)
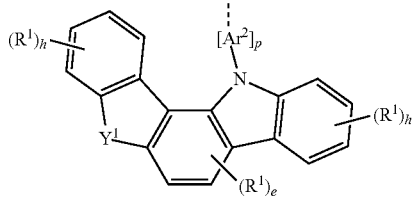
Formula (H-19)
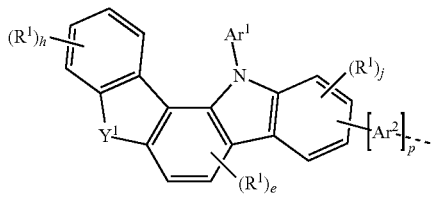
Formula (H-20)
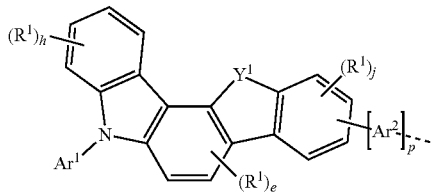
Formula (H-21)
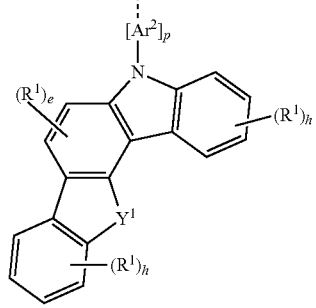
Formula (H-22)
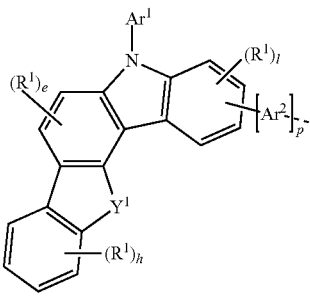

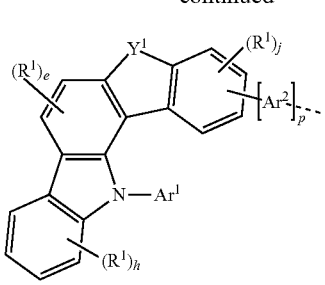

Formula (H-23)

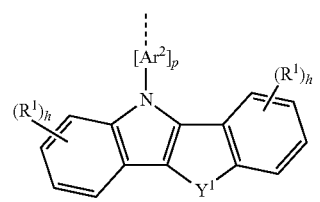

Formula (H-24)

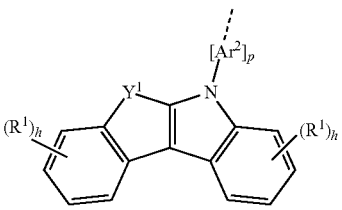

Formula (H-25)

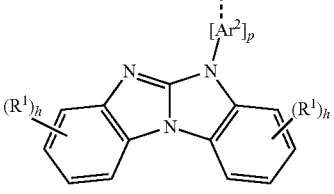

Formula (H-26)

where $Y^1$ represents O, S, $C(R^1)_2$ or $NAr^1$, the dotted bond marks the position of attachment to the nitrogen atom, e is 0, 1 or 2, j is 0, 1, 2 or 3, h is the same or different at each instance and is 0, 1, 2, 3 or 4, p is 0 or 1, $Ar^1$ and $R^1$ have the definition given above, especially for formula (I), and $Ar^2$ has the definition given above, especially for formula (H-1) or (H-2), where the presence of an N—N bond is preferably ruled out, such that, in the case that Y=NAr in the formulae (H-5), (H-6), (H-9), (H-12), (H-15), (H-18), (H-21), (H-24), (H-25) and (H-26), the index p=1.

The hole transport groups of the formulae (H-1) to (H-26) detailed above constitute preferred $R^1$ radicals of formula (I) or preferred embodiments of this formula, where in this case the $R^1$ groups detailed in the formulae (H-1) to (H-26) should be replaced by $R^2$ radicals. The Z, $Ar^2$, $Ar^3$, $Ar^4$ groups, in the case that the $R^1$ radical of formula (I) represents a hole transport group, may have $R^2$ radicals as substituents rather than the $R^1$ radicals mentioned. The presence of an N—N bond is preferably ruled out, and so, in the case that Y=$NR^1$ in the formulae (H-1), (H-2), (H-5), (H-6), (H-9), (H-12), (H-15), (H-18), (H-21), (H-24), (H-25) and (H-26), the index p=1.

It is clear from the above wording that, if the index p=0, the corresponding $Ar^2$ group is absent and a bond is formed.

Preferably, the $Ar^2$ group may form through-conjugation with the aromatic or heteroaromatic radical or the nitrogen atom to which the $Ar^2$ group of the formulae (H-1) to (H-26) may be bonded.

In a further preferred embodiment of the invention, $Ar^2$ is an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $Ar^2$ is an aromatic ring system having 6 to 10 aromatic ring atoms or a heteroaromatic ring system having 6 to 13 heteroaromatic ring atoms, each of which may be substituted by one or more $R^1$ radicals, but is preferably unsubstituted, where $R^1$ may have the definition given above, especially for formula (I).

Further preferably, the symbol $Ar^2$ shown in formulae (H-1) to (H-26) inter alia is an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may further be the case that the $Ar^2$ group shown in formulae (H-1) to (H-26) comprises an aromatic or heteroaromatic ring system having not more than two fused aromatic and/or heteroaromatic 6-membered rings; preferably it does not comprise any fused aromatic or heteroaromatic ring system with fused 6-membered rings. Accordingly, naphthyl structures are preferred over anthracene structures. In addition, fluorenyl, spirobifluorenyl, dibenzofuranyl and/or dibenzothienyl structures are preferred over naphthyl structures. Particular preference is given to structures having no fusion, for example phenyl, biphenyl, terphenyl and/or quaterphenyl structures.

It may further be the case that the $Ar^2$ group shown in formulae (H-1) to (H-26) inter alia has not more than 1 nitrogen atom, preferably not more than 2 heteroatoms, particularly preferably not more than one heteroatom and especially preferably no heteroatom.

In a further preferred embodiment of the invention, $Ar^3$ and/or $Ar^4$ are the same or different at each instance and are an aromatic or heteroaromatic ring system having 6 to 24 aromatic ring atoms, preferably 6 to 18 aromatic ring atoms, and are more preferably an aromatic ring system having 6 to 12 aromatic ring atoms or a heteroaromatic ring system having 6 to 13 aromatic ring atoms, each of which may be substituted by one or more $R^1$ radicals, but is preferably unsubstituted, where $R^1$ may have the definition given above, especially in formula (I).

In a further preferred embodiment, the compound of the invention may comprise an electron transport group, it being preferable that the Ar group or an $R^1$ group present in a Y group, or an $R^1$ group bonded to the base skeleton, or the $R^a$ group, comprises and preferably represents an electron transport group. Electron transport groups are widely known in the technical field and promote the ability of compounds to transport and/or conduct electrons.

Furthermore, surprising advantages are exhibited by compounds comprising at least one structure of formula (I) or preferred embodiments thereof in which the Y group contains at least one Ar or $R^1$ radical or the base skeleton comprises at least one $R^1$ or $R^a$ radical that comprises a structure from the group of the pyridines, pyrimidines, pyrazines, pyridazines, triazines, quinazolines, quinoxalines, quinolines, isoquinolines, imidazoles and/or benzimidazoles or is selected from the structures mentioned, particular preference being given to pyrimidines, triazines and quinazolines.

In a preferred configuration of the present invention, it may be the case that the Y group contains at least one Ar radical which is a group that can be represented by the formula (QL)

Formula (QL)

in which $L^1$ represents a bond or an aromatic or heteroaromatic ring system which has 5 to 40, preferably 5 to 30, aromatic ring atoms and may be substituted by one or more $R^1$ radicals, and Q is an electron transport group, where $R^1$ has the definition given above, especially for formula (I).

Preferably, the $L^1$ group may form through-conjugation with the Q group and the atom to which the $L^1$ group of formula (QL) is bonded. Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the sp³-hybridized carbon atom in position 9 does prevent fusion of these rings, but conjugation is possible since this sp³-hybridized carbon atom in position 9 does not necessarily lie between the electron-transporting Q group and the atom to which the $L^1$ group of formula (QL) is bonded. In contrast, in the case of a spirobifluorene structure, through-conjugation can be formed if the bond between the Q group and the atom to which the $L^1$ group of formula (QL) is bonded is via the same phenyl group in the spirobifluorene structure or via phenyl groups in the spirobifluorene structure that are bonded directly to one another and are in one plane. If the bond between the Q group and the atom to which the $L^1$ group of formula (QL) is bonded is via different phenyl groups in the spirobifluorene structure bonded via the sp³-hybridized carbon atom in position 9, the conjugation is interrupted.

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $L^1$ is a bond or an aromatic ring system having 6 to 10 aromatic ring atoms or a heteroaromatic ring system having 6 to 13 heteroaromatic ring atoms, each of which may be substituted by one or more $R^1$ radicals, but is preferably unsubstituted, where $R^1$ may have the definition given above, especially for formula (I).

Further preferably, the symbol $L^1$ shown in formula (QL) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the $L^1$ group shown in formula (QL) comprises an aromatic or heteroaromatic ring system having not more than two fused aromatic and/or heteroaromatic six-membered rings, preferably does not comprise any fused aromatic or heteroaromatic ring system with six-membered rings fused directly to one another. Accordingly, naphthyl structures are preferred over anthracene structures. In addition, fluorenyl, spirobifluorenyl, dibenzofuranyl and/or dibenzothienyl structures are preferred over naphthyl structures. Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^1$ radicals, but are preferably unsubstituted.

It may further be the case that the $L^1$ group shown in formula (QL) inter alia has not more than 1 nitrogen atom, preferably not more than 2 heteroatoms, especially preferably not more than one heteroatom and more preferably no heteroatom.

Preferably, the Q group shown in the formula (QL) inter alia, or the electron transport group, may be selected from structures of the formulae (Q-1), (Q-2), (Q-3), (Q-4), (Q-5), (Q-6), (Q-7), (Q-8), (Q-9) and/or (Q-10)

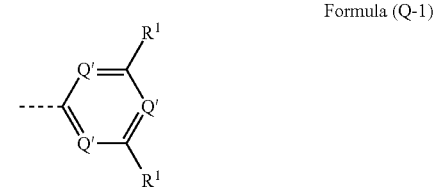
Formula (Q-1)

Formula (Q-2)

Formula (Q-3)

Formula (Q-4)

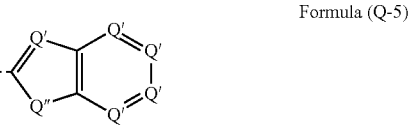
Formula (Q-5)

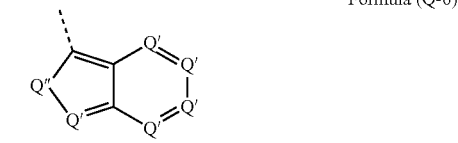
Formula (Q-6)

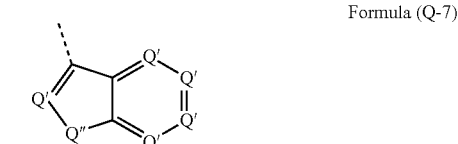
Formula (Q-7)

-continued

Formula (Q-8)

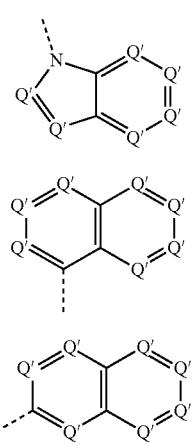

Formula (Q-9)

Formula (Q-10)

where the dotted bond marks the position of attachment,
Q' is the same or different at each instance and is CR¹ or N,
where at least one Q' is N;
Q" is NR¹, O or S; and
R¹ is as defined above, especially in formula (I).

In addition, the Q group shown in the formula (QL) inter alia, or the electron transport group, may preferably be selected from a structure of the formulae (Q-11), (Q-12), (Q-13), (Q-14) and/or (Q-15)

Formula (Q-11)

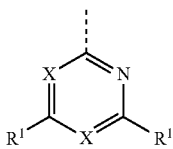

Formula (Q-12)

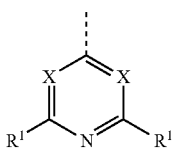

Formula (Q-13)

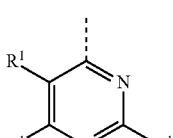

Formula (Q-14)

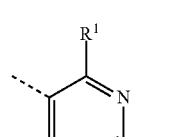

Formula (Q-15)

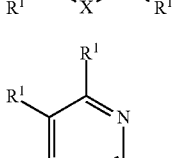

where the symbol R¹ has the definition given above for formula (I) inter alia, X is N or CR¹ and the dotted bond marks the position of attachment, where X is preferably a nitrogen atom.

In a further embodiment, the Q group shown in the formula (QL) inter alia, or the electron transport group, may be selected from structures of the formulae (Q-16), (Q-17), (Q-18), (Q-19), (Q-20), (Q-21) and/or (Q-22)

Formula (Q-16)

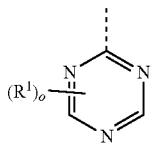

Formula (Q-17)

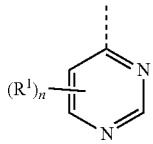

Formula (Q-18)

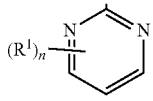

Formula (Q-19)

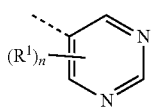

Formula (Q-20)

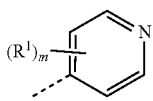

Formula (Q-21)

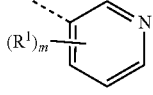

Formula (Q-22)

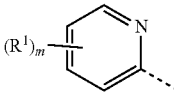

in which the symbol R¹ has the definition detailed above for formula (I) inter alia, the dotted bond marks the position of attachment and m is 0, 1, 2, 3 or 4, preferably 0, 1 or 2, n is 0, 1, 2 or 3, preferably 0, 1 or 2, and o is 0, 1 or 2, preferably 1 or 2. Preference is given here to the structures of the formulae (Q-16), (Q-17), (Q-18) and (Q-19).

In a further embodiment, the Q group shown in the formula (QL) inter alia, or the electron transport group, may be selected from structures of the formulae (Q-23), (Q-24) and/or (Q-25)

Formula (Q-23)

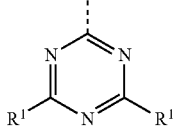

Formula (Q-24)

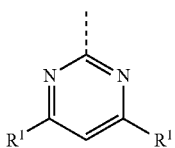

Formula (Q-25)

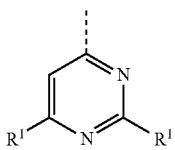

in which the symbol R¹ has the definition set out above for formula (I) inter alia, and the dotted bond marks the position of attachment.

In a further embodiment, the Q group shown in the formula (QL) inter alia, or the electron transport group, may be selected from structures of the formulae (Q-26), (Q-27), (Q-28), (Q-29) and/or (Q-30)

Formula (Q-26)

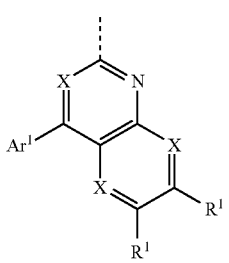

Formula (Q-27)

Formula (Q-28)

Formula (Q-29)

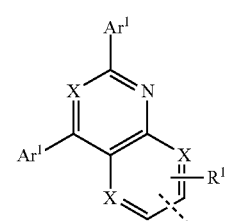

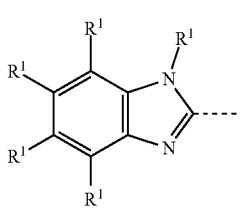

Formula (Q-30)

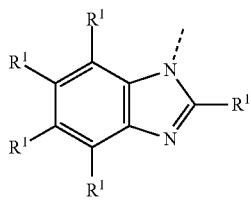

where symbols X, Ar¹ and R¹ have the definition given above for formula (I) inter alia and the dotted bond marks the position of attachment. Preferably, in the structures of the formulae (Q-26), (Q-27) and (Q-28), exactly one X is a nitrogen atom.

Preferably, the Q group shown in the formula (QL) inter alia, or the electron transport group, may be selected from structures of the formulae (Q-31), (Q-32), (Q-33), (Q-34), (Q-35), (Q-36), (Q-37), (Q-38), (Q-39), (Q-40), (Q-41), (Q-42), (Q-43) and/or (Q-44)

Formula (Q-31)

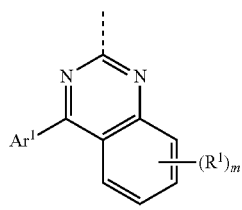

Formula (Q-32)

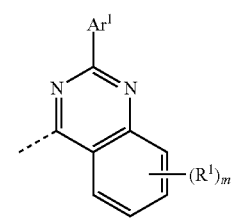

Formula (Q-33)

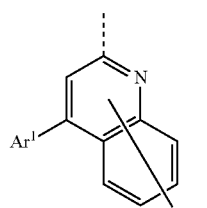

Formula (Q-34)

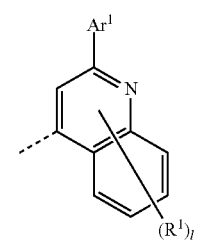

Formula (Q-35)
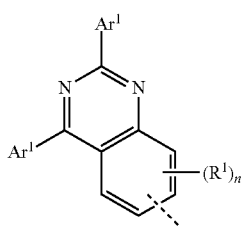

Formula (Q-36)
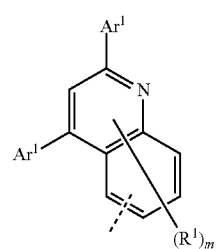

Formula (Q-37)
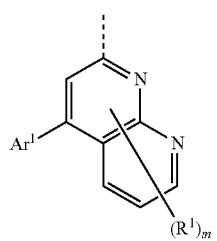

Formula (Q-38)
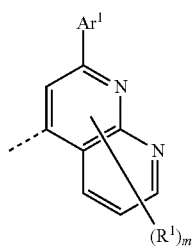

Formula (Q-39)
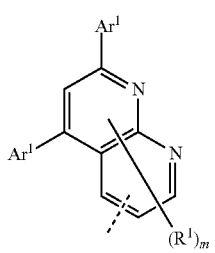

Formula (Q-40)
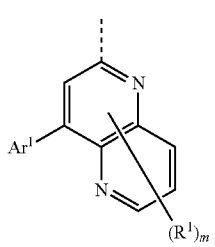

Formula (Q-41)
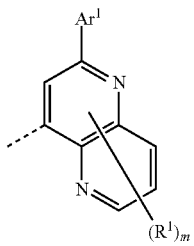

Formula (Q-42)
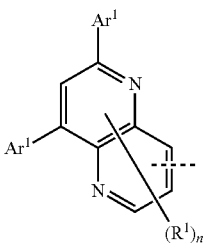

Formula (Q-43)
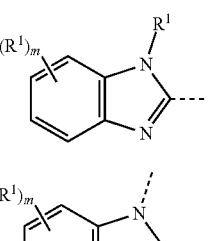

Formula (Q-44)

in which the symbols $Ar^1$ and $R^1$ have the definition set out above for formula (I) inter alia, the dotted bond marks the position of attachment and m is 0, 1, 2, 3 or 4, preferably 0, 1 or 2, n is 0, 1, 2 or 3, preferably 0 or 1, n is 0, 1, 2 or 3, preferably 0, 1 or 2, and l is 0, 1, 2, 3, 4 or 5, preferably 0, 1 or 2.

The electron transport groups of the formulae (Q-1) to (Q-44) detailed above also constitute preferred $R^1$ radicals of formula (I) or preferred embodiments of this formula, where in this case the $R^1$ groups detailed in the formulae (Q-1) to (Q-44) should be replaced by $R^2$ radicals. The $R^1$ radical may also contain one or more electron transport groups, where preferred embodiments can be represented in accordance with the formula (QL). In this case, the connecting $L^1$ group may have $R^2$ radicals as substituents rather than the $R^1$ radicals mentioned. The presence of an N—N bond is preferably ruled out.

It may also be the case that the Ar group comprises a hole transport group and an electron transport group. According to the configuration, preferred groups may be formed from the above-detailed formulae (H-1) to (H-26) or (Q-1) to (Q-44), where, for example, the $R^1$ groups may be a hole transport or electron transport group, where, for example, the $R^1$ radicals shown in the formulae (H-1) to (H-26) or (Q-1) to (Q-44) may be replaced by corresponding $R^2$ radicals.

In a further preferred embodiment of the invention, $Ar^1$ is the same or different at each instance and is an aromatic or heteroaromatic ring system, preferably an aryl or heteroaryl radical having 5 to 24 aromatic ring atoms, preferably having 6 to 18 aromatic ring atoms, and is more preferably an aromatic ring system, preferably an aryl radical having 6 to 12 aromatic ring atoms, or a heteroaromatic ring system, preferably a heteroaryl group having 5 to 13 aromatic ring atoms, each of which may be substituted by one or more $R^2$ radicals, but is preferably unsubstituted, where $R^2$ may have the definition detailed above, especially in formula (I). Preferably, the symbol $Ar^1$ is an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example a carbon or nitrogen atom of the (H-1) to (H-26) or (Q-26) to (Q-44) groups shown above.

Advantageously, $Ar^1$ in the formulae (H-1) to (H-26) or (Q-26) to (Q-44) is an aromatic ring system which has 6 to 12 aromatic ring atoms and may be substituted by one or more $R^2$ radicals, but is preferably unsubstituted, where $R^2$ may have the definition detailed above, especially for formula (I).

Preferably, the $R^1$ or $R^2$ radicals in the formulae (H-1) to (H-26) or (Q-1) to (Q-44) do not form a fused ring system with the ring atoms of the aryl group or heteroaryl group $Ar^1$, $Ar^2$, $Ar^3$ and/or $Ar^4$ to which the $R^1$ or $R^2$ radicals are bonded. This includes the formation of a fused ring system with possible substituents $R^2$, $R^3$ which may be bonded to the $R^1$ or $R^2$ radicals.

It may also be the case that the Ar, $Ar^1$, $Ar^2$, $Ar^3$ and/or $Ar^4$ group is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, preferably 9-anthracenyl, phenanthrenyl and/or triphenylenyl, each of which may be substituted by one or more $R^2$ radicals, but are preferably unsubstituted, particular preference being given to phenyl, spirobifluorene, fluorene, dibenzofuran, dibenzothiophene, phenanthrene, triphenylene groups.

When X is $CR^1$ or when the aromatic and/or heteroaromatic groups are substituted by $R^1$ and/or $R^a$ substituents, these $R^1$ substituents are preferably selected from the group consisting of H, D, F, CN, $N(Ar^1)_2$, C(=O)$Ar^1$, P(=O)($Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^2$ radicals, but is preferably unsubstituted, or an aralkyl or heteroaralkyl group which has 5 to 25 aromatic ring atoms and may be substituted by one or more $R^2$ radicals; at the same time, it is optionally possible for two $R^1$ substituents preferably bonded to adjacent carbon atoms to form a monocyclic or polycyclic, aliphatic, aromatic or heteroaromatic ring system which may be substituted by one or more $R^1$ radicals, where the $Ar^1$ group has the definition given above, especially for formula (I). In this case, $R^a$ is not H or D.

More preferably, these $R^1$ and/or $R^a$ substituents are selected from the group consisting of H, D, F, CN, $N(Ar^1)_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more $R^2$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic $R^2$ radicals, but is preferably unsubstituted; at the same time, two $R^1$ substituents preferably bonded to adjacent carbon atoms may optionally form a monocyclic or polycyclic aliphatic ring system which may be substituted by one or more $R^2$ radicals, but is preferably unsubstituted, where $Ar^1$ may have the definition set out above. In this case, $R^a$ is not H or D.

Most preferably, the $R^1$ and/or $R^a$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. In this case, $R^a$ is not H or D.

It may further be the case that, in a structure of formula (I), (IIa), (IIb), (IIc), (IId), (IIIa), (IIIb), (IVa), (IVb), (Va), (Vb), (VIa), (VIb), (VIIa), (VIIb), (VIIIa), (VIIIb), (IXa), (IXb), (Xa) and/or (Xb), at least one $R^1$ or $Ar^1$ radical is a group selected from the formulae ($R^1$-1) to ($R^1$-92), or, in a structure of formula (H-1) to (H-26), (Q-1) to (Q-44), at least one $Ar^1$ or $R^1$ radical is a group selected from the formulae ($R^1$-1) to ($R^1$-92)

Formula ($R^1$-1)

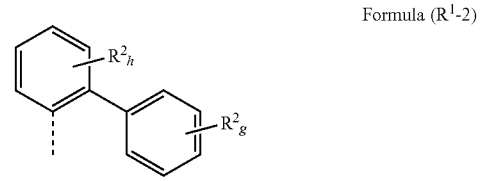

Formula ($R^1$-2)

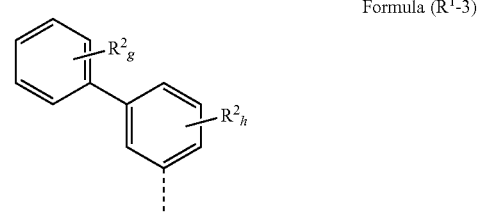

Formula ($R^1$-3)

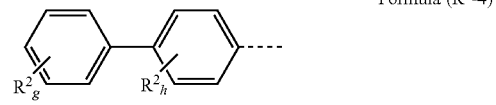

Formula ($R^1$-4)

Formula (R¹-5)
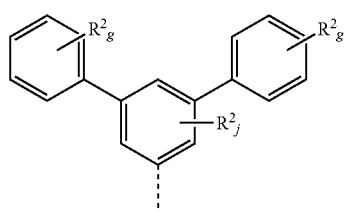
Formula (R¹-6)
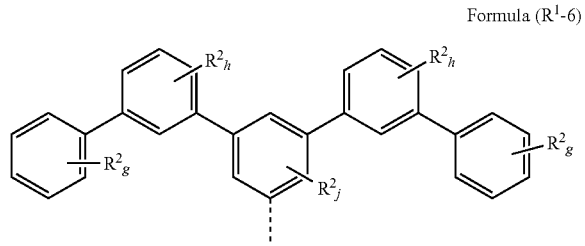
Formula (R¹-7)
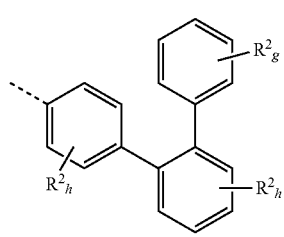
Formula (R¹-8)
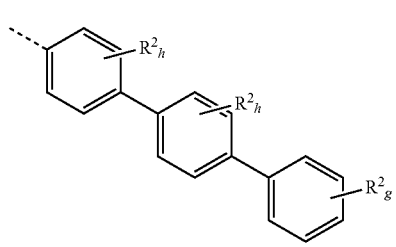
Formula (R¹-9)
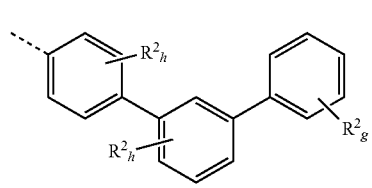
Formula (R¹-10)
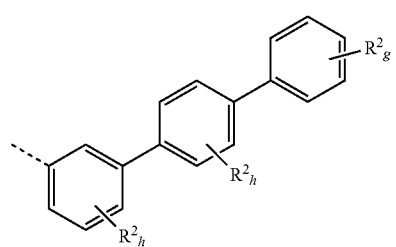
Formula (R¹-11)
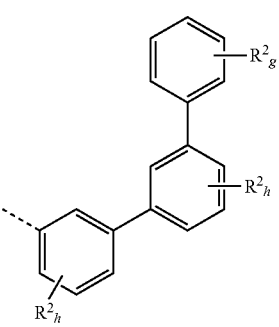
Formula (R¹-12)
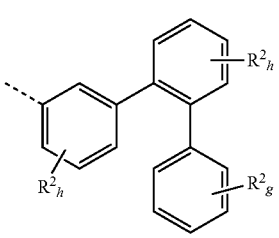
Formula (R¹-13)
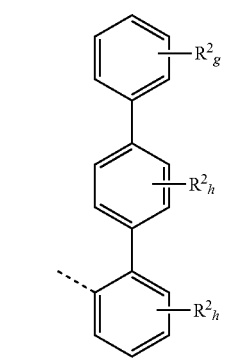
Formula (R¹-14)
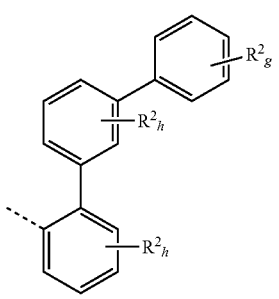
Formula (R¹-15)
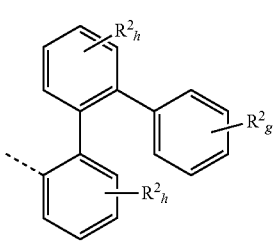

Formula (R¹-16)
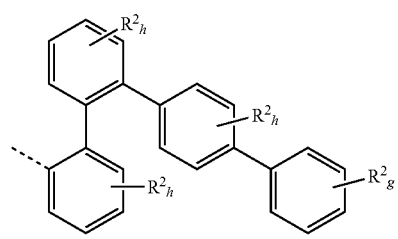
Formula (R¹-17)
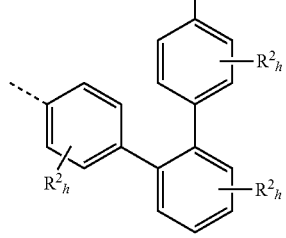
Formula (R¹-18)
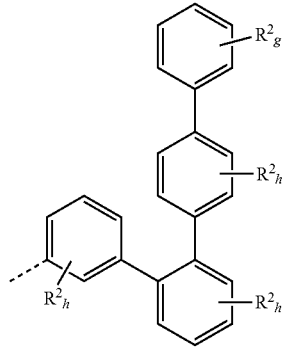
Formula (R¹-19)
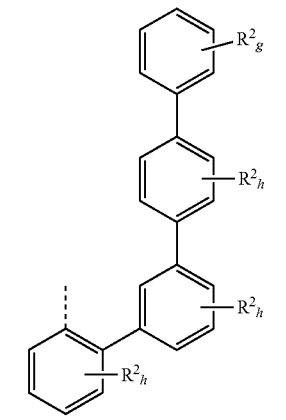
Formula (R¹-20)
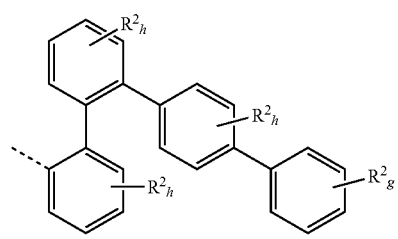
Formula (R¹-21)
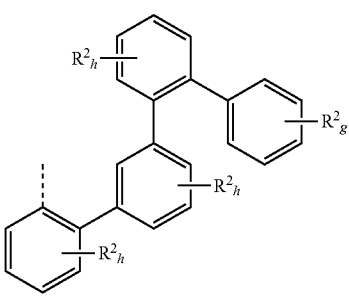
Formula (R¹-22)
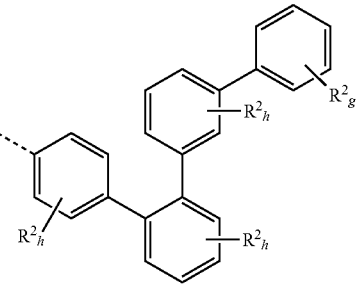
Formula (R¹-23)
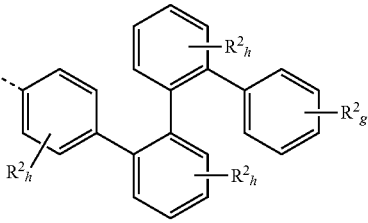
Formula (R¹-24)

Formula (R¹-25)
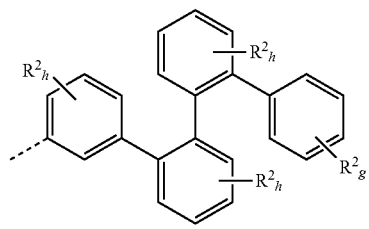
Formula (R¹-26)
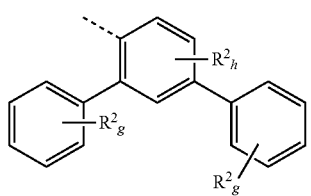
Formula (R¹-27)
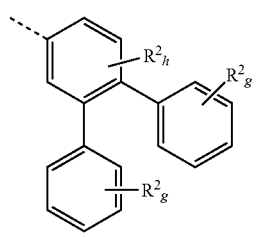
Formula (R¹-28)
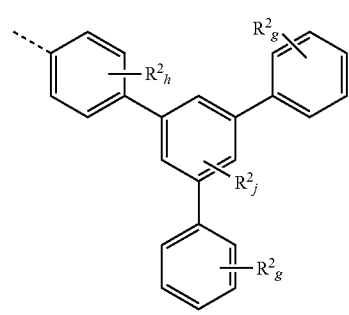
Formula (R¹-29)
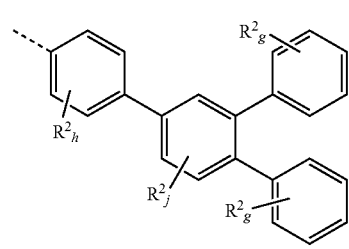
Formula (R¹-30)
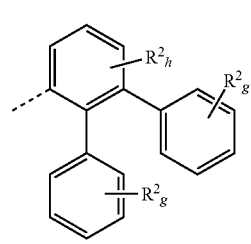
Formula (R¹-31)
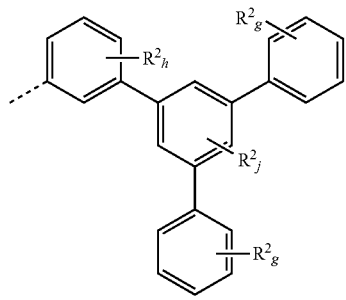
Formula (R¹-32)
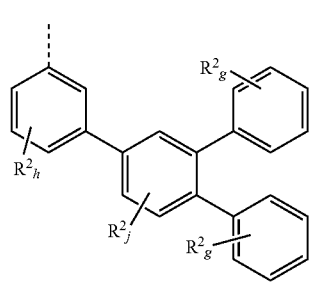
Formula (R¹-33)
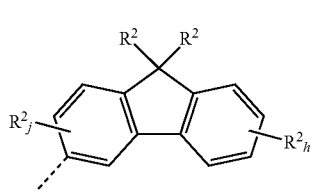
Formula (R¹-34)
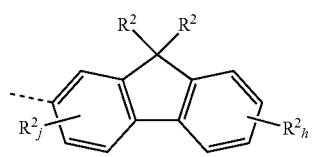
Formula (R¹-35)
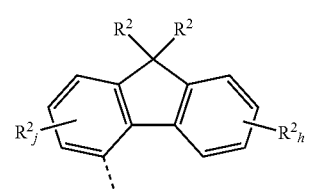
Formula (R¹-36)
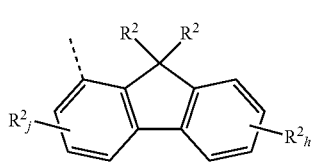
Formula (R¹-37)
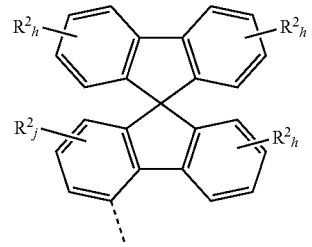

-continued
Formula (R¹-38)
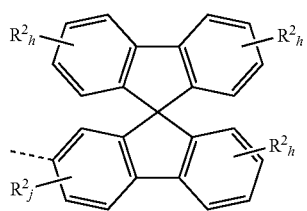
Formula (R¹-39)
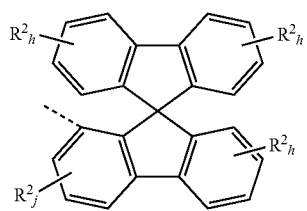
Formula (R¹-40)
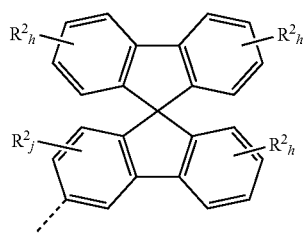
Formula (R¹-41)
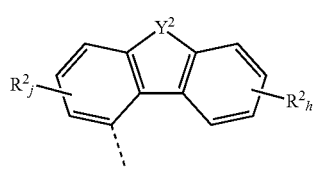
Formula (R¹-42)
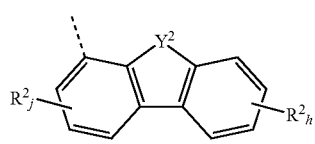
Formula (R¹-43)
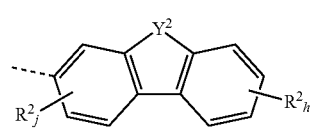
Formula (R¹-44)
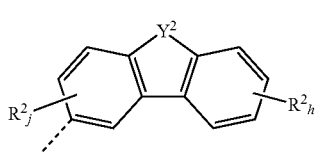
Formula (R¹-45)
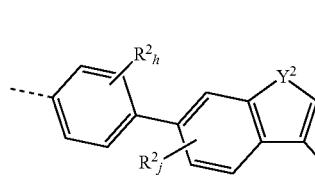
-continued
Formula (R¹-46)
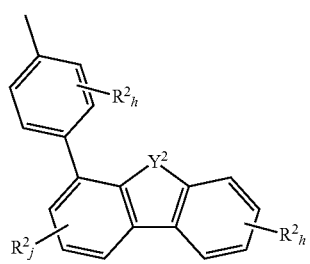
Formula (R¹-47)
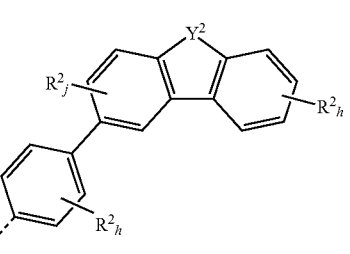
Formula (R¹-48)
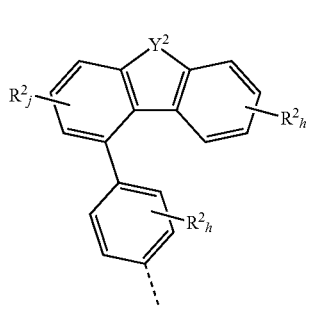
Formula (R¹-49)
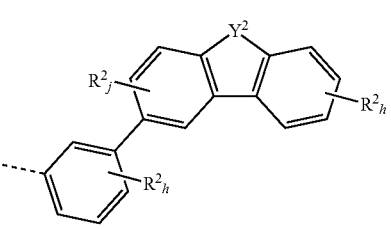
Formula (R¹-50)
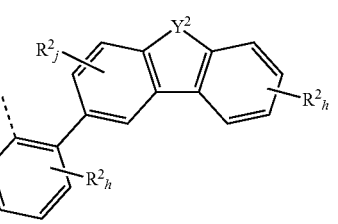
Formula (R¹-51)
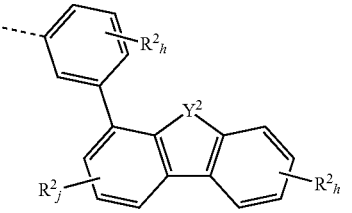

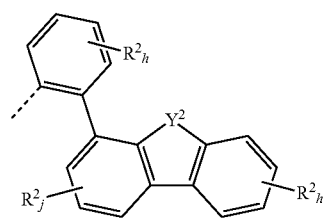
Formula (R¹-52)
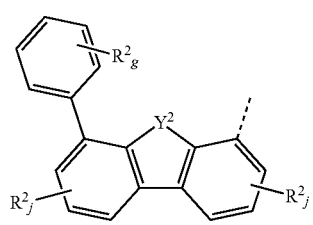
Formula (R¹-53)
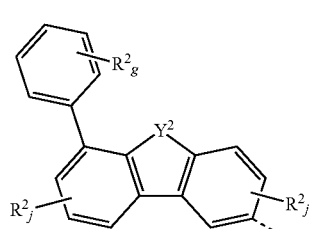
Formula (R¹-54)
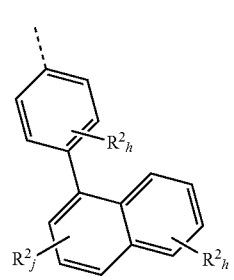
Formula (R¹-55)
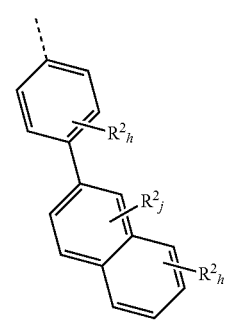
Formula (R¹-56)
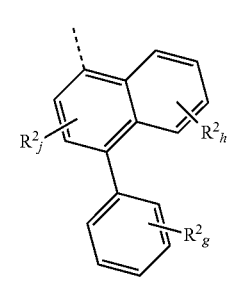
Formula R¹-57)
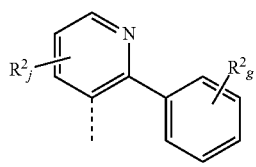
Formula (R¹-58)
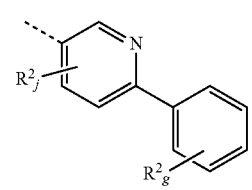
Formula (R¹-59)
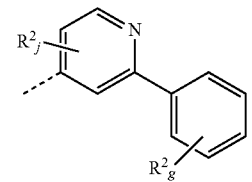
Formula (R¹-60)
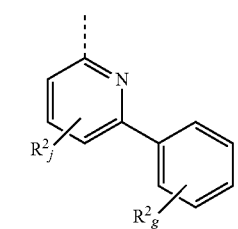
Formula (R¹-61)
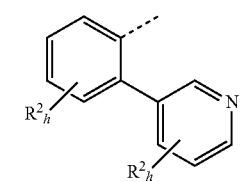
Formula (R¹-62)
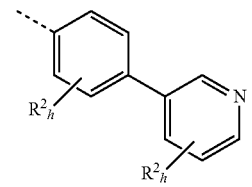
Formula (R¹-63)
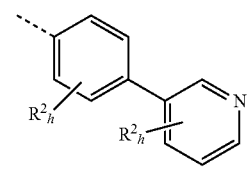
Formula (R¹-64)
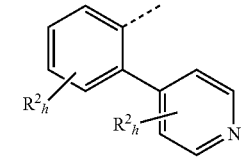
Formula (R¹-65)

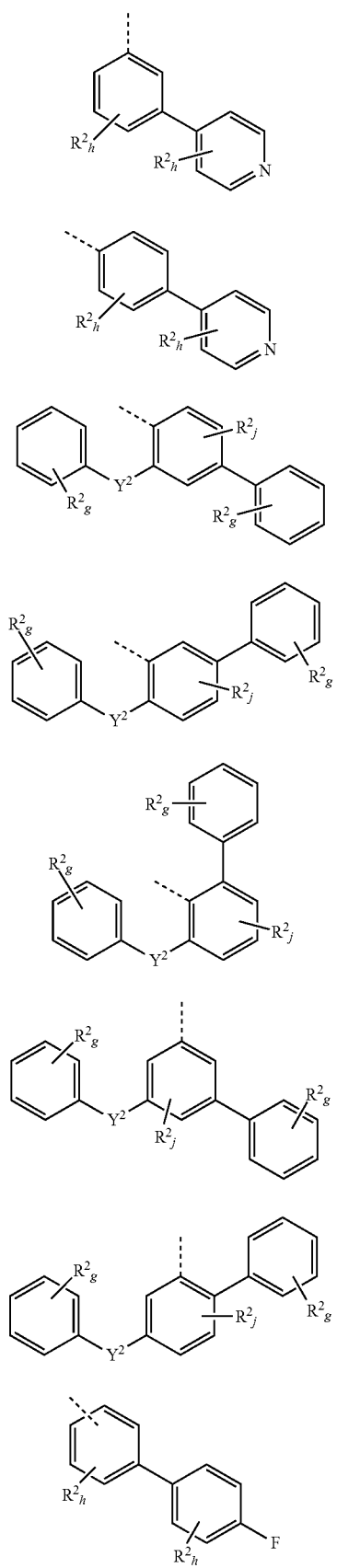
Formula (R¹-66)
Formula (R¹-67)
Formula (R¹-68)
Formula (R¹-69)
Formula (R¹-70)
Formula (R¹-71)
Formula (R¹-72)
Formula (R¹-73)
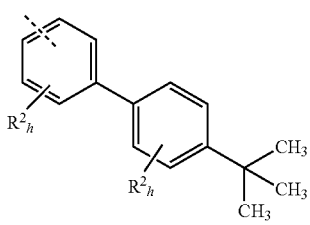
Formula (R¹-74)
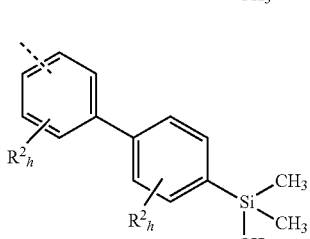
Formula (R¹-75)
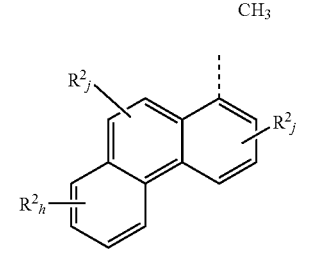
Formula (R¹-76)
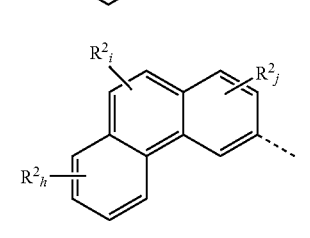
Formula (R¹-77)
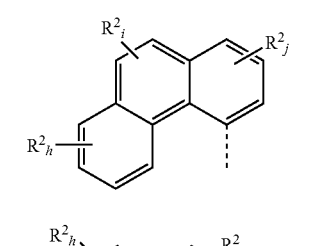
Formula (R¹-78)
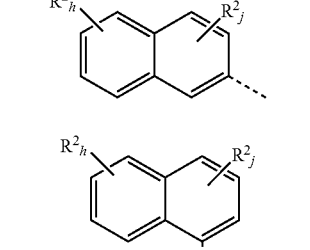
Formula (R¹-79)
Formula (R¹-80)
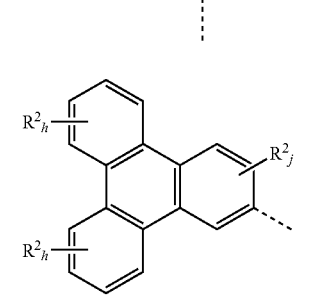
Formula (R¹-81)

-continued

Formula (R¹-82)

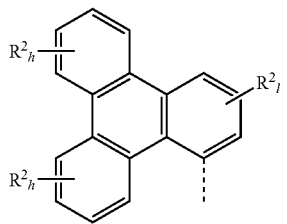

Formula (R¹-83)

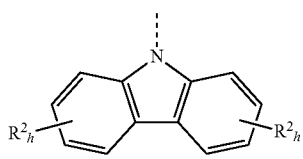

Formula (R¹-84)

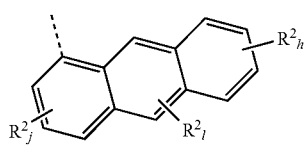

Formula (R¹-85)

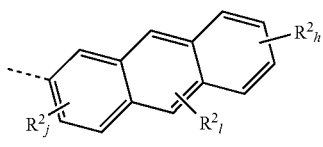

Formula (R¹-86)

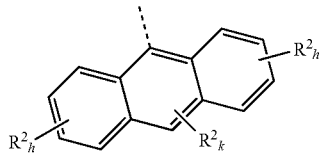

Formula (R¹-87)

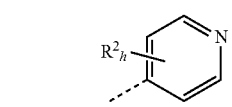

Formula (R¹-88)

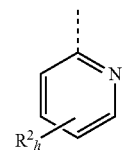

Formula (R¹-89)

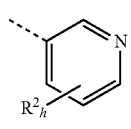

Formula (R¹-90)

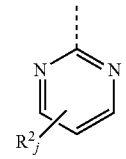

Formula (R¹-91)

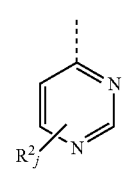

Formula (R¹-92)

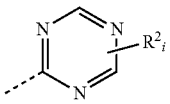

where the symbols used are as follows:

$Y^2$ is O, S or $NR^2$, preferably O or S;

k at each instance is independently 0 or 1;

i at each instance is independently 0, 1 or 2;

j at each instance is independently 0, 1, 2 or 3;

h at each instance is independently 0, 1, 2, 3 or 4;

g at each instance is independently 0, 1, 2, 3, 4 or 5;

$R^2$ may have the definition given above, especially for formula (I);

the dotted bond marks the position of attachment.

Preference is given here to the groups of the formulae $R^1$-1 to $R^1$-56, particular preference to the $R^1$-1, $R^1$-3, $R^1$-5, $R^1$-6, $R^1$-15, $R^1$-29, $R^1$-30, $R^1$-31, $R^1$-32, $R^1$-33, $R^1$-38, $R^1$-39, $R^1$-40, $R^1$-41, $R^1$-42, $R^1$-43, $R^1$-44 and/or $R^1$-45 groups.

It may preferably be the case that the sum total of the indices k, i, j, h and g in the structures of the formula ($R^1$-1) to ($R^1$-92) in each case is not more than 3, preferably not more than 2 and more preferably not more than 1.

Preferably, the $R^2$ radicals in the formulae ($R^1$-1) to ($R^1$-92) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

The above-detailed radicals of the formulae ($R^1$-1) to ($R^1$-92) are preferred Ar radicals of formula (I) or $Ar^3$, $Ar^4$ radicals of formulae (H-1) to (H-3) or preferred embodiments of these formulae, where, in this case, the $R^2$ groups shown in the formulae ($R^1$-1) to ($R^1$-92) are to be replaced by $R^1$ radicals. The preferences detailed above with regard to the formulae ($R^1$-1) to ($R^1$-92) are correspondingly applicable.

Preference is given to compounds comprising at least one structure of the formulae (H-1) to (H-26) in which the $Ar^2$ group is a group selected from the formulae ($L^1$-1) to ($L^1$-108) and/or to compounds comprising structures of the formula (QL) in which the $L^1$ group is a bond or is a group selected from the formulae ($L^1$-1) to ($L^1$-108)

Formula (L¹-1)

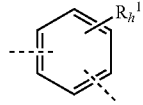

Formula (L¹-2)

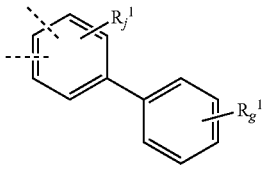

Formula (L¹-3)
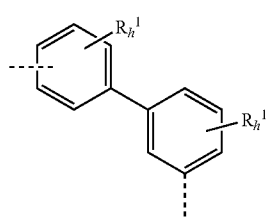
Formula (L¹-4)
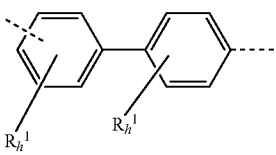
Formula (L¹-5)
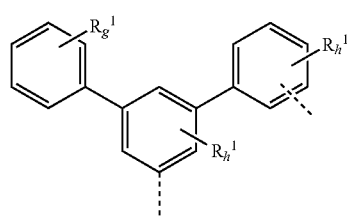
Formula (L¹-6)
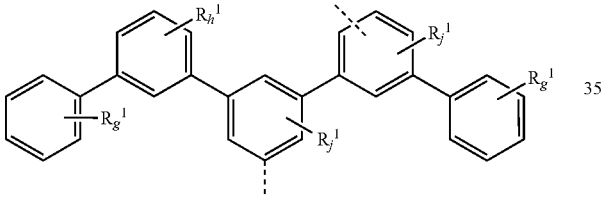
Formula (L¹-7)
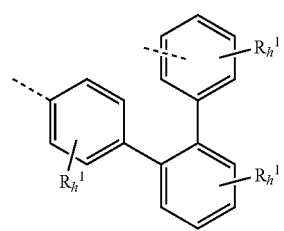
Formula (L¹-8)
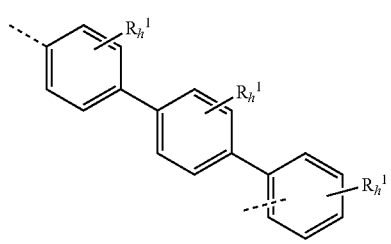
Formula (L¹-9)
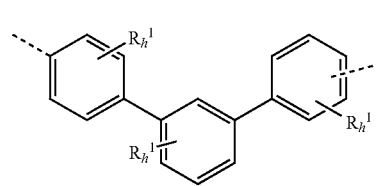
Formula (L¹-10)
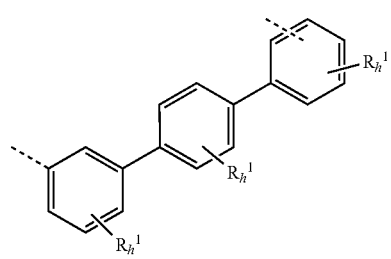
Formula (L¹-11)
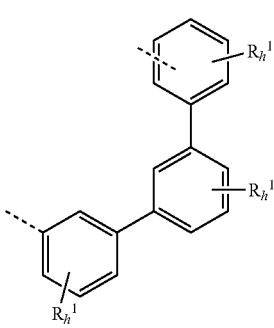
Formula (L¹-12)
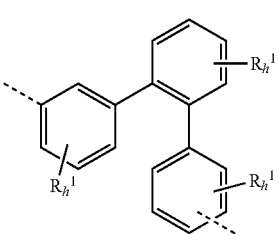
Formula (L¹-13)
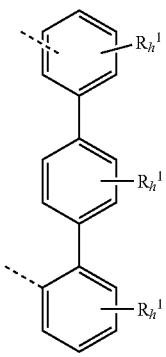
Formula (L¹-14)
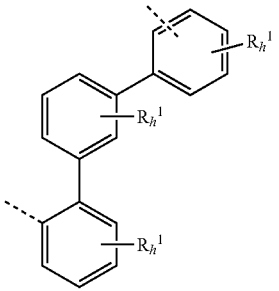

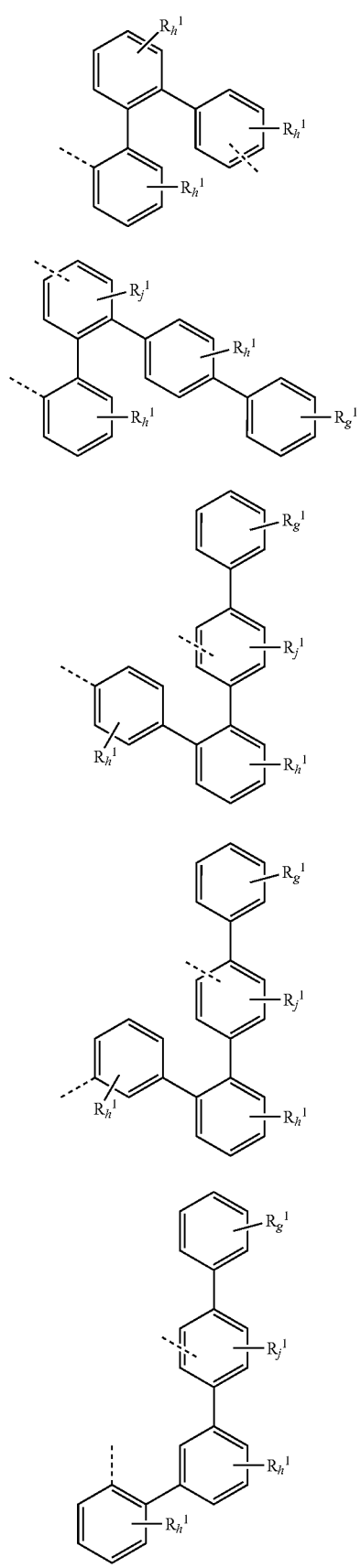
Formula (L¹-15)
Formula (L¹-16)
Formula (L¹-17)
Formula (L¹-18)
Formula (L¹-19)
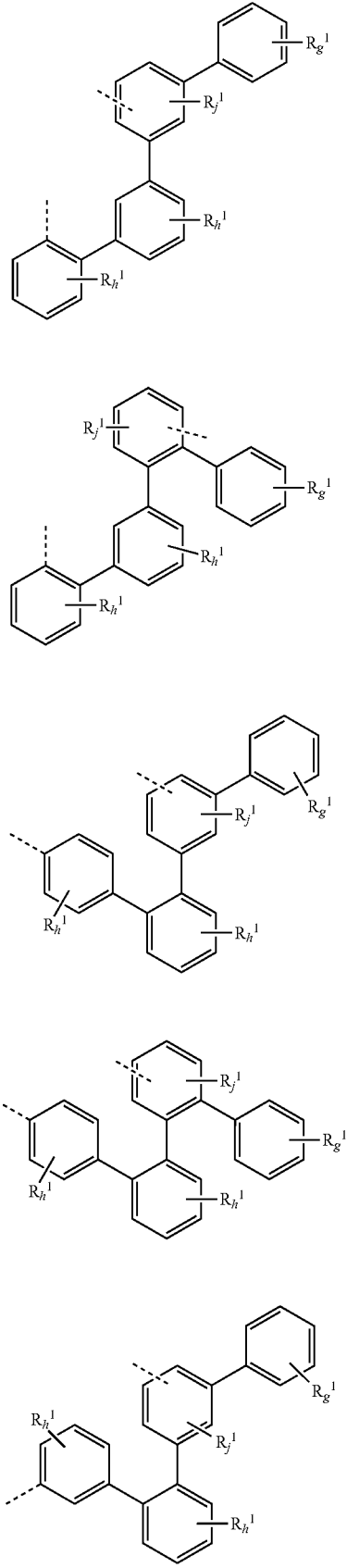
Formula (L¹-20)
Formula (L¹-21)
Formula (L¹-22)
Formula (L¹-23)
Formula (L¹-24)

Formula (L¹-25)
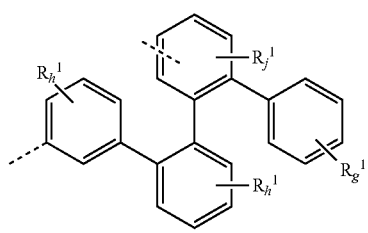
Formula (L¹-26)
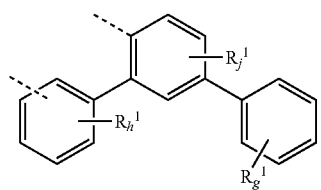
Formula (L¹-27)
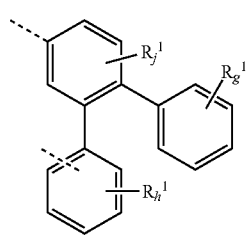
Formula (L¹-28)
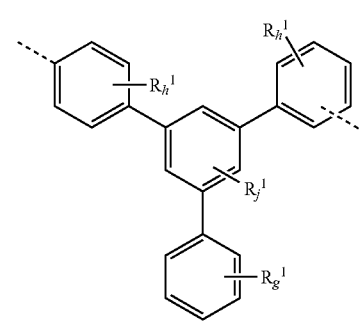
Formula (L¹-29)
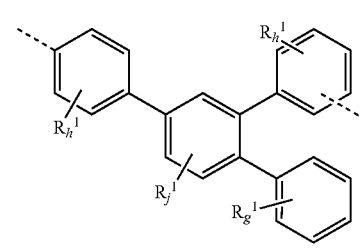
Formula (L¹-30)
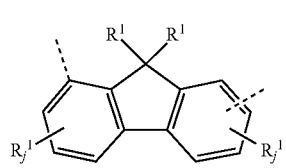
Formula (L¹-31)
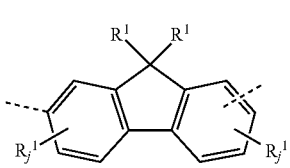
Formula (L¹-32)
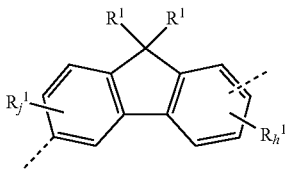
Formula (L¹-33)
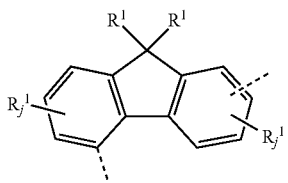
Formula (L¹-34)
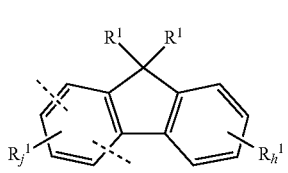
Formula (L¹-35)
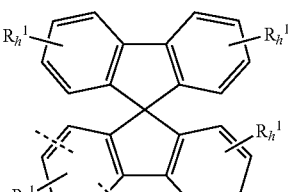
Formula (L¹-36)
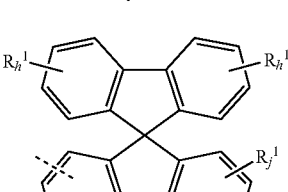
Formula (L¹-37)
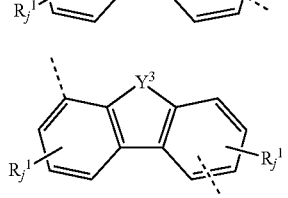
Formula (L¹-38)
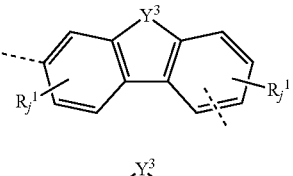
Formula (L¹-39)
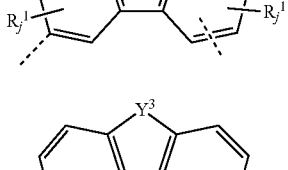
Formula (L¹-40)

Formula (L¹-41)
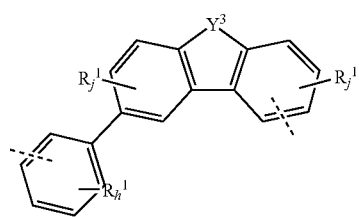
Formula (L¹-42)
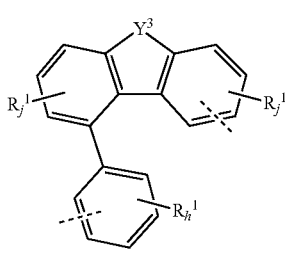
Formula (L¹-43)
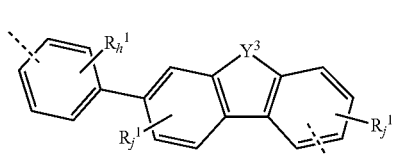
Formula (L¹-44)
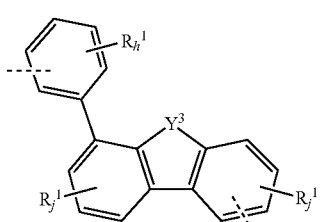
Formula (L¹-45)
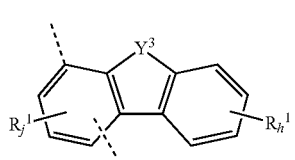
Formula (L¹-46)
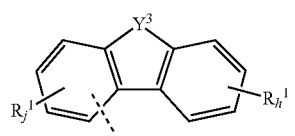
Formula (L¹-47)
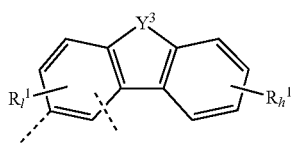
Formula (L¹-48)
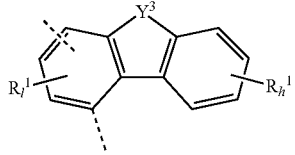
Formula (L¹-49)
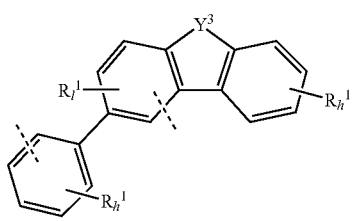
Formula (L¹-50)
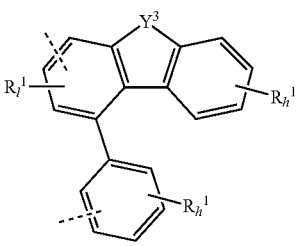
Formula (L¹-51)
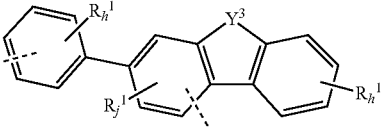
Formula (L¹-52)
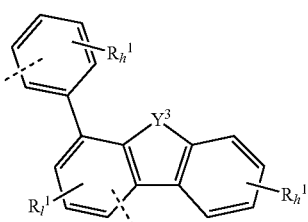
Formula (L¹-53)
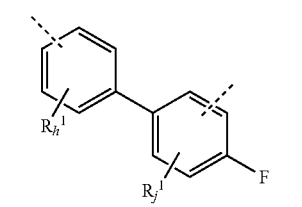
Formula (L¹-54)
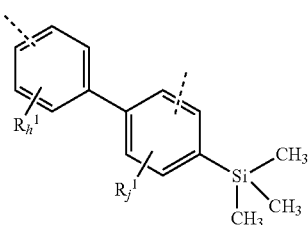
Formula (L¹-55)
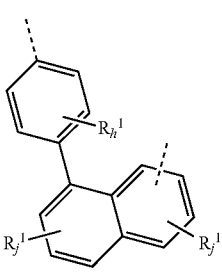

Formula (L¹-56)
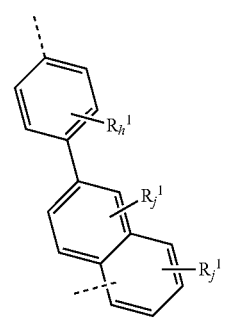
Formula (L¹-57)
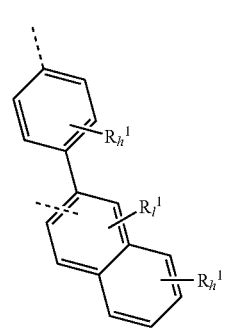
Formula (L¹-58)
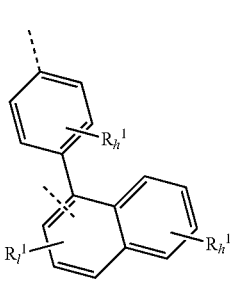
Formula (L¹-59)
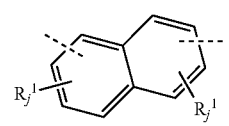
Formula (L¹-60)
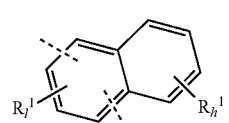
Formula (L¹-61)
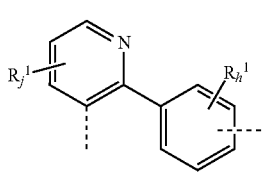
Formula (L¹-62)
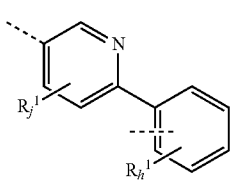
Formula (L¹-63)
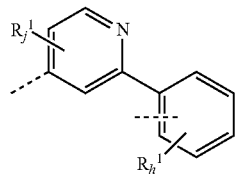
Formula (L¹-64)
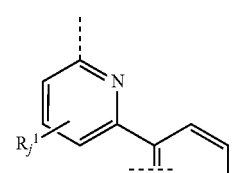
Formula (L¹-65)
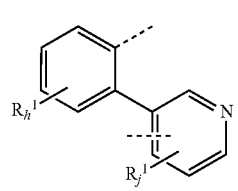
Formula (L¹-66)
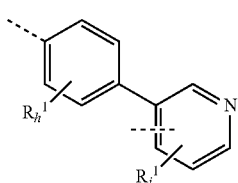
Formula (L¹-67)
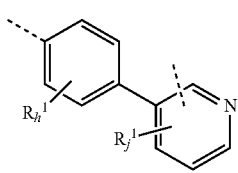
Formula (L¹-68)
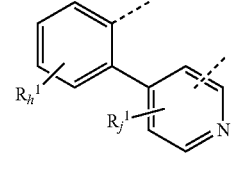
Formula (L¹-69)
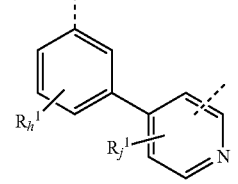
Formula (L¹-70)
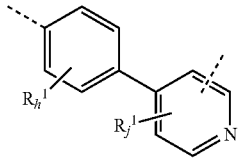

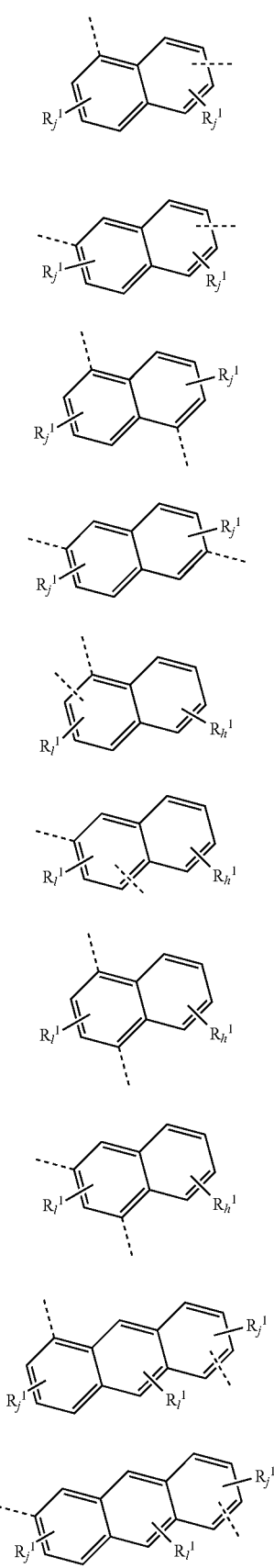
Formula (L¹-71)
Formula (L¹-72)
Formula (L¹-73)
Formula (L¹-74)
Formula (L¹-75)
Formula (L¹-76)
Formula (L¹-77)
Formula (L¹-78)
Formula (L¹-79)
Formula (L¹-80)
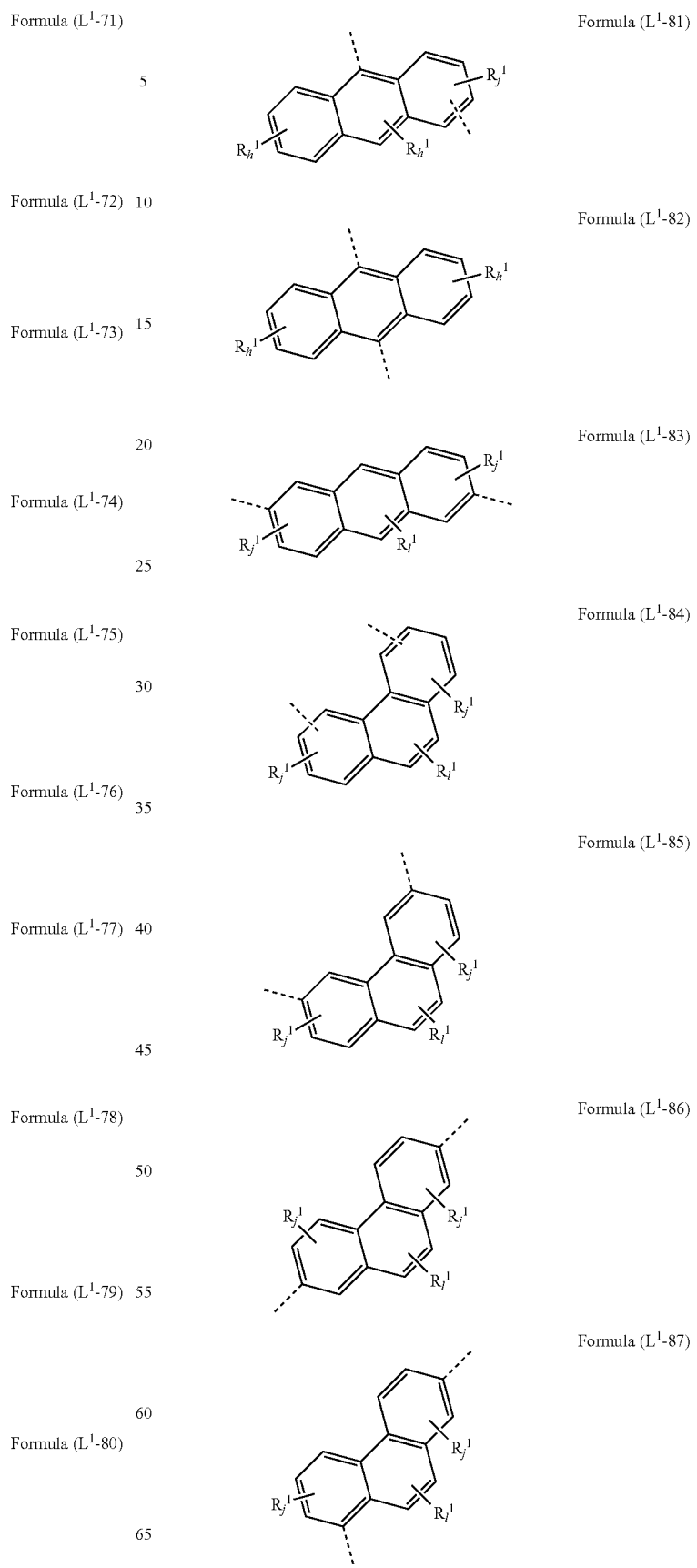
Formula (L¹-81)
Formula (L¹-82)
Formula (L¹-83)
Formula (L¹-84)
Formula (L¹-85)
Formula (L¹-86)
Formula (L¹-87)

Formula (L¹-88)
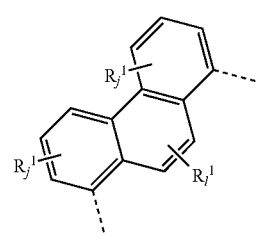
Formula (L¹-89)
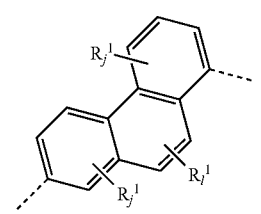
Formula (L¹-90)
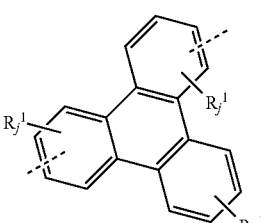
Formula (L¹-91)
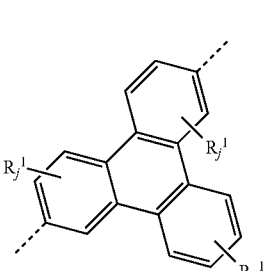
Formula (L¹-92)
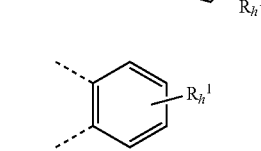
Formula (L¹-93)
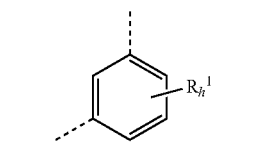
Formula (L¹-94)
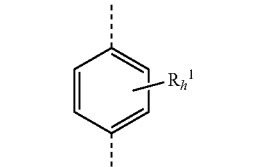
Formula (L¹-95)
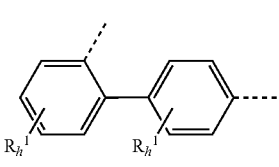
Formula (L¹-96)
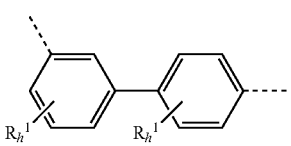
Formula (L¹-97)
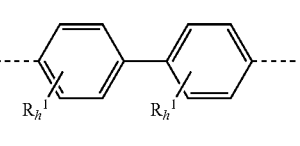
Formula (L¹-98)
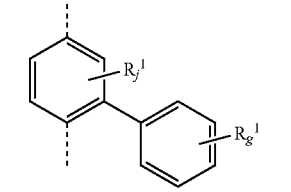
Formula (L¹-99)
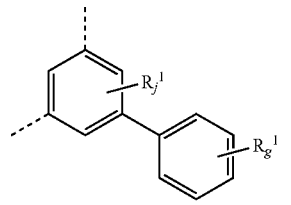
Formula (L¹-100)
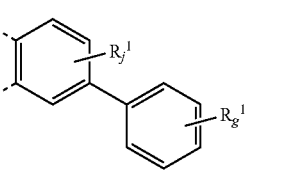
Formula (L¹-101)
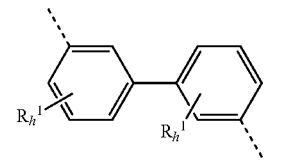
Formula (L¹-102)
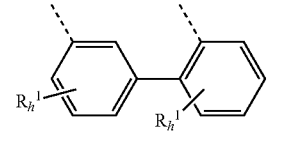
Formula (L¹-103)
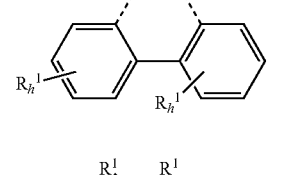
Formula (L¹-104)
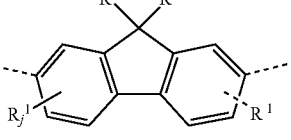

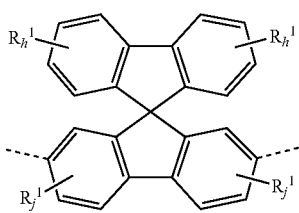

Formula (L¹-105)

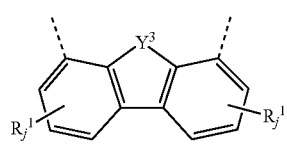

Formula (L¹-106)

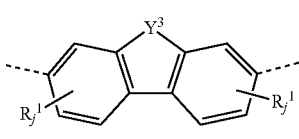

Formula (L¹-107)

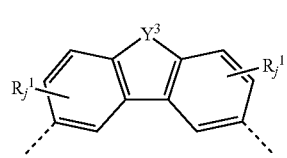

Formula (L¹-108)

where the dotted bonds in each case mark the positions of attachment, the index k is 0 or 1, the index I is 0, 1 or 2, the index j at each instance is independently 0, 1, 2 or 3, the index h at each instance is independently 0, 1, 2, 3 or 4, the index g is 0, 1, 2, 3, 4 or 5; the symbol $Y^3$ is O, S or $NR^1$, preferably O or S; and the symbol $R^1$ has the definition given above, especially for formula (I).

It may preferably be the case that the sum total of the indices k, l, g, h and j in the structures of the formula (L¹-1) to (L¹-108) is at most 3 in each case, preferably at most 2 and more preferably at most 1.

Preferred compounds of the invention having a group of the formulae (H-1) to (H-26) comprise an $Ar^2$ group selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferred compounds of the invention having a group of the formula (QL) comprise an $L^1$ group which represents a bond or which is selected from one of the formulae (L¹-1) to (L¹-78) and/or (L¹-92) to (L¹-108), preferably of the formula (L¹-1) to (L¹¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferably, the $R^1$ radicals in the formulae (L¹-1) to (L¹-108) do not form a fused aromatic or heteroaromatic ring system, and preferably do not form any fused ring system, with the ring atoms of the aryl group or heteroaryl group to which the $R^1$ radicals are bonded. This includes the formation of a fused ring system with possible substituents $R^2$ and $R^3$ which may be bonded to the $R^1$ or $R^2$ radicals.

When the compound of the invention is substituted by aromatic or heteroaromatic $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

In a further preferred embodiment of the invention, $R^2$, for example in a structure of formula (I) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Preferably, the $R^2$ radicals do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

In a further preferred embodiment of the invention, $R^3$, for example in a structure of formula (I) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Examples of suitable compounds of the invention are the structures of the following formulae 1 to 102 shown below:

-continued
Formula 1
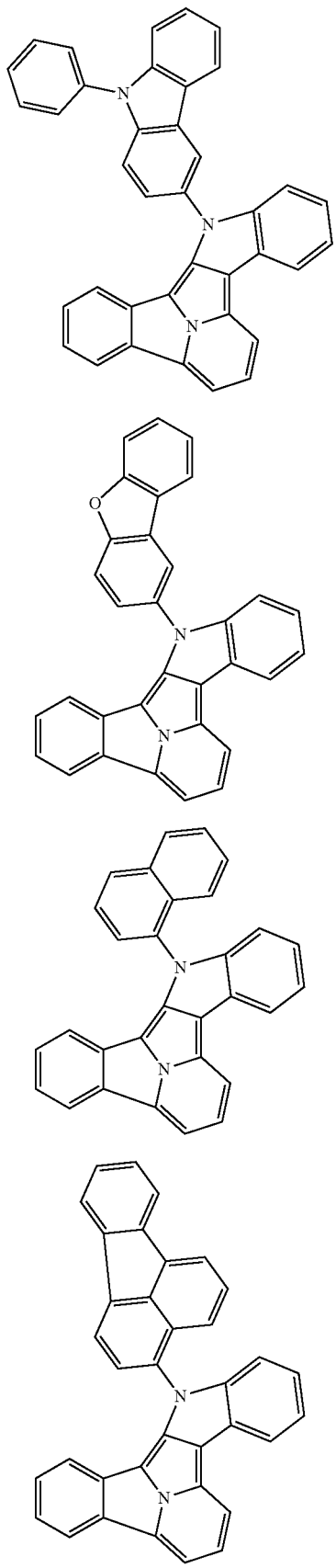
Formula 2
Formula 3
Formula 4
Formula 5
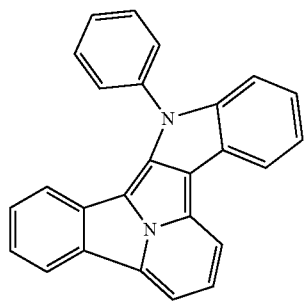
Formula 6
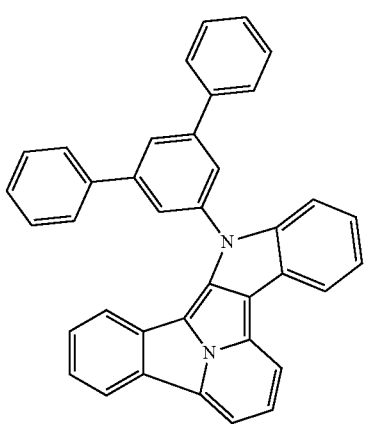
Formula 7
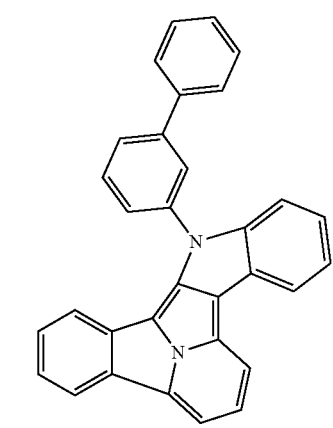
Formula 8
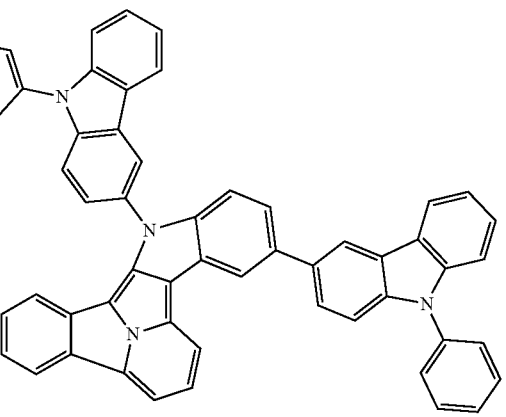

Formula 9
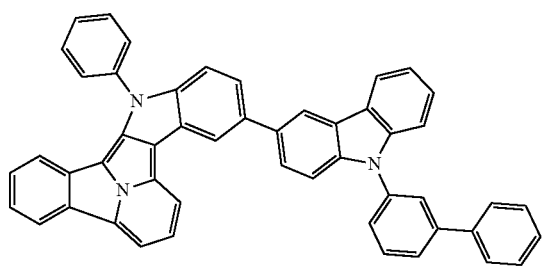
Formula 10
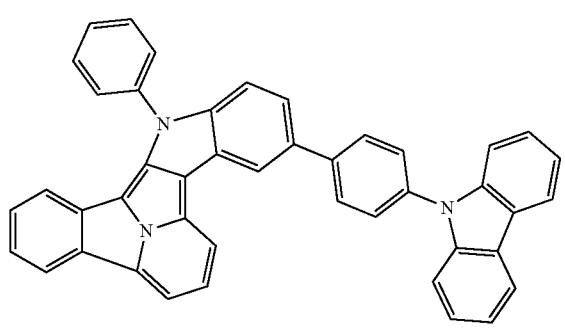
Formula 11
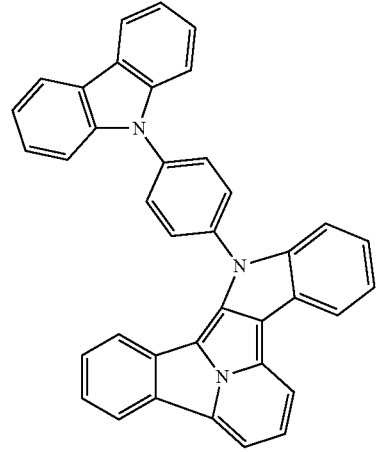
Formula 12
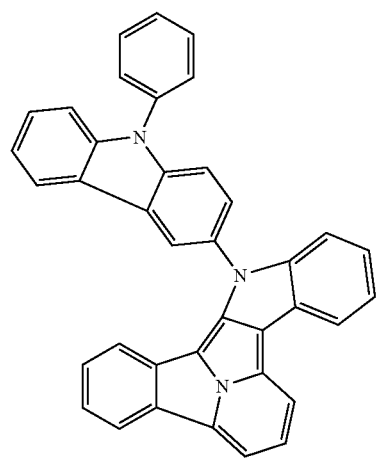
Formula 13
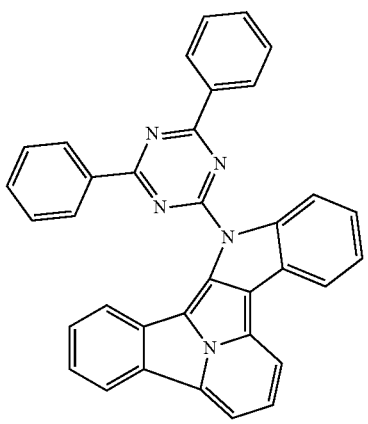
Formula 14
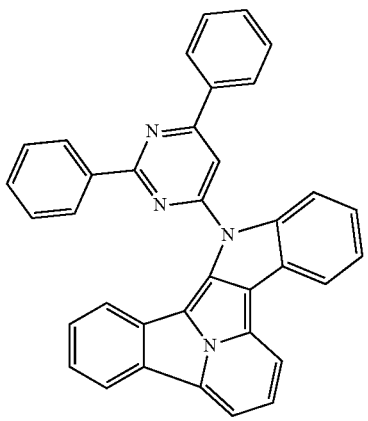
Formula 15
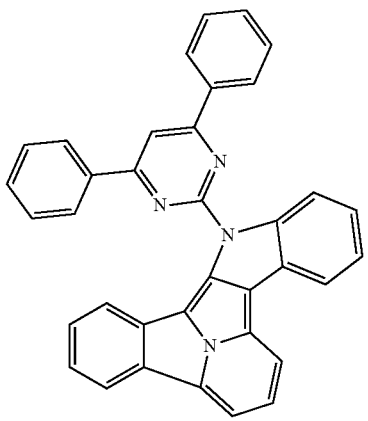

Formula 16
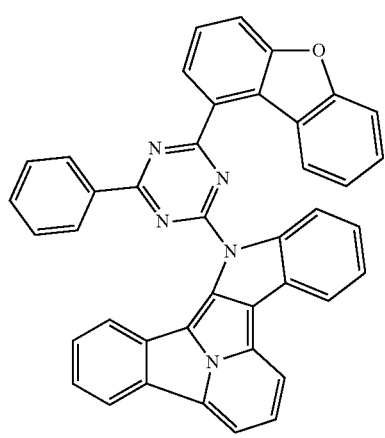
Formula 17
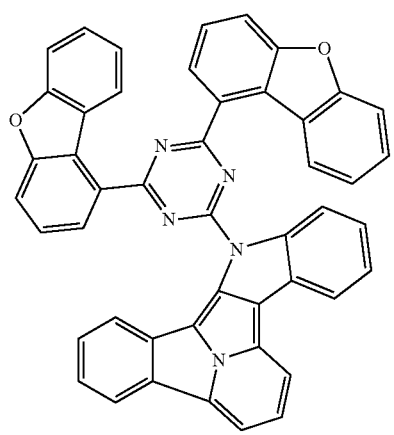
Formula 18
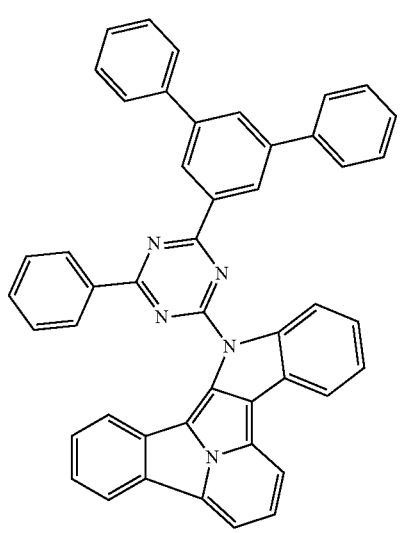
Formula 19
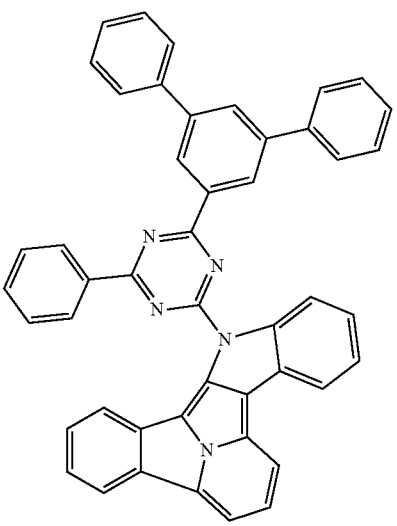
Formula 20
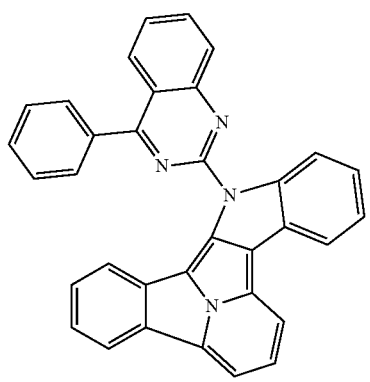
Formula 21
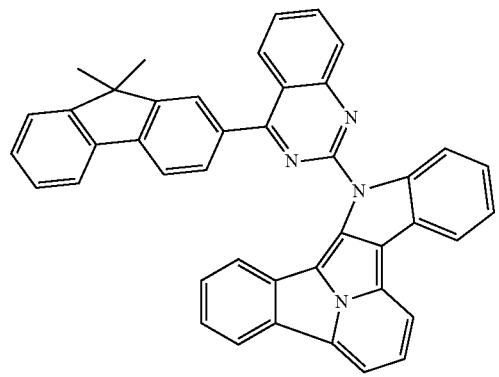

Formula 22
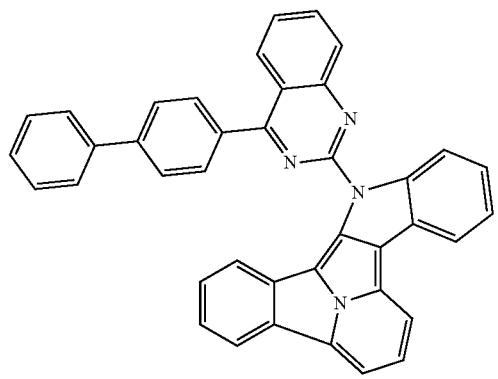
Formula 23
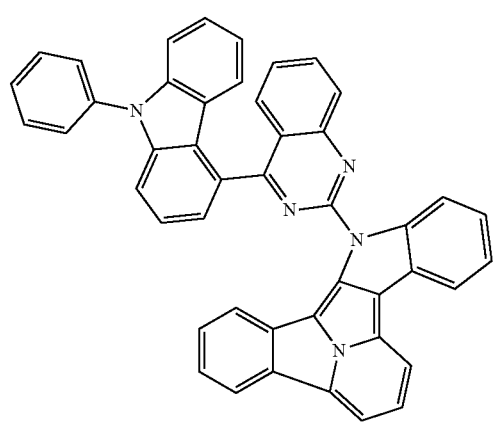
Formula 24
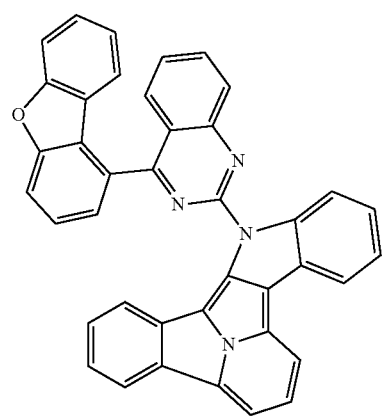
Formula 25
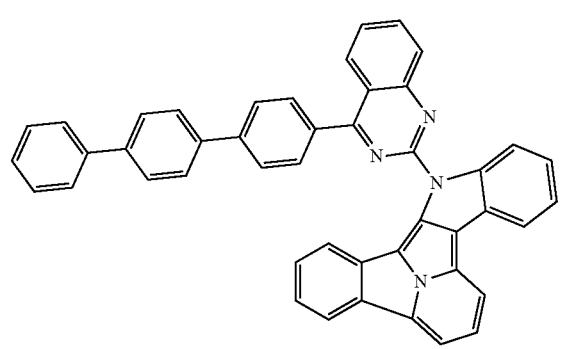
Formula 26
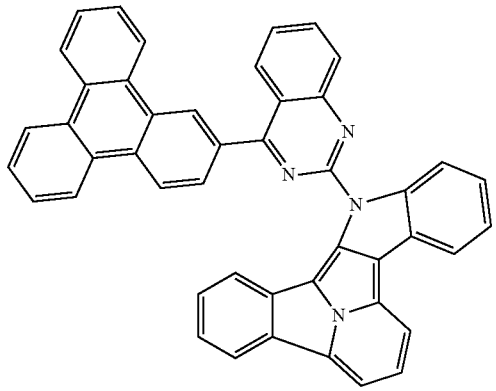
Formula 27
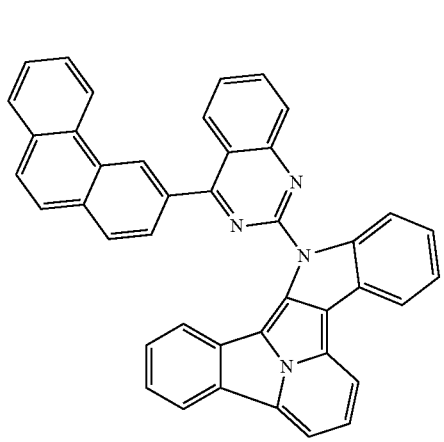
Formula 28
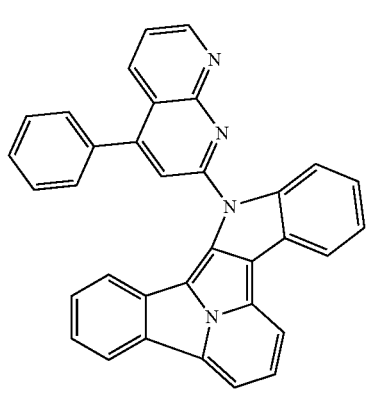
Formula 29
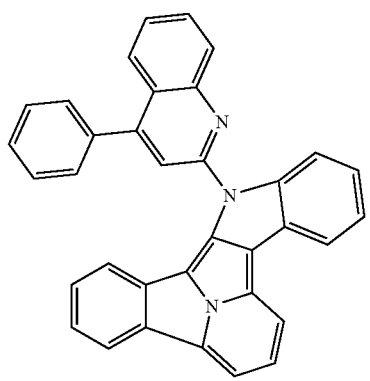

Formula 30
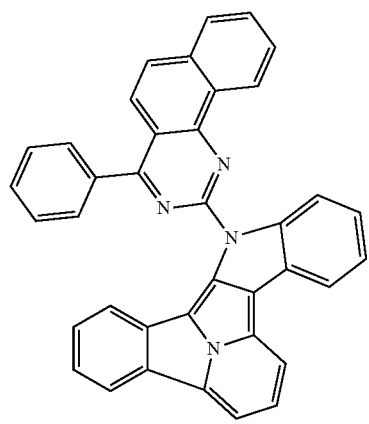
Formula 31
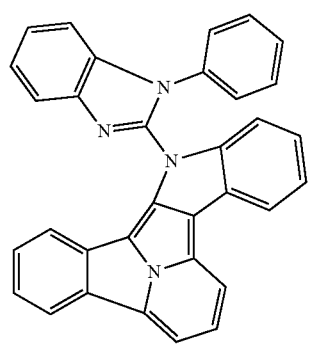
Formula 32
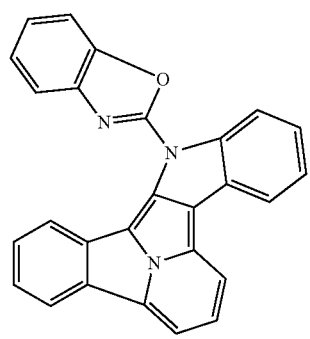
Formula 33
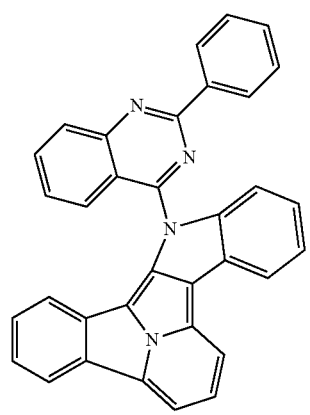
Formula 34
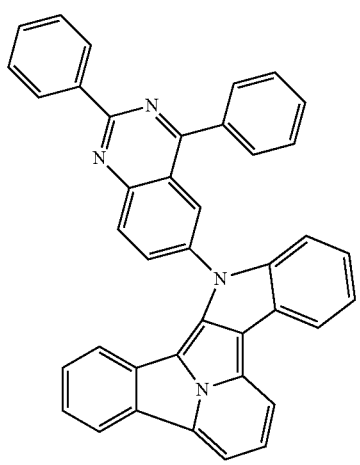
Formula 35
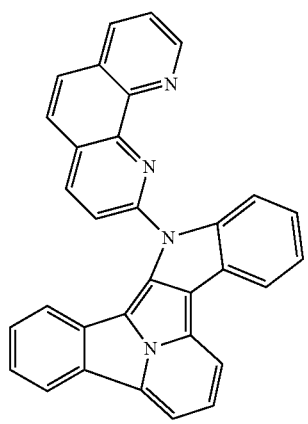
Formula 36
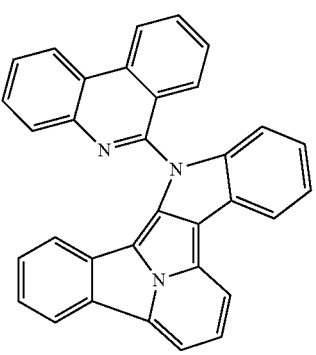
Formula 37
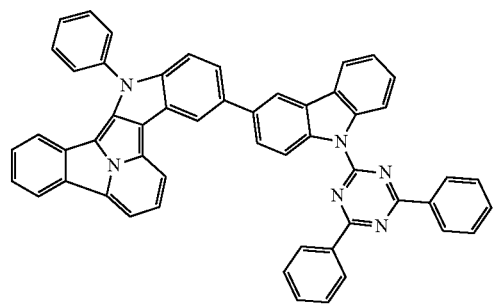

Formula 38
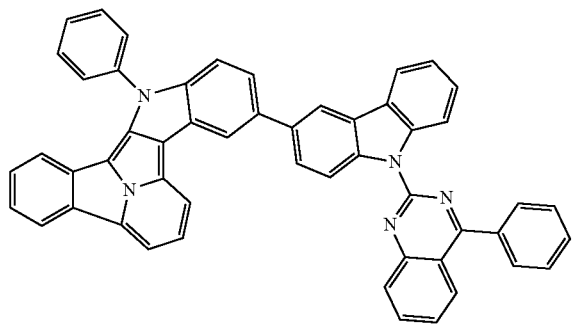
Formula 39
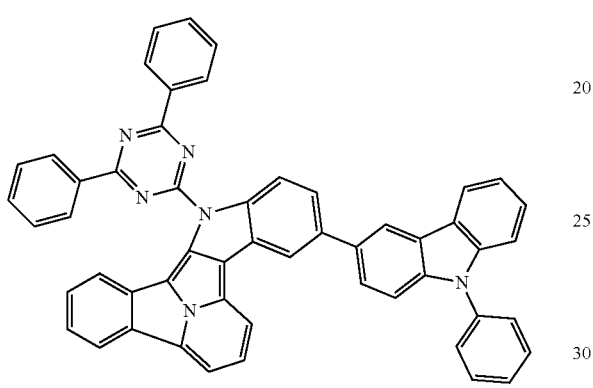
Formula 40
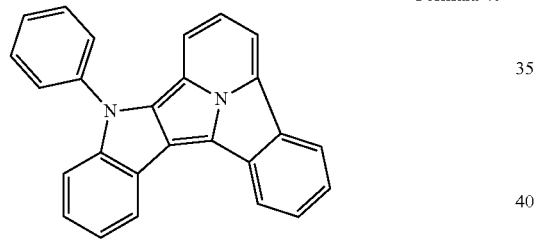
Formula 41
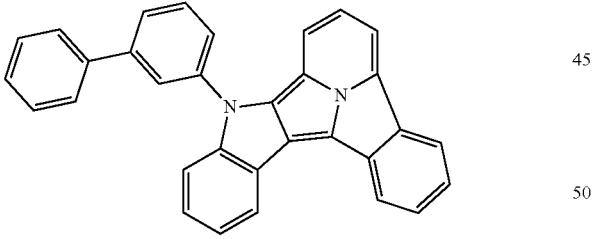
Formula 42
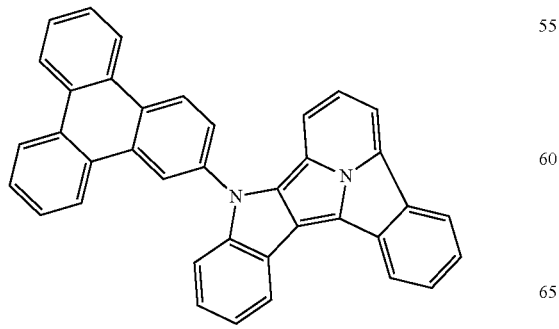
Formula 43
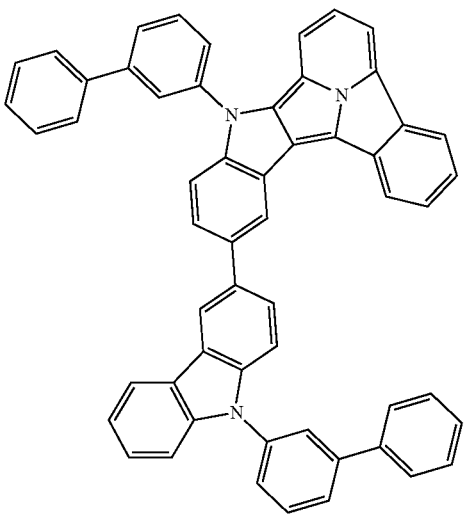
Formula 44
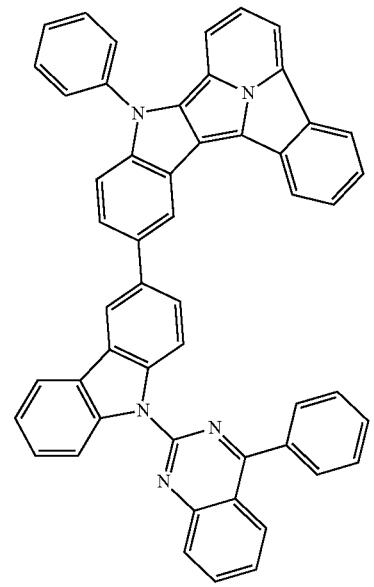

-continued
Formula 45
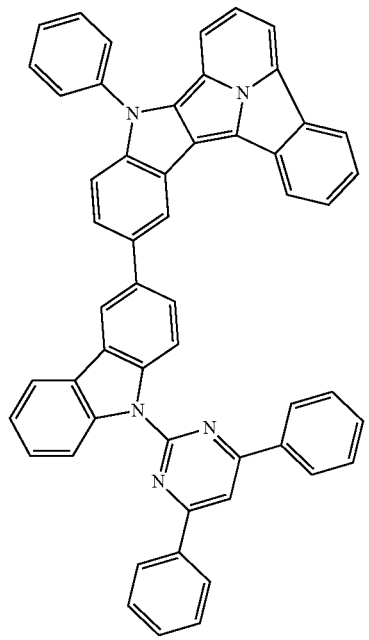
Formula 46
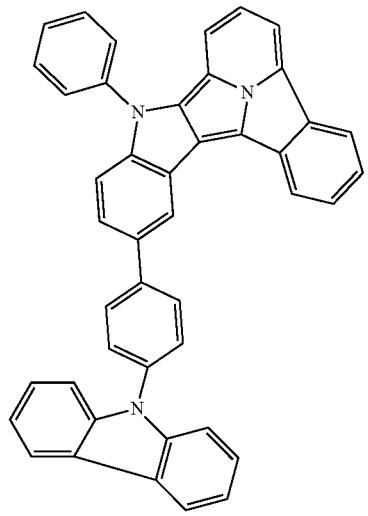
Formula 47
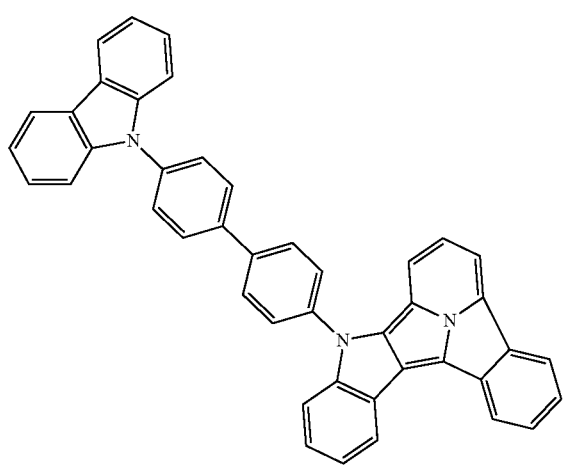
Formula 48
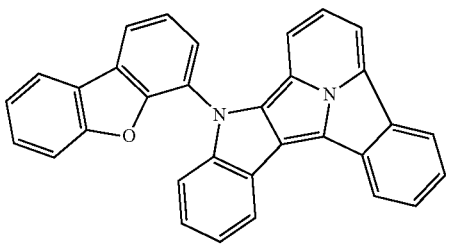
Formula 49
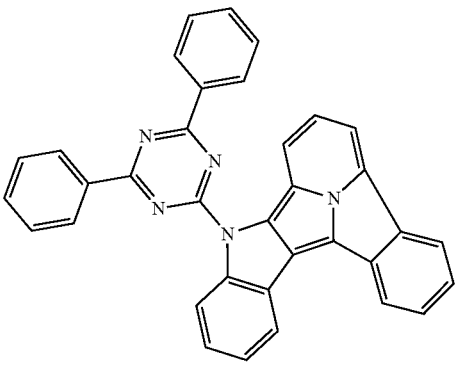
Formula 50
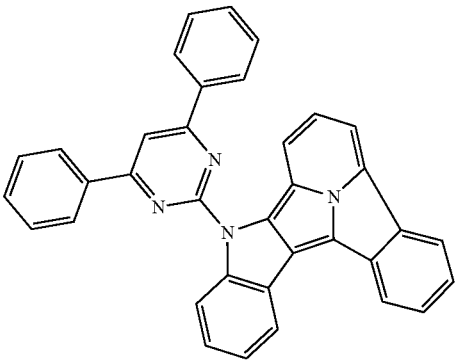
formula 51
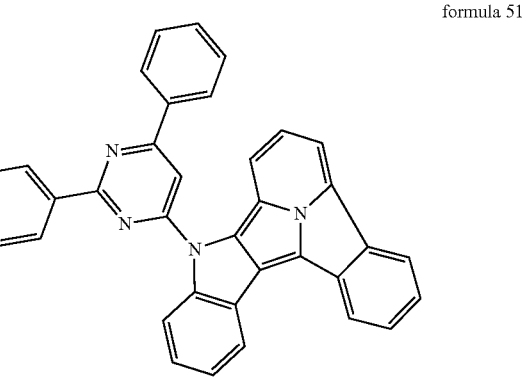

Formula 52
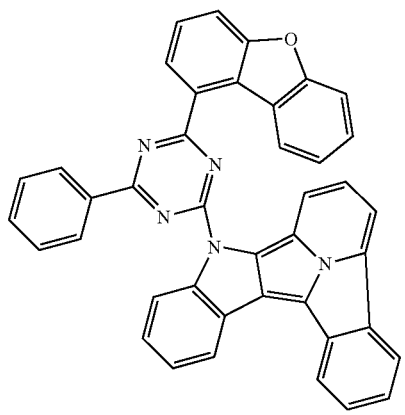
Formula 53
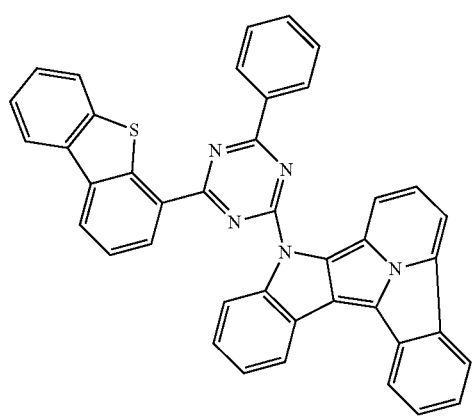
Formula 54
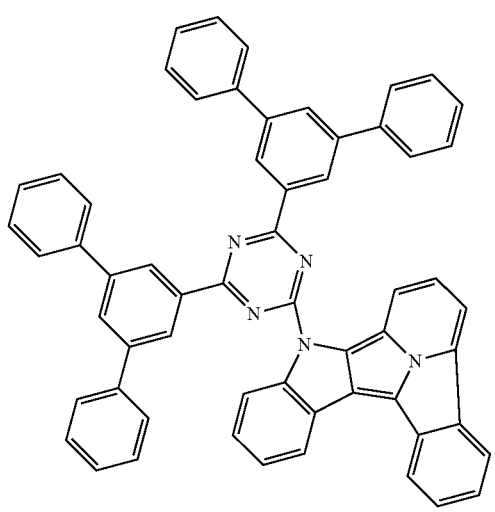
Formula 55
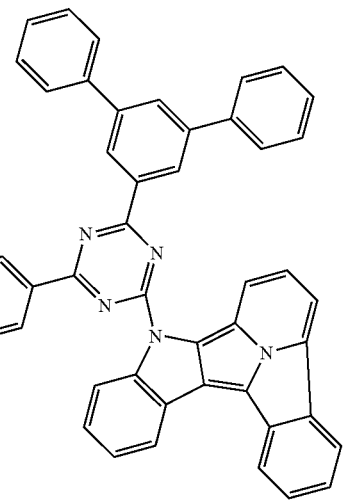
Formula 56
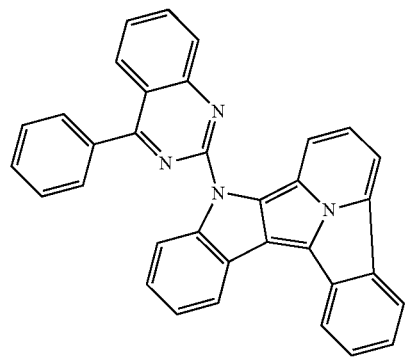
Formula 57
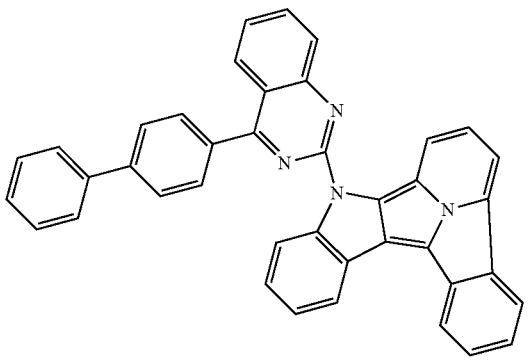

Formula 58
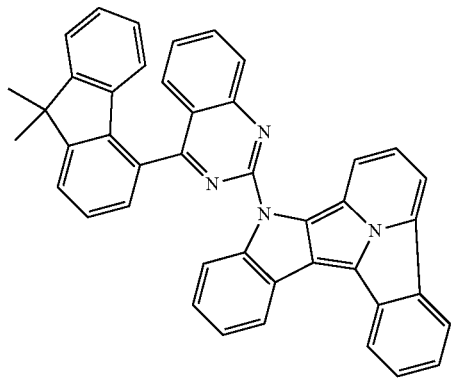
Formula 62
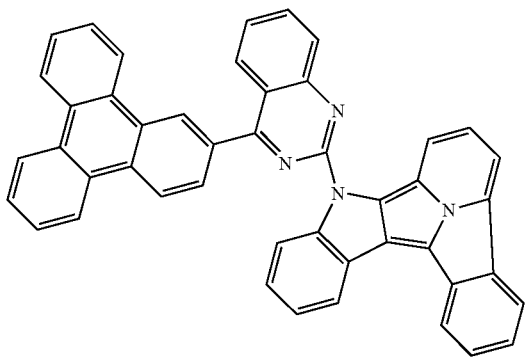
Formula 59
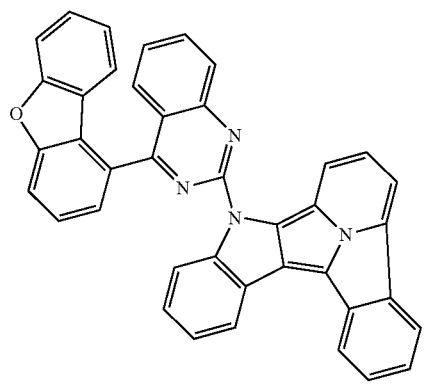
Formula 63
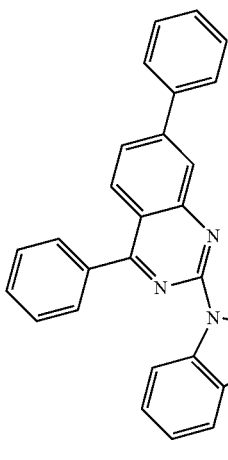
Formula 60
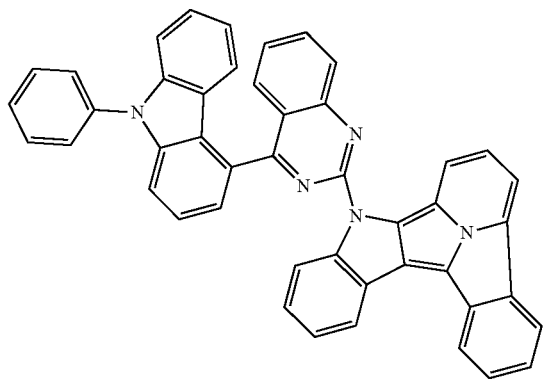
Formula 64
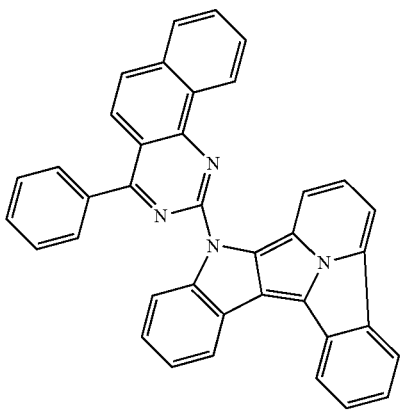
Formula 61
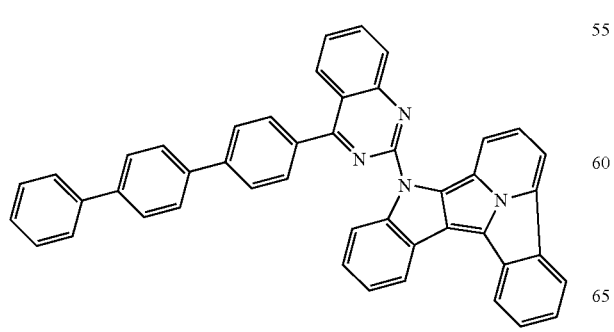
Formula 65
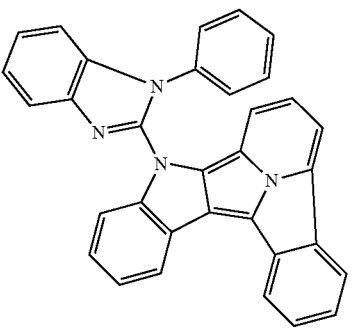

Formula 66
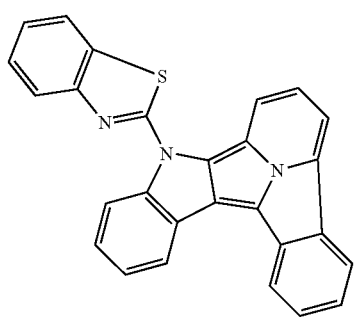
Formula 67
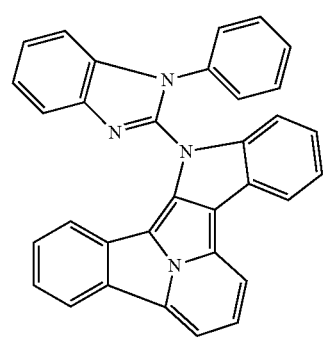
Formula 68
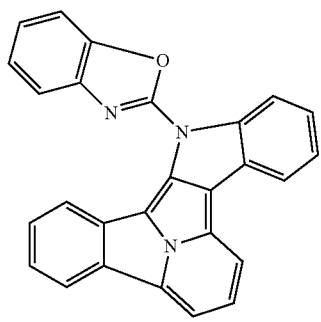
Formula 69
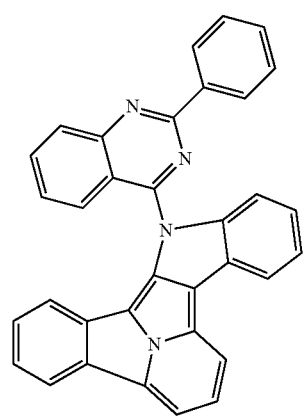
Formula 70
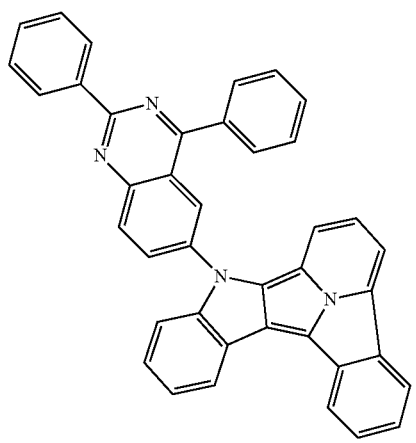
Formula 71
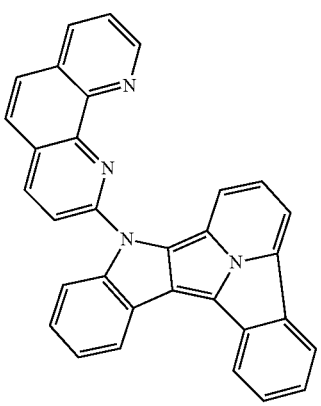
Formula 72
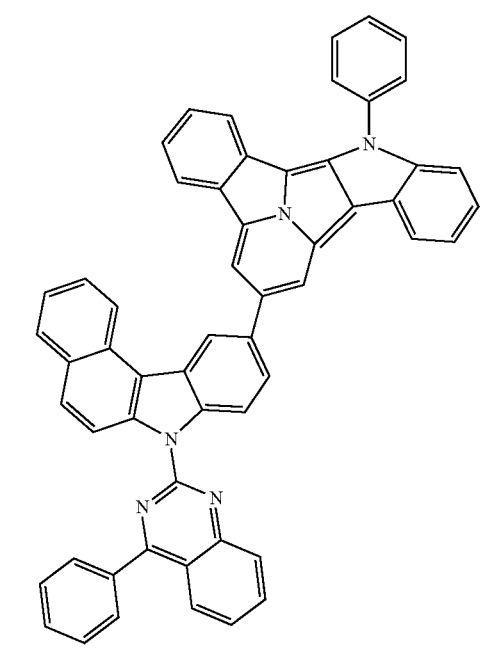

Formula 73
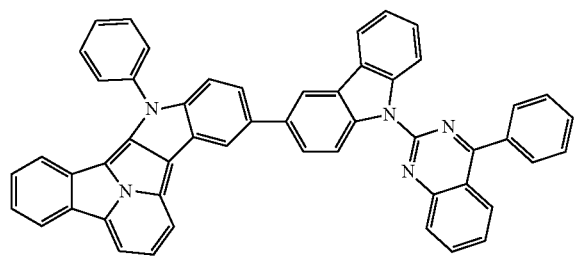
Formula 74
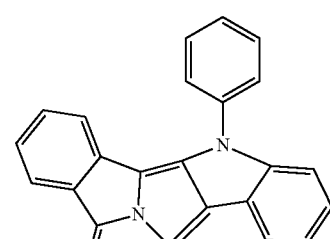
Formula 75
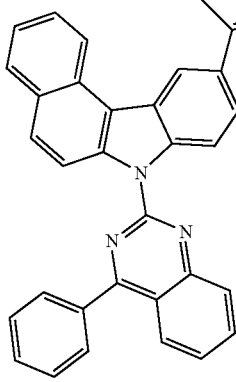
Formula 76
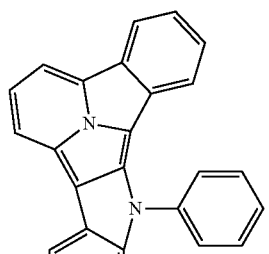
Formula 77
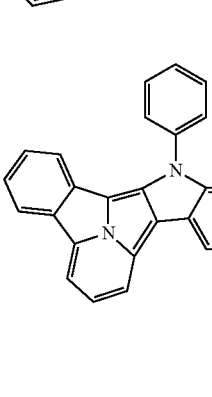
Formula 78
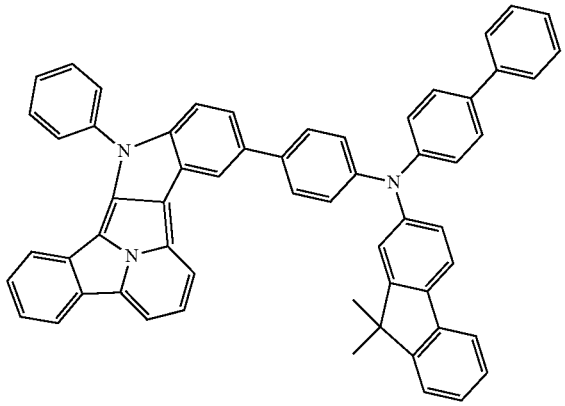

Formula 79
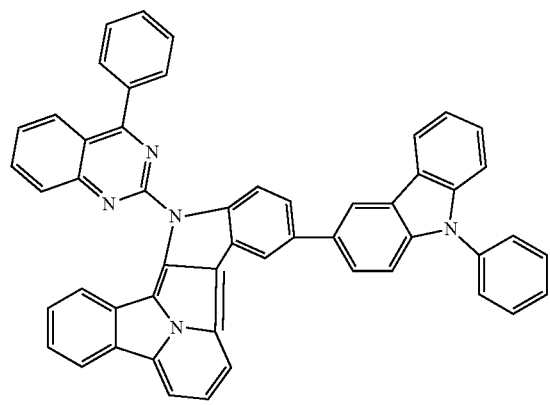
Formula 80
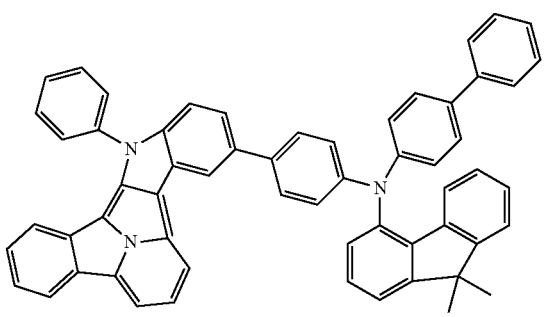
Formula 81
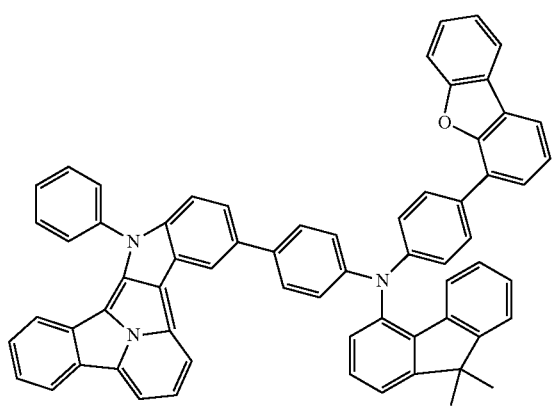
Formula 82
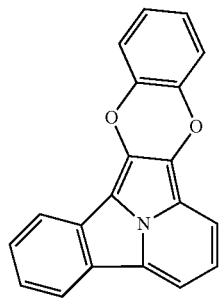
Formula 83
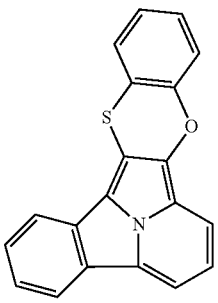
Formula 84
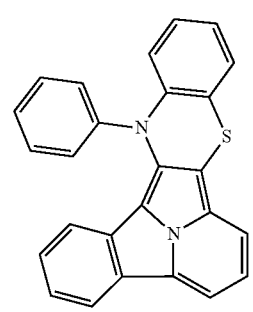
Formula 85
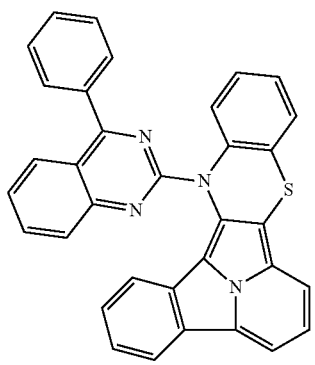
Formula 86
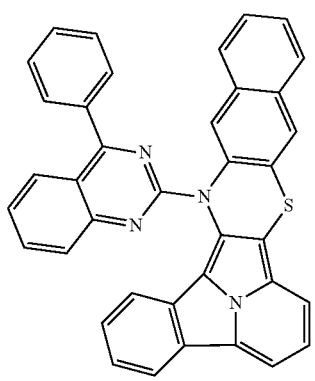

Formula 87
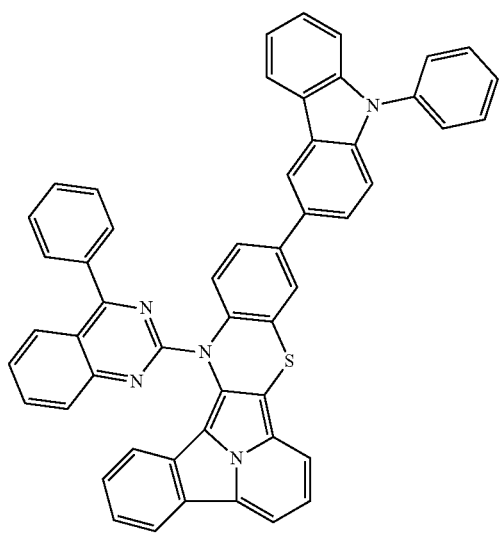
Formula 88
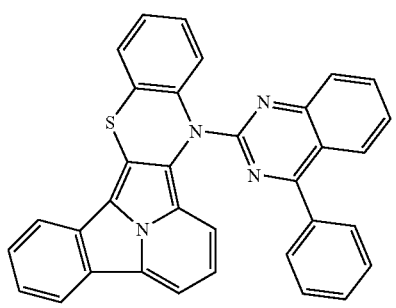
Formula 89
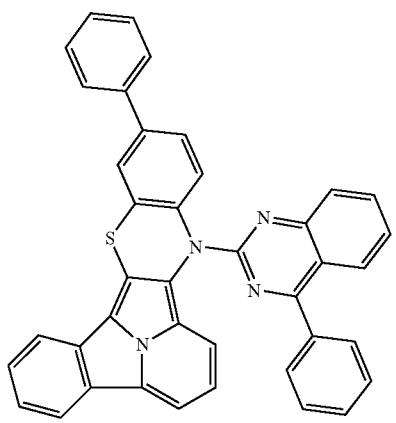
Formula 90
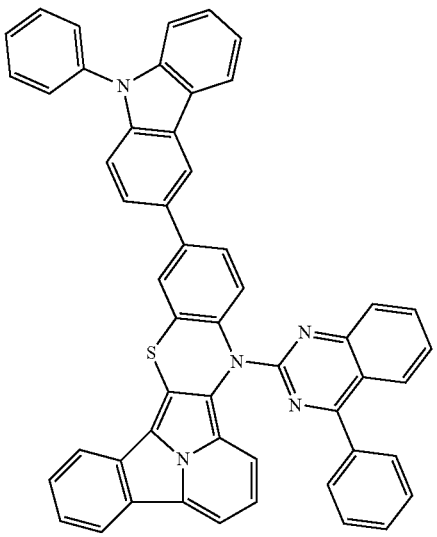
Formula 91
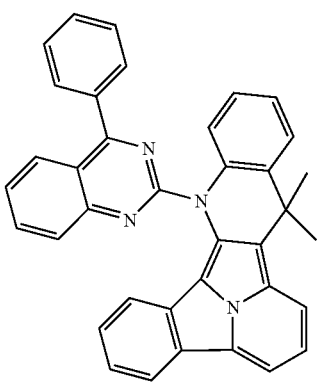
Formula 92
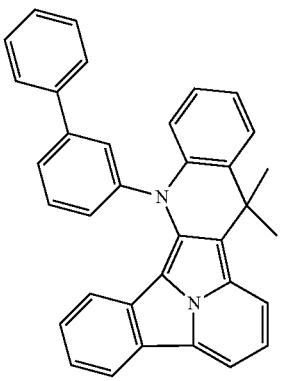

Formula 93
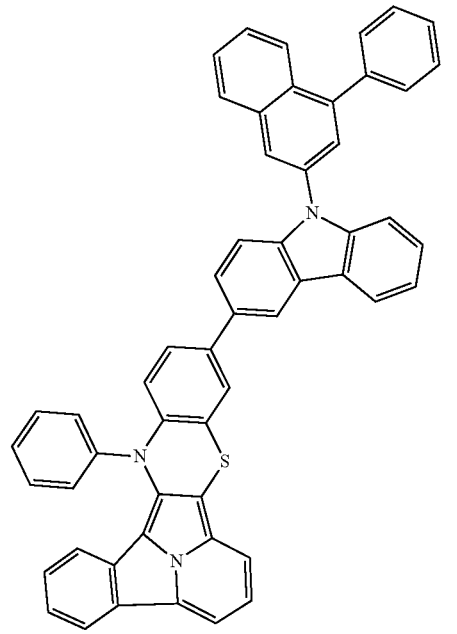
Formula 94
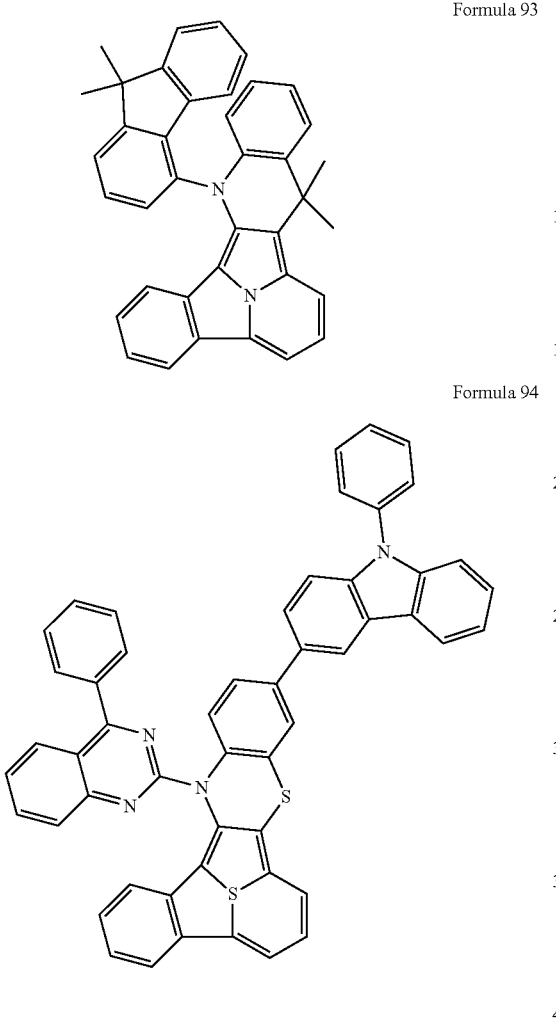
Formula 95
Formula 96
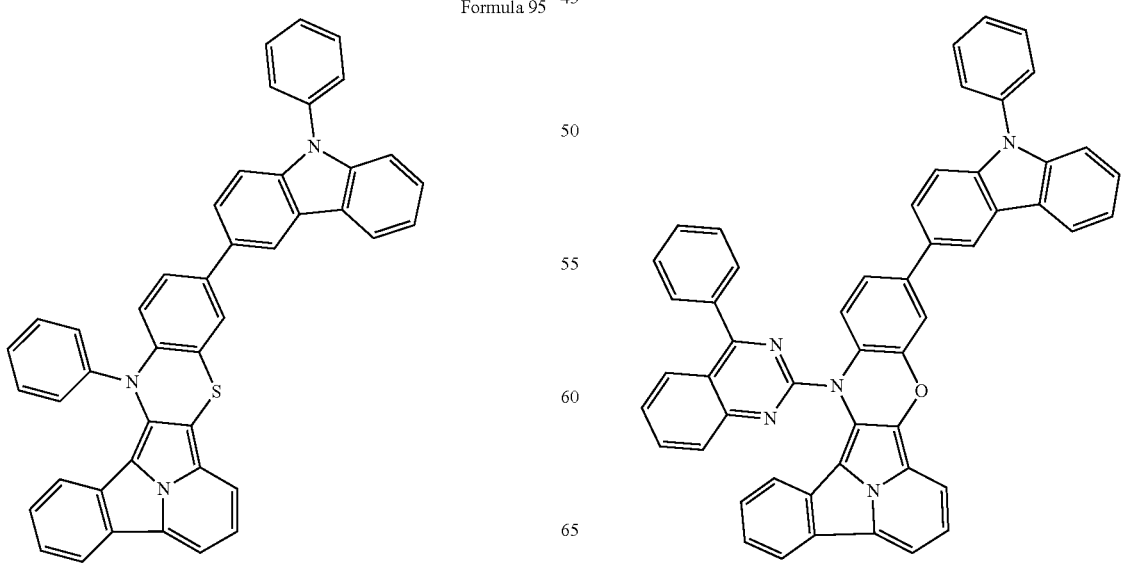
Formula 97

Formula 98

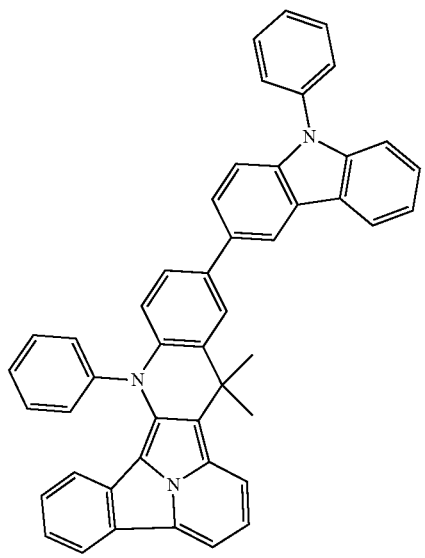

Formula 99

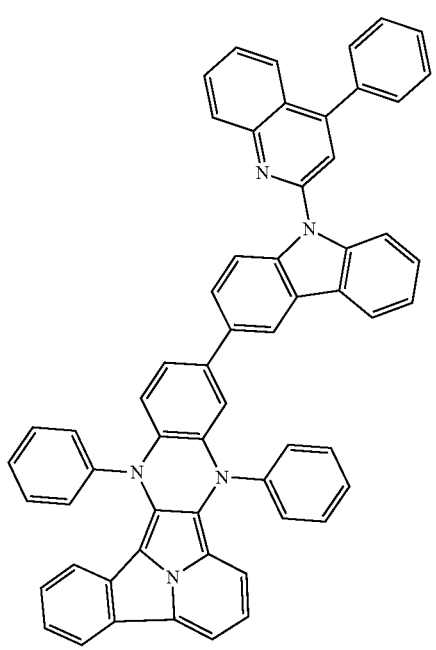

Formula 100

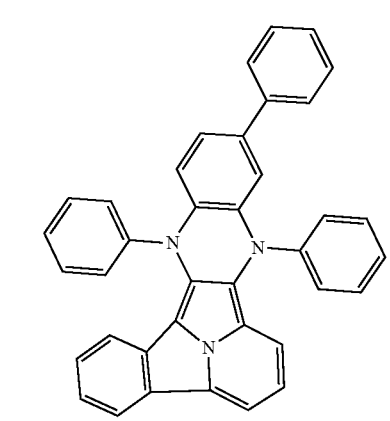

Formula 101

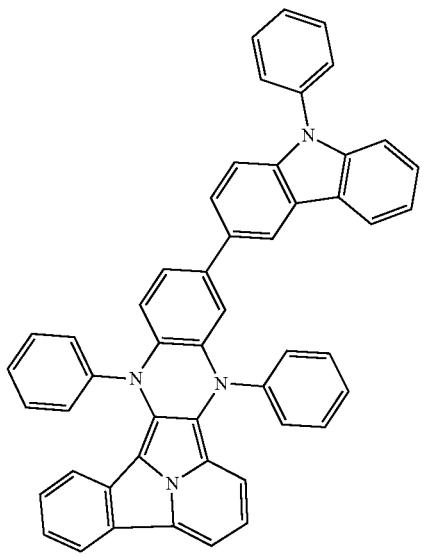

Formula 102

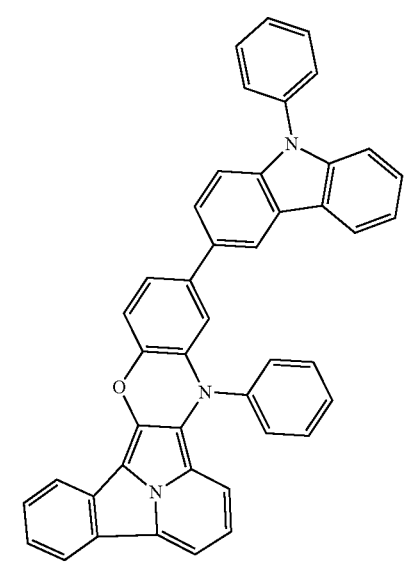

Preferred embodiments of compounds of the invention are recited specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (I) in which, in a coupling reaction, a compound comprising at least one nitrogen-containing heterocyclic group is joined to a compound comprising at least one aromatic or heteroaromatic group.

Suitable indolizines are in many cases commercially available, and the starting compounds detailed in the examples are obtainable by known processes, and so reference is made thereto.

These compounds can be reacted with further aryl compounds by known coupling reactions, the necessary conditions for this purpose being known to the person skilled in the art, and detailed specifications in the examples give support to the person skilled in the art in conducting these reactions. Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

Scheme 1 a)

b)

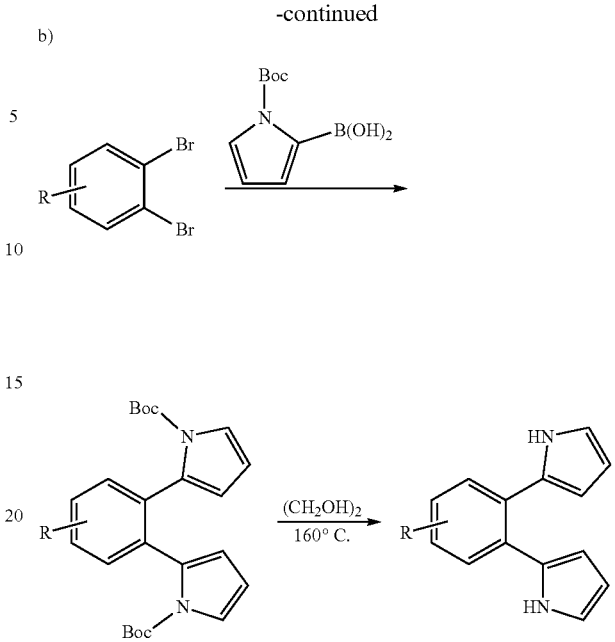

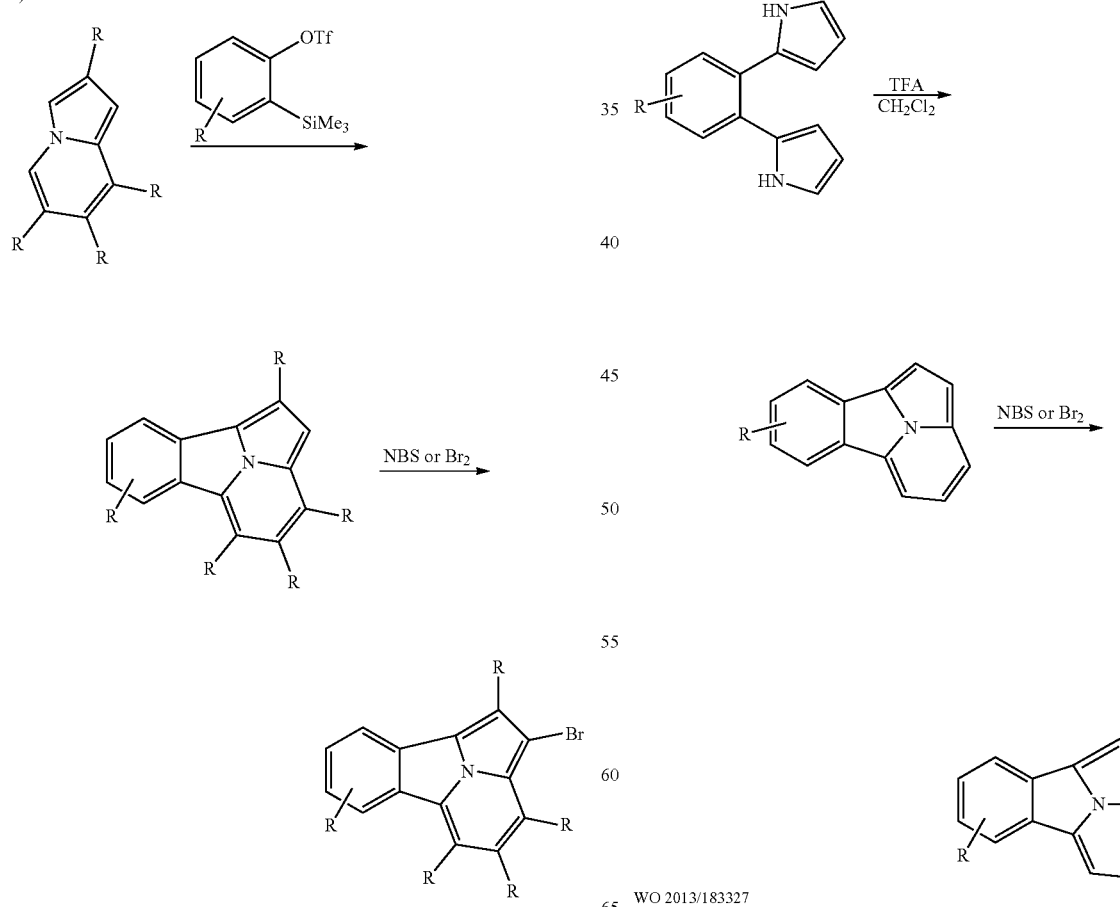

Eur. J. Org. Chem. 2007, 3718-3726

WO 2013/183327

Scheme 2
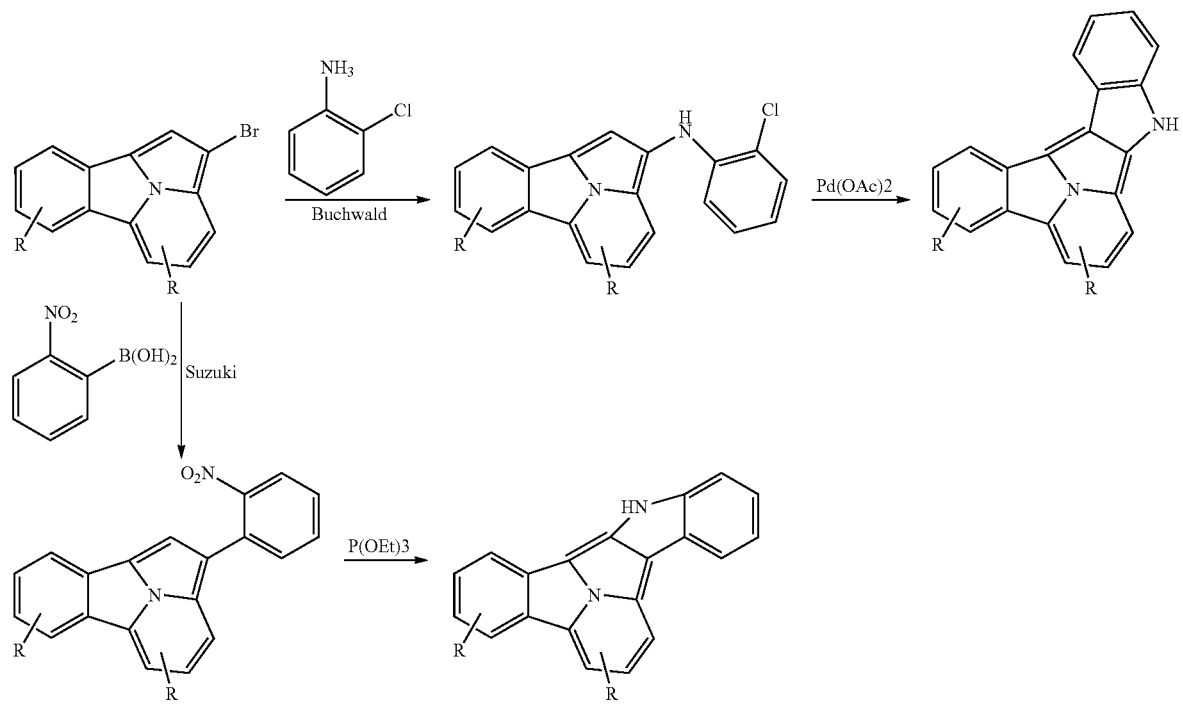
Scheme 3
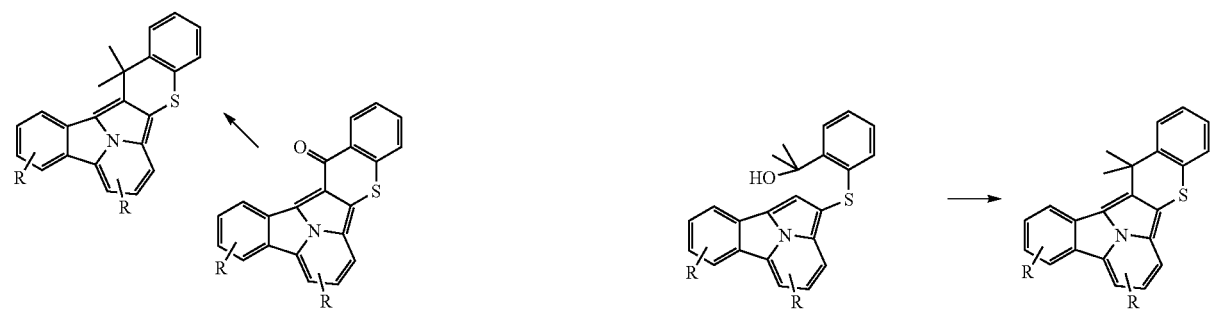
WO 2016149975
Organic and Bio-Organic Chemistry (1972-1999). (5), 1209-17; 1988
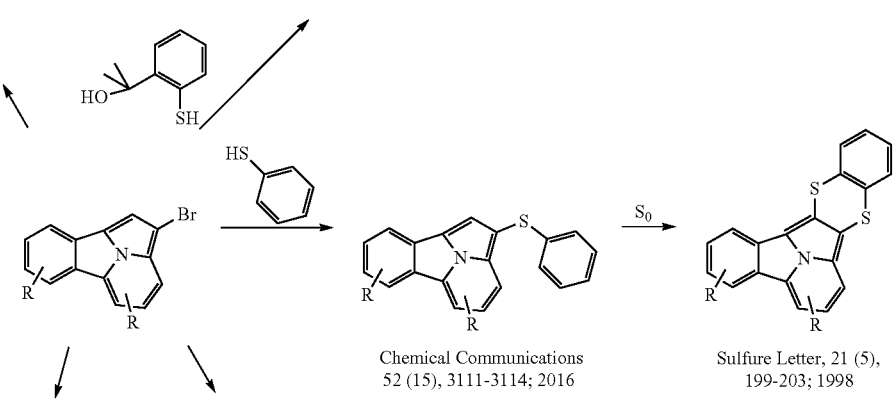
Chemical Communications 52 (15), 3111-3114; 2016
Sulfure Letter, 21 (5), 199-203; 1998

-continued

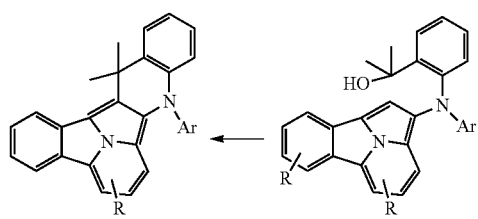

KR 2014070450

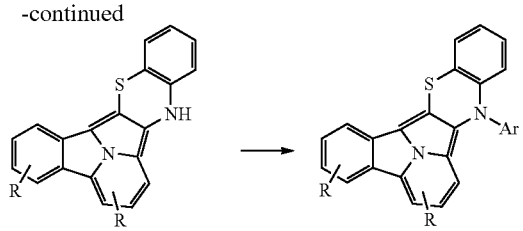

Bioorganic & Medicina
Chemistry Letters, 17 (11),
3014-3017: 2007

The definition of the symbols used in schemes 1, 2 and 3 corresponds essentially to those defined for formula (I), dispensing with numbering for reasons of clarity. In addition, there are literature references relating to further details of the reactions shown in schematic form.

In relation to the publications WO 2016/149975; Organic and Bio-Organic Chemistry, (1972-1999), (5), 1209-17, 1988; Sulfur Letters, 21(5), 199-203; 1998, Bioorganic & Medicinal Chemistry Letters, 17(11), 3014-3017, 2007; and KR 20140070450, it should be stated that these documents do not describe any compounds having an indolizine structure, but instead set out the reactions described in detail above on other aromatic or heteroaromatic compounds.

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, such that the compounds are soluble at room temperature in toluene or xylene, for example, in sufficient concentration to be able to process the compounds from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) or compounds of the invention, wherein there are one or more bonds of the compounds of the invention or of the structures of the formula (I) to the polymer, oligomer or dendrimer. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, for example a fluorescent dopant, a phosphorescent dopant or a compound that exhibits TADF (thermally activated delayed fluorescence), especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), matrix materials, electron transport materials, electron injection materials, hole conductor materials, hole injection materials, electron blocker materials, hole blocker materials, exciton blocker materials, wide band gap materials and n-dopants.

The present invention therefore also relates to a composition comprising at least one compound comprising structures of formula (I) or the preferred embodiments recited above and hereinafter and at least one further matrix material. According to a particular aspect of the present invention, the further matrix material has hole-transporting properties.

The present invention further provides a composition comprising at least one compound comprising at least one structure of formula (I) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state Ti and that of the lowest excited singlet state S1 of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((*HEh*\*27.212)−0.9899)/1.1206

LUMO(eV)=((*LEh*\*27.212)−2.0041)/1.385

These values are to be regarded as HOMO and LUMO energy levels of the materials in the context of this application.

The lowest triplet state Ti is defined as the energy of the triplet state having the lowest energy, which is apparent from the quantum-chemical calculation described.

The lowest excited singlet state S1 is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) or the preferred embodiments recited above and hereinafter and at least one phosphorescent emitter, the term "phosphorescent emitters" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and the as yet unpublished application EP 16186313.9. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

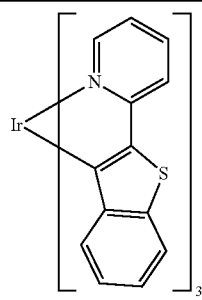

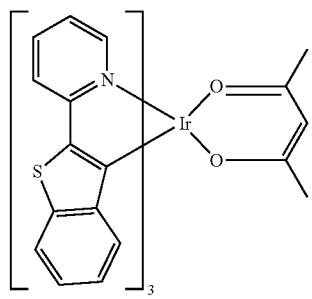

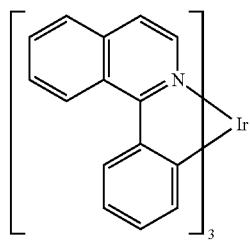

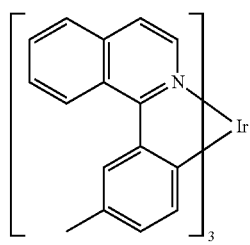

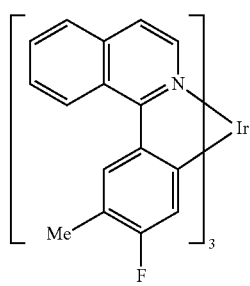

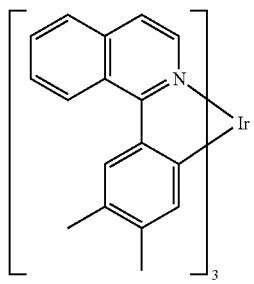

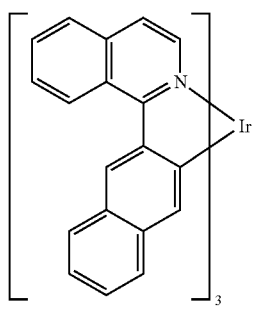

99
-continued
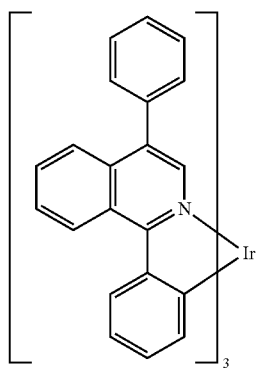
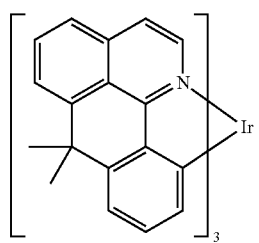
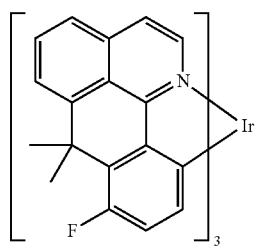
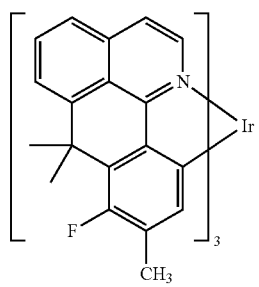
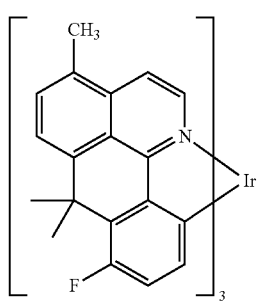
100
-continued
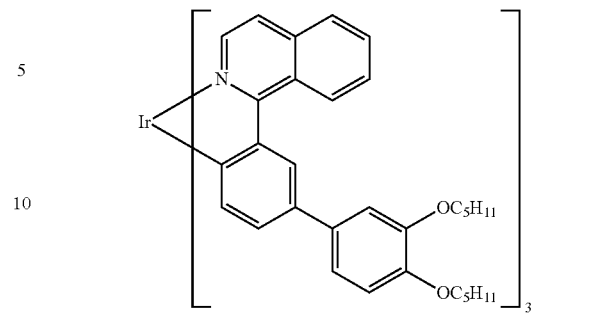
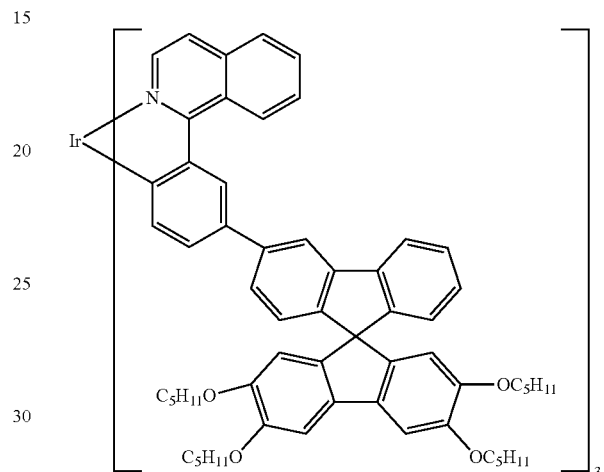
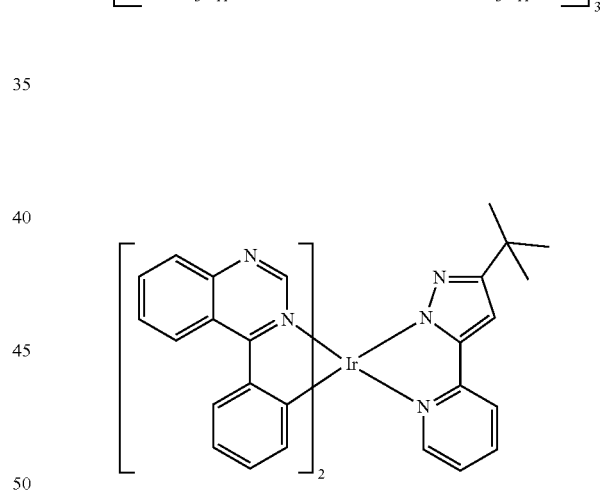
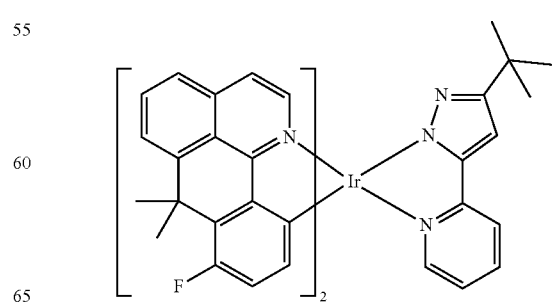

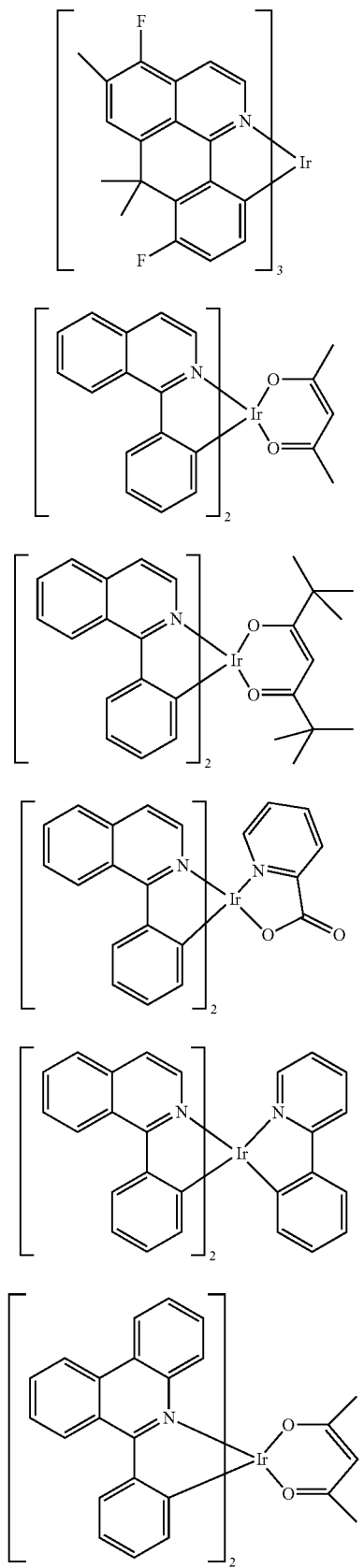
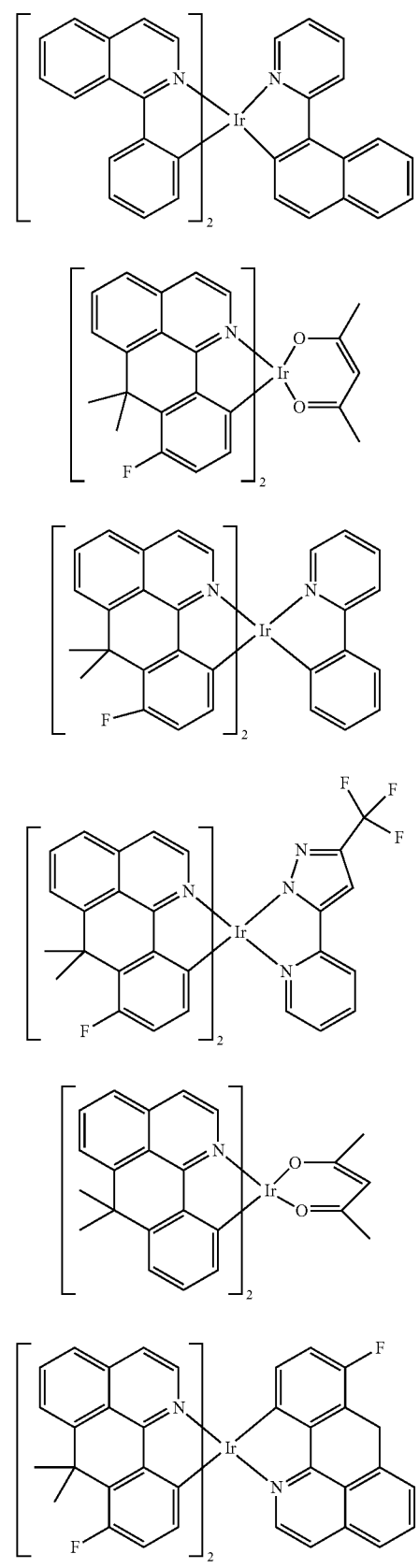

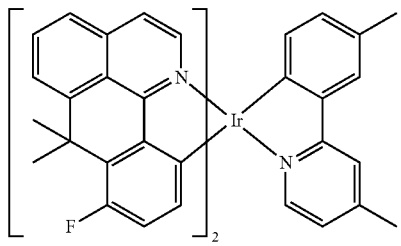
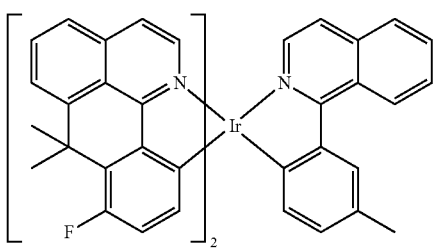
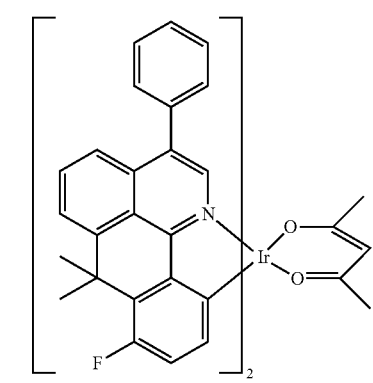
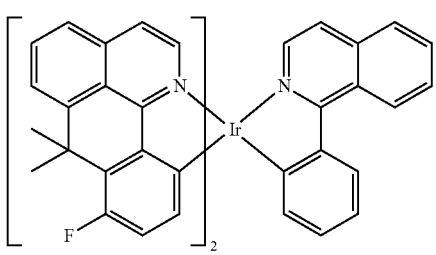
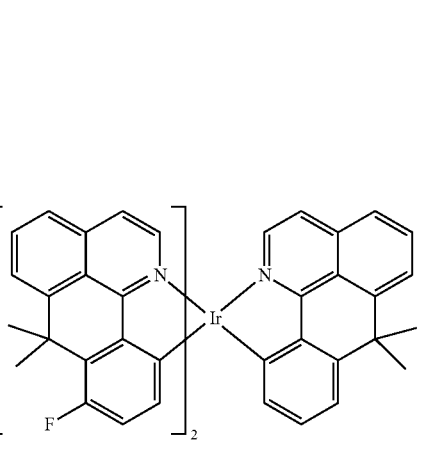
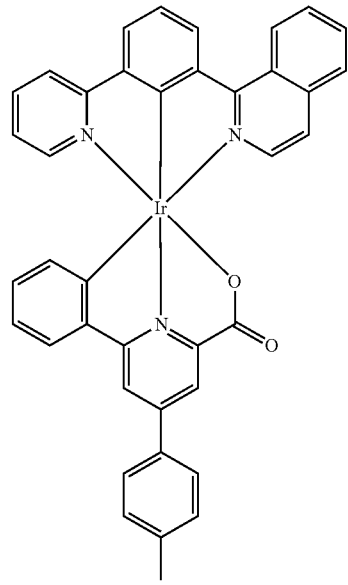
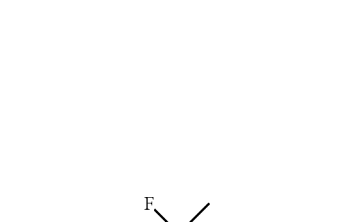
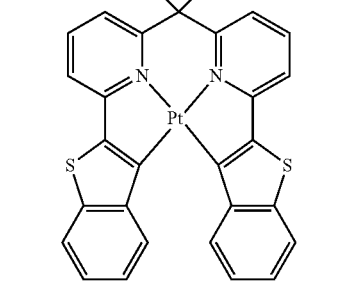

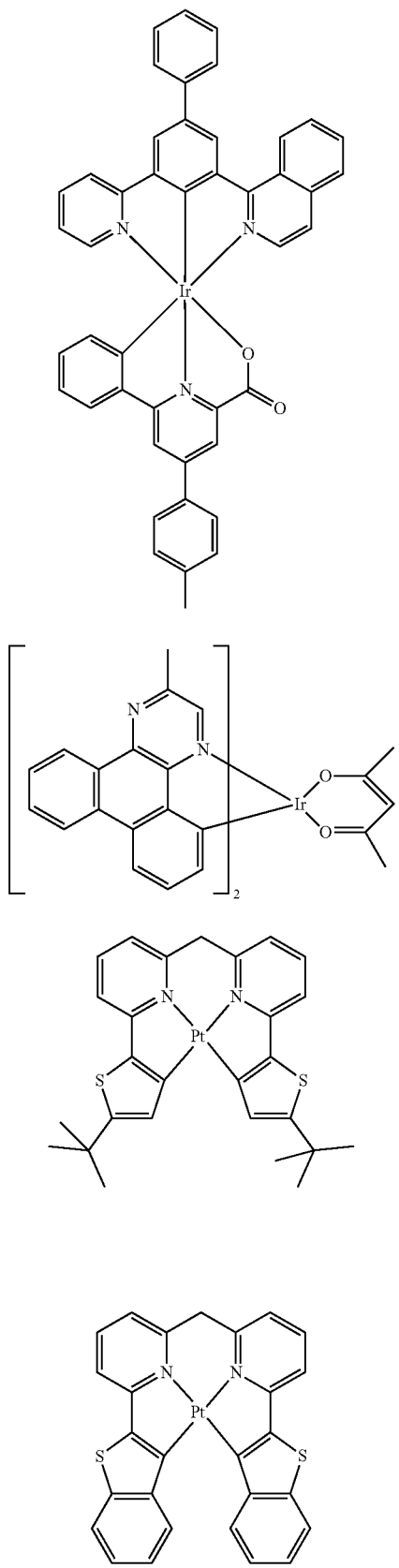

107
-continued
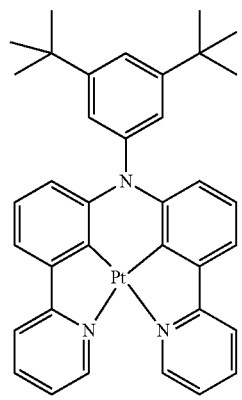
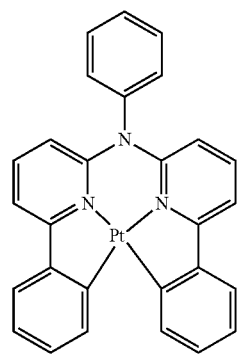
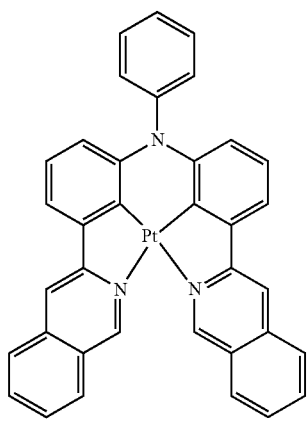
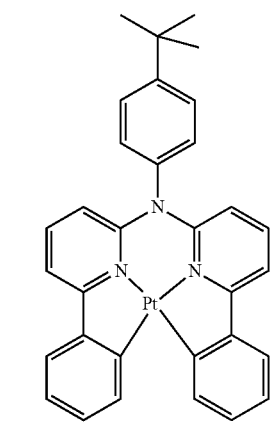
108
-continued
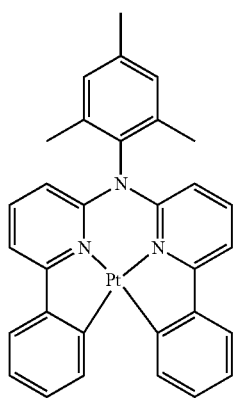
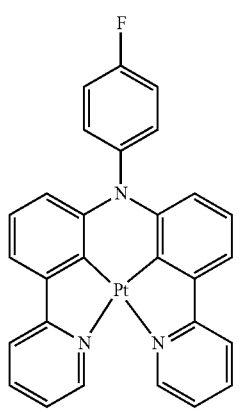
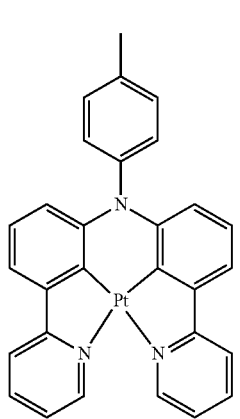

| 109 -continued | 110 -continued |
|---|---|
| 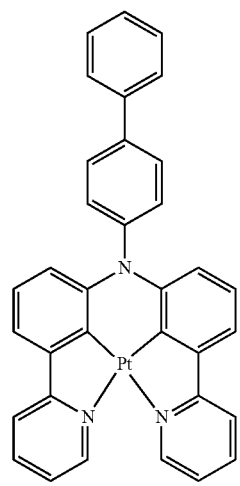 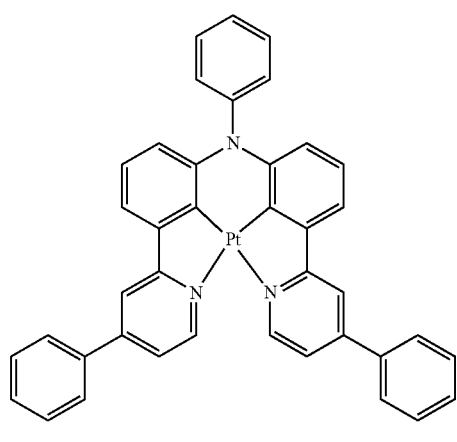 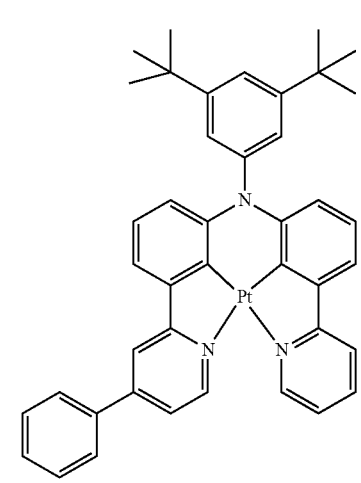 | 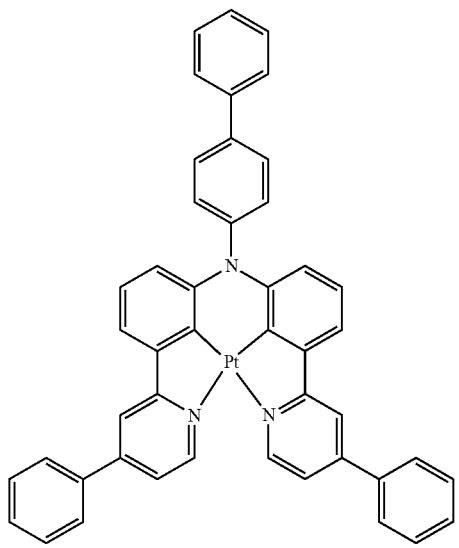 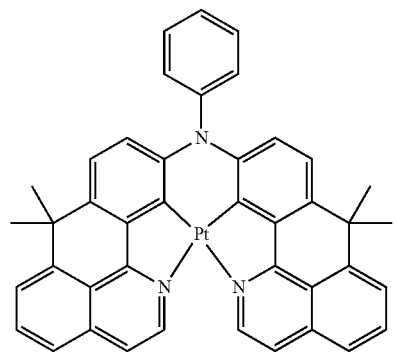 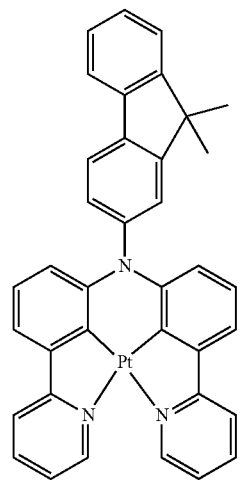 |

| 111 -continued | 112 -continued |
|---|---|
| 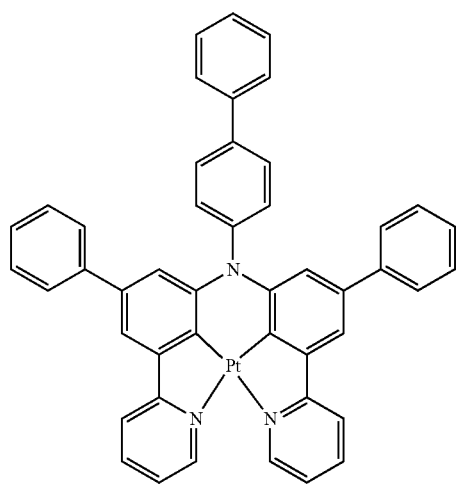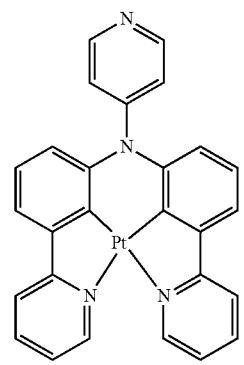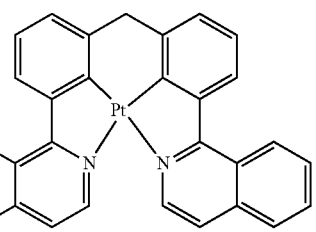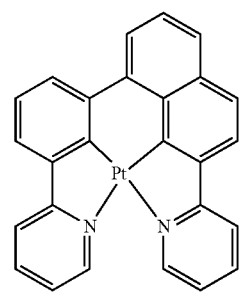 | 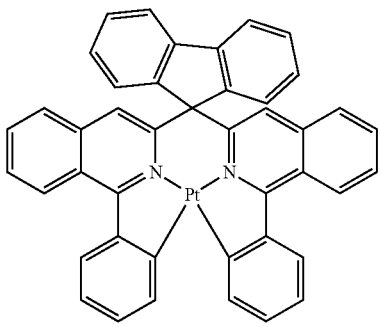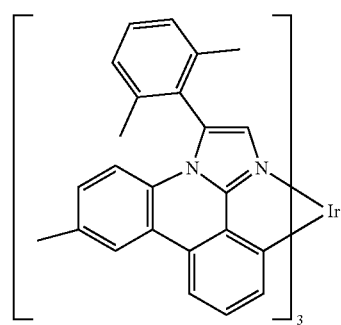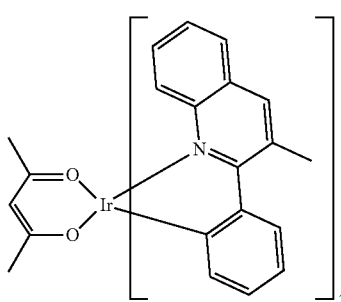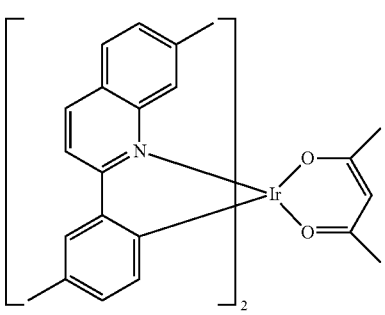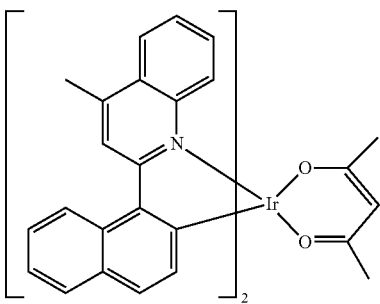 |

113
-continued
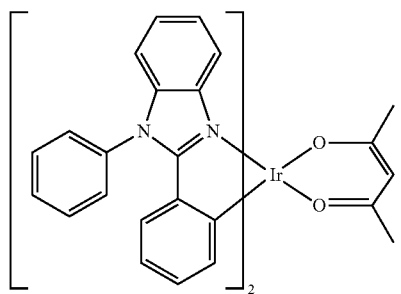
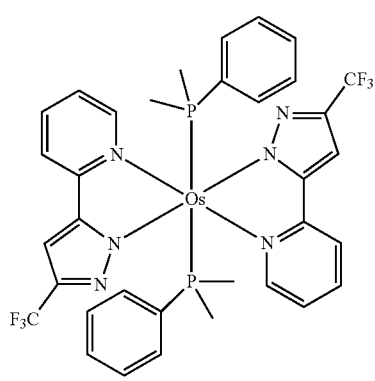
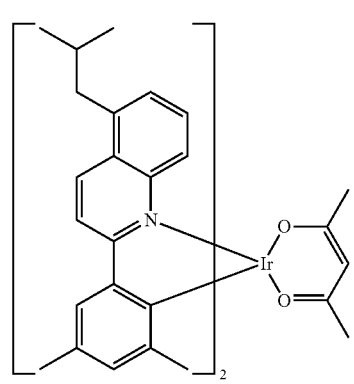
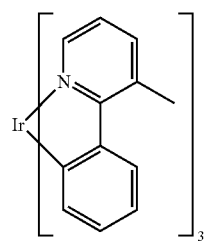
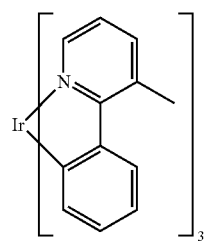
114
-continued
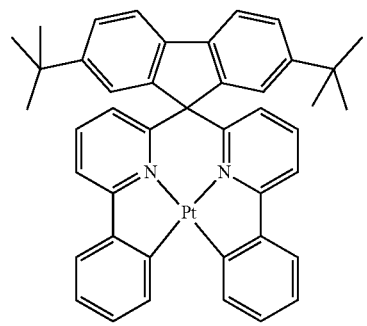
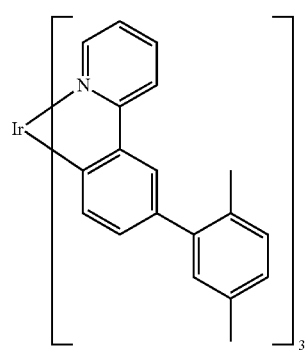
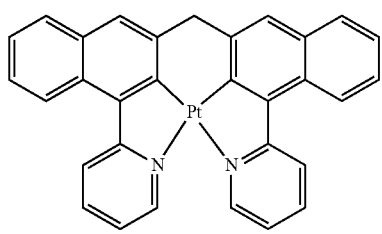

115
-continued
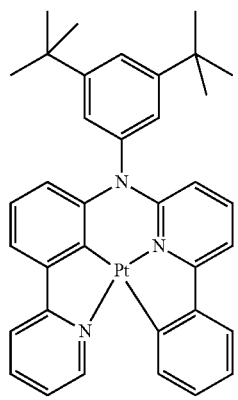
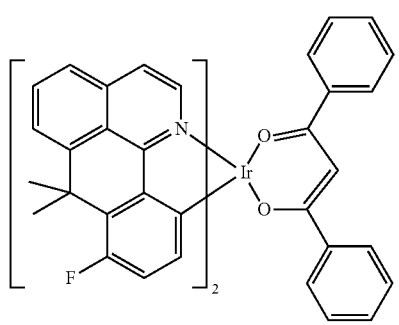
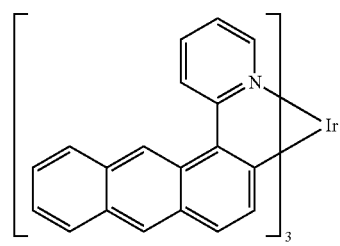
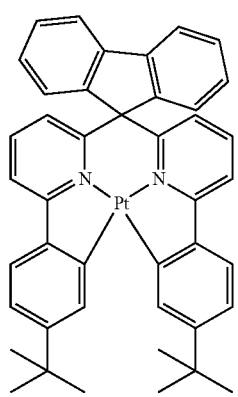
116
-continued
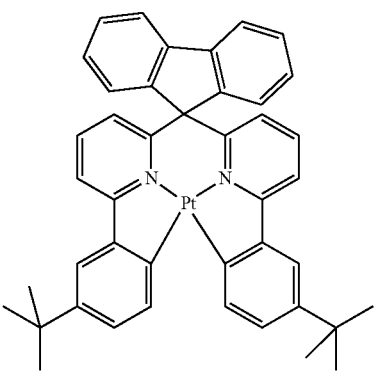
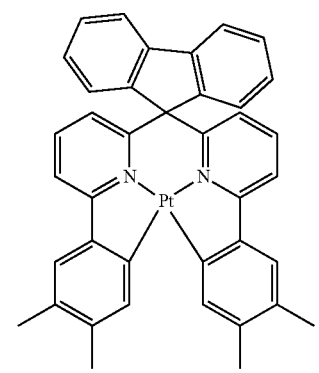
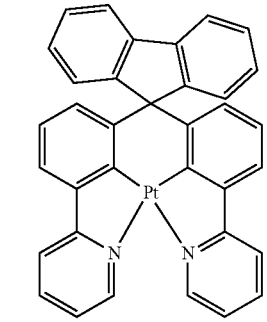

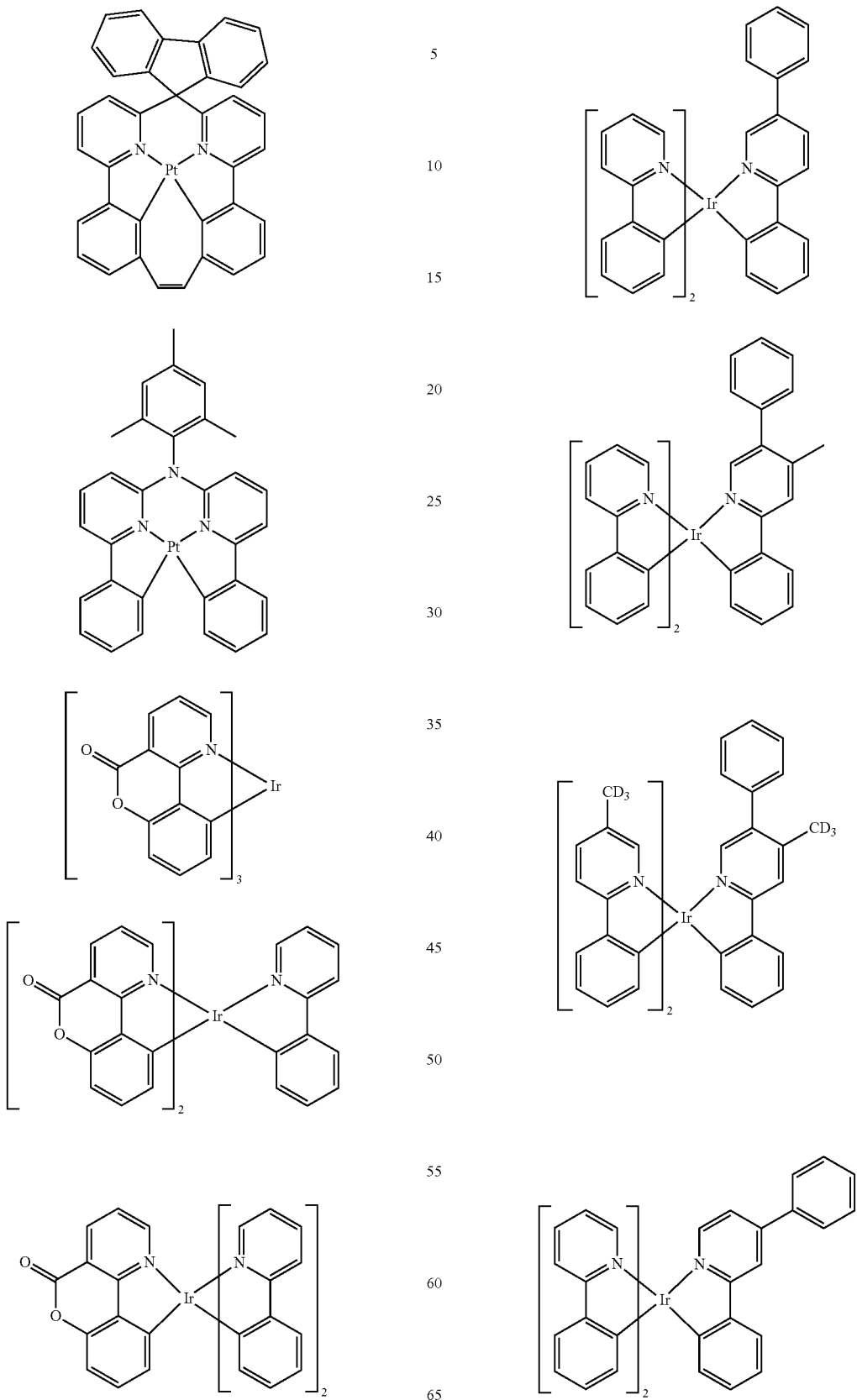

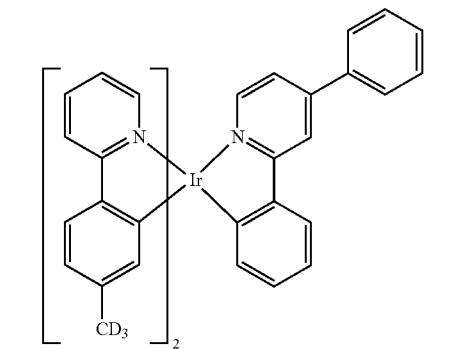
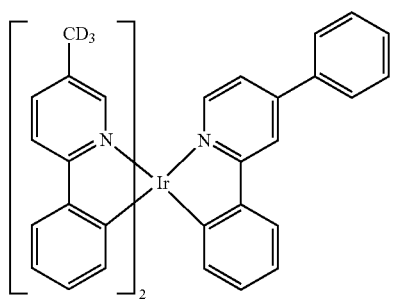
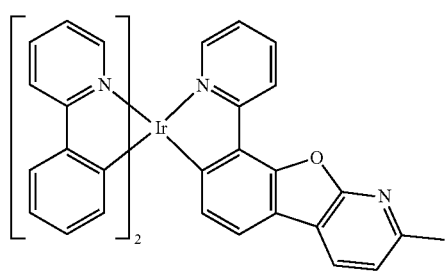
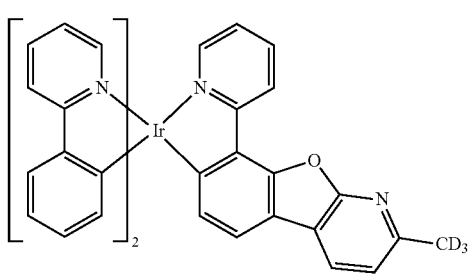
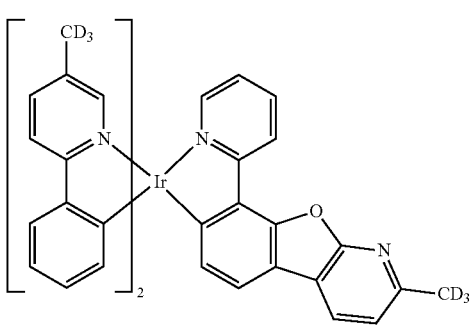
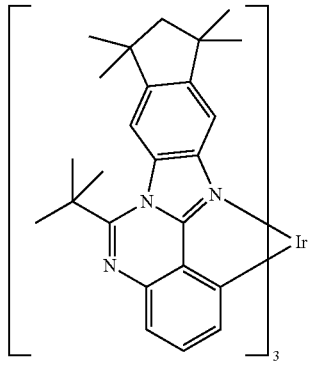
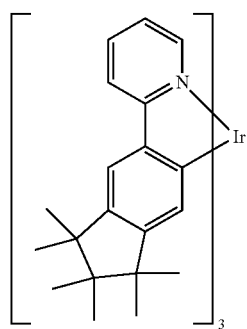
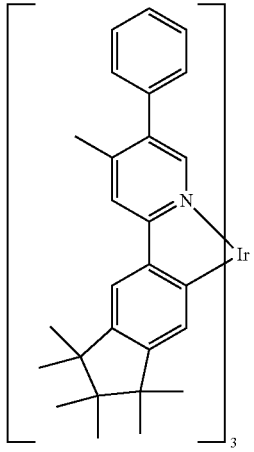
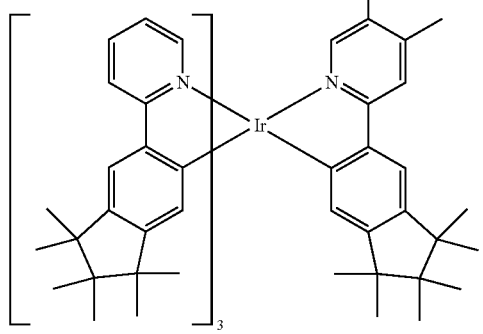

121
-continued
122
-continued
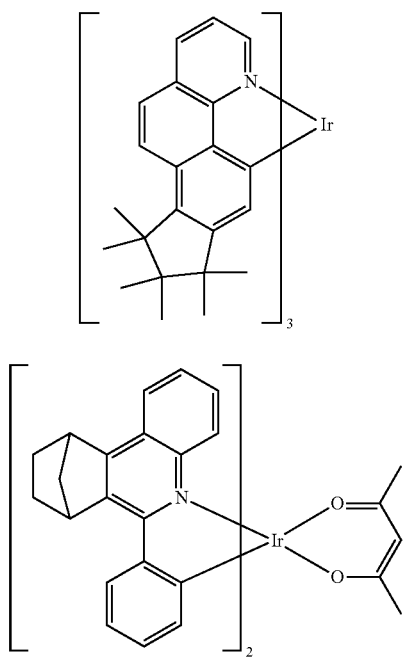
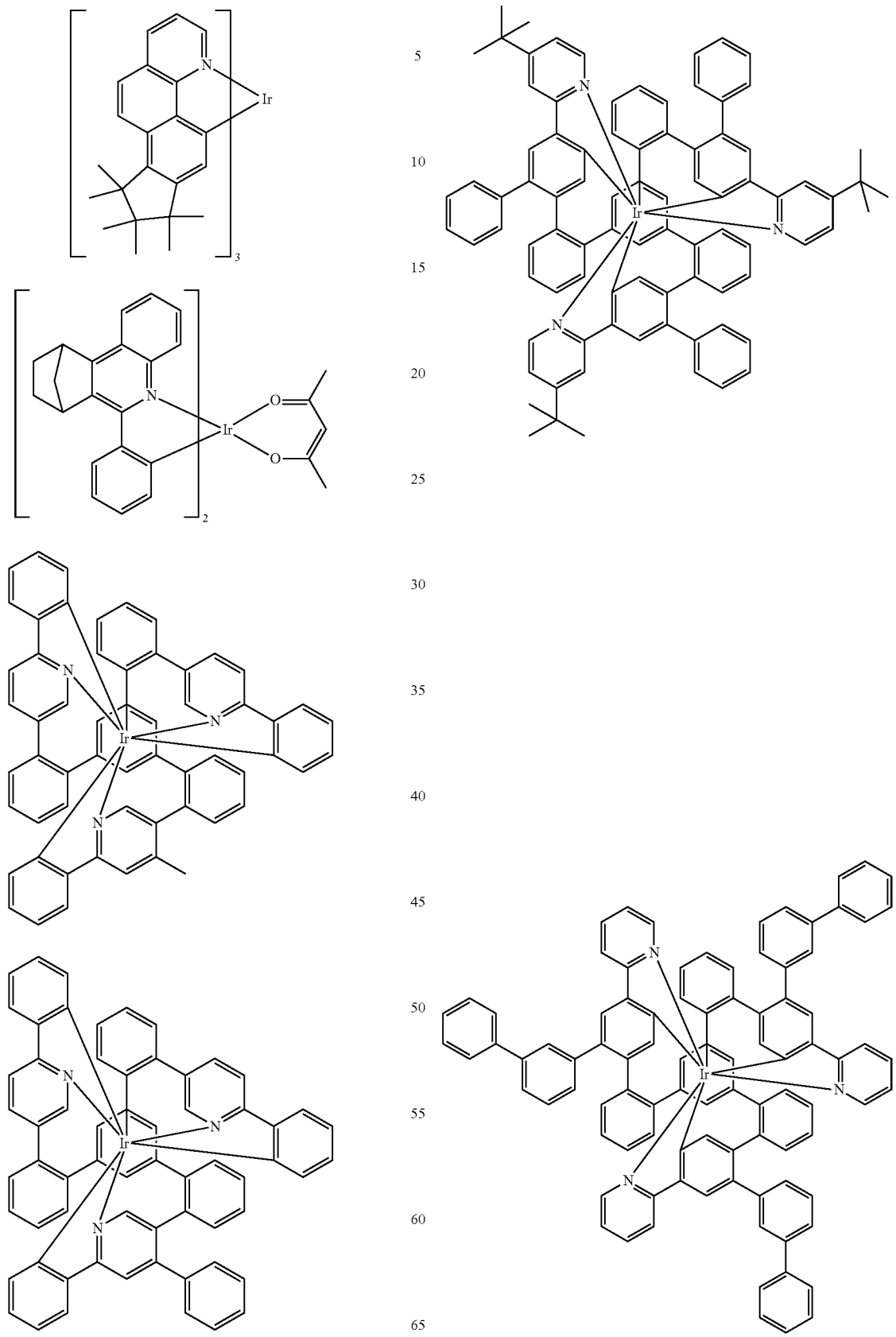

-continued

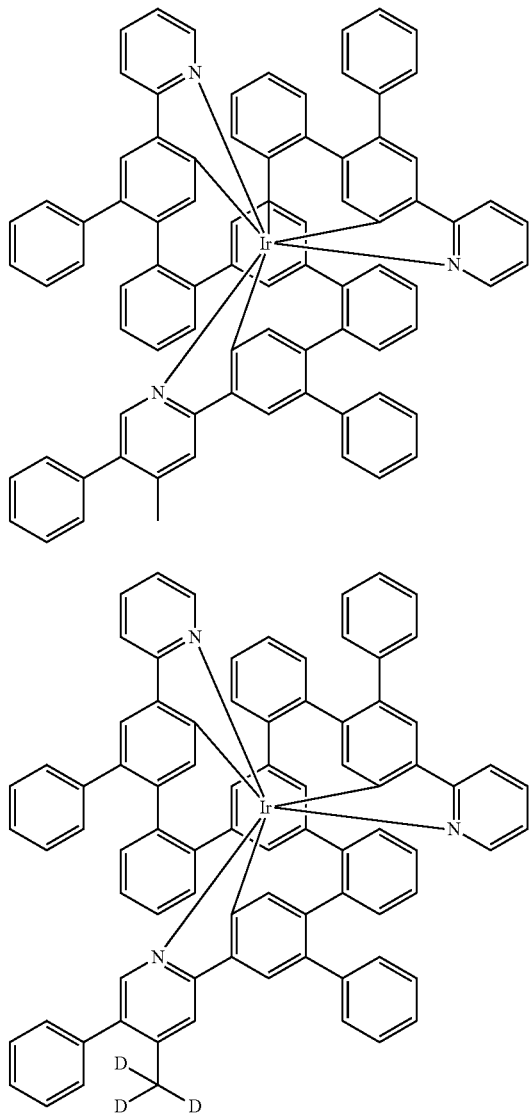

The above-described compound comprising structures of the formula (I) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices, preferably organic electroluminescent devices (OLEDs, PLEDs), especially phosphorescent OLEDs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. Preference is further given to tandem OLEDs as well. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

In a further-preferred embodiment of the invention, the organic electroluminescent device contains the compound of the invention comprising structures of formula (I) or the above-detailed preferred embodiments as matrix material for a phosphorescent emitter.

Suitable matrix materials which can be used in combination with the compounds of formula (I) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, 4-spirocarbazole derivatives, for example according to WO 2014/094963 or WO 2015/192939, or dibenzofuran derivatives, for example according to WO 2015/169412, WO 2016/015810, WO 2016/023608, WO 2017/148564 or WO 2017/148565. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams, carbazole derivatives and biscarbazole derivatives.

Preferred triarylamine derivatives which are used as co-host materials together with the compounds of the invention are selected from the compounds of the following formula (TA-1):

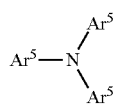

Formula (TA-1)

where $Ar^5$ is the same or different at each instance and is an aromatic or heteroaromatic ring system which has 6 to 40 carbon atoms and may be substituted in each case by one or more $R^2$ radicals, where two or more adjacent $R^2$ substituents may optionally form a mono- or polycyclic, aliphatic ring system which may be substituted by one or more $R^3$ radicals, where the symbol $R^2$ is as defined above, especially for formula (I). Preferably, $Ar^5$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^5$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^5$ groups are the same or different at each instance and are selected from the abovementioned $R^1$-1 to $R^1$-92 groups, more preferably $R^1$-1 to $R^1$-54.

In a preferred embodiment of the compounds of the formula (TA-1), at least one $Ar^5$ group is selected from a biphenyl group, which may be an ortho-, meta- or para-biphenyl group. In a further preferred embodiment of the compounds of the formula (TA-1), at least one $Ar^5$ group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^5$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one $Ar^5$ group is selected from a fluorene or spirobifluorene group, especially a 4-fluorene or 4-spirobifluorene group, and one $Ar^5$ group is selected from a biphenyl group, especially a para-biphenyl group, or a fluorene group, especially a 2-fluorene group, and the third $Ar^5$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

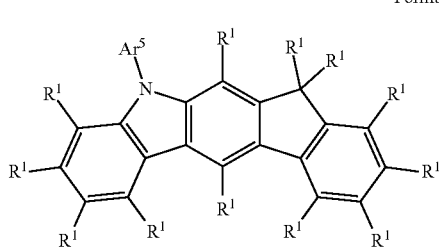

Formula (TA-2)

where $Ar^5$ and $R^1$ have the definitions listed above, especially for formulae (I) and/or (TA-1). Preferred embodiments of the $Ar^5$ group are the above-listed structures $R^1$-1 to $R^1$-92, more preferably $R^1$-1 to $R^1$-54.

A preferred embodiment of the compounds of the formula (TA-2) is the compounds of the following formula (TA-2a):

Formula (TA-2a)

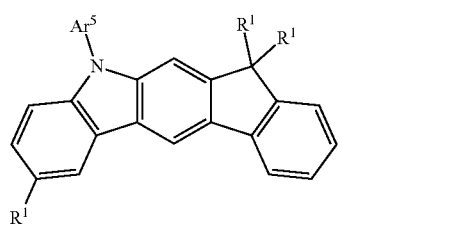

where Ar⁵ and R¹ have the definitions listed above, especially for formulae (I) and/or (TA-1). The two R¹ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two R¹ groups bonded to the indeno carbon atom are methyl groups. Further preferably, the R¹ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

Formula (TA-3)

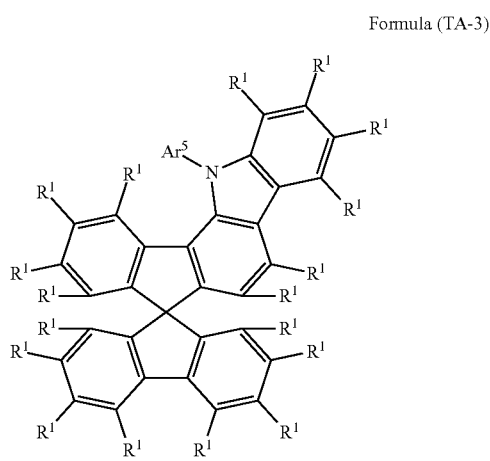

where Ar⁵ and R¹ have the definitions listed above, especially for formulae (I) and/or (TA-1). Preferred embodiments of the Ar⁵ group are the above-listed structures R¹-1 to R¹-92, more preferably R¹-1 to R¹-54.

A preferred embodiment of the compounds of the formula (TA-3) is the compounds of the following formula (TA-3a):

Formula (TA-3a)

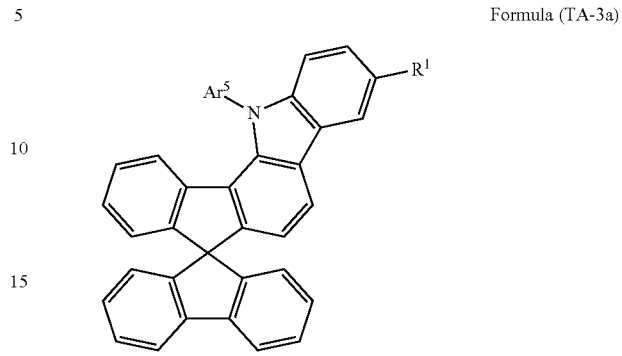

where Ar⁵ and R¹ have the definitions listed above, especially for formulae (I) and/or (TA-1). Preferred embodiments of the Ar⁵ group are the above-listed structures R¹-1 to R¹-92, more preferably R¹-1 to R¹-54.

Preferred biscarbazole derivatives which are used as co-host materials together with the compounds of the invention are selected from the compounds of the following formula (TA-4):

Formula (TA-4)

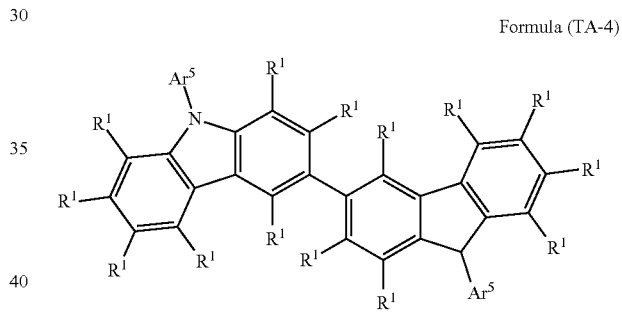

where Ar⁵ and R¹ have the definitions listed above, especially for formulae (I) and/or (TA-1). Preferred embodiments of the Ar⁵ group are the above-listed structures R¹-1 to R¹-92, more preferably R¹-1 to R¹-54.

A preferred embodiment of the compounds of the formula (TA-4) is the compounds of the following formula (TA-4a):

Formula (TA-4)

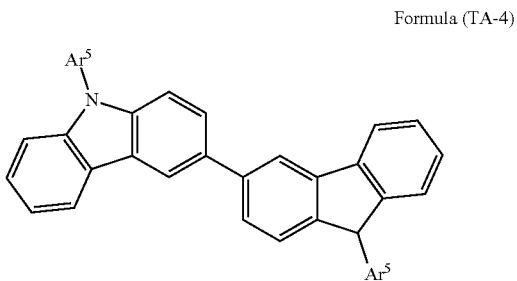

where Ar⁵ has the definitions listed above, especially for formula (TA-1). Preferred embodiments of the Ar⁵ group are the above-listed structures R¹-1 to R¹-92, more preferably R¹-1 to R¹-54.

Examples of suitable biscarbazole derivatives are the materials listed in the following table:
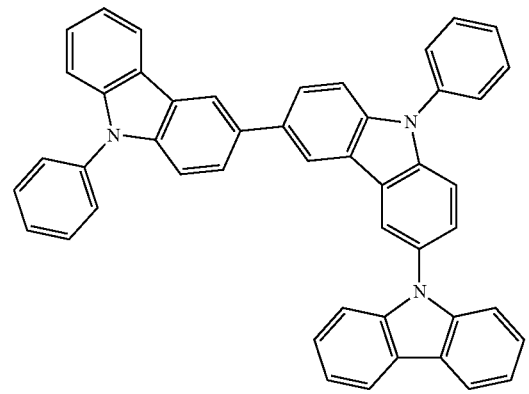 [SMILES: c1ccc(-n2c3ccccc3c3cc(-c4ccc5c(c4)c4cc(-n6c7ccccc7c7ccccc76)ccc4n5-c4ccccc4)ccc32)cc1]
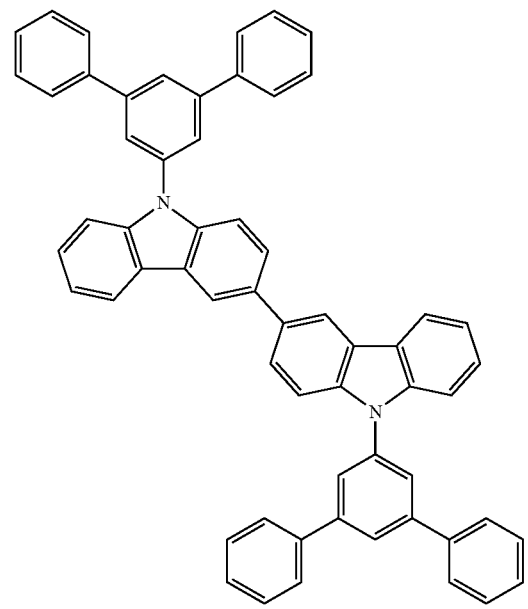 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1]
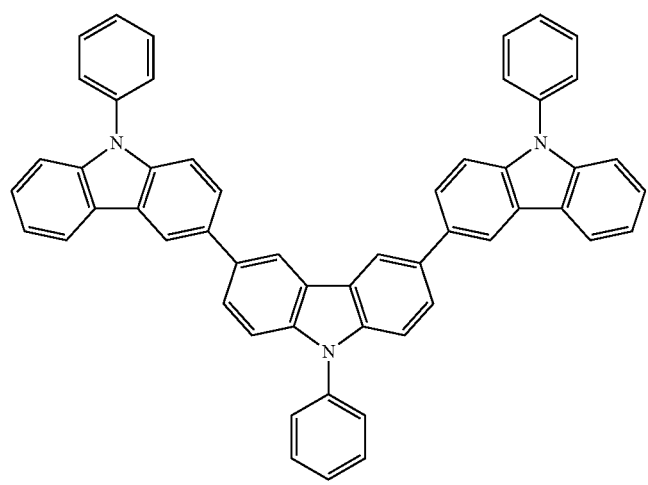 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]

-continued
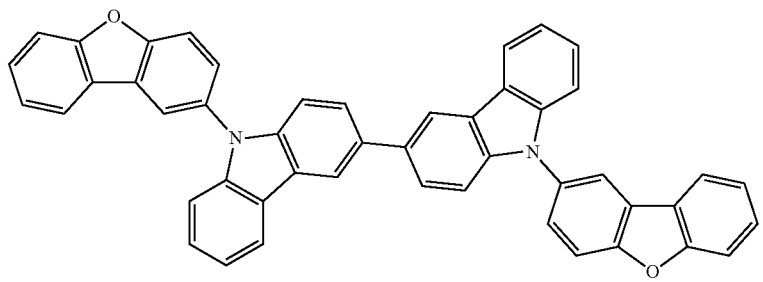 [SMILES: c1ccc2c(c1)oc1ccc(-n3c4ccccc4c4cc(-c5ccc6c(c5)c5ccccc5n6-c5ccc6oc7ccccc7c6c5)ccc43)cc12]
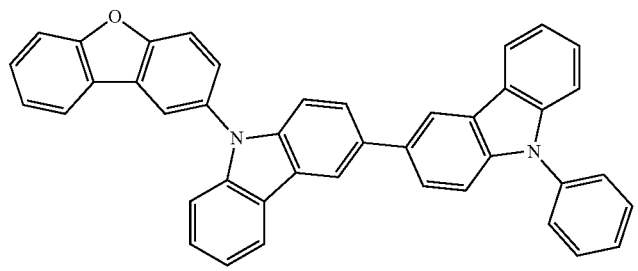 [SMILES: c1ccc(-n2c3ccccc3c3cc(-c4ccc5c(c4)c4ccccc4n5-c4ccc5oc6ccccc6c5c4)ccc32)cc1]
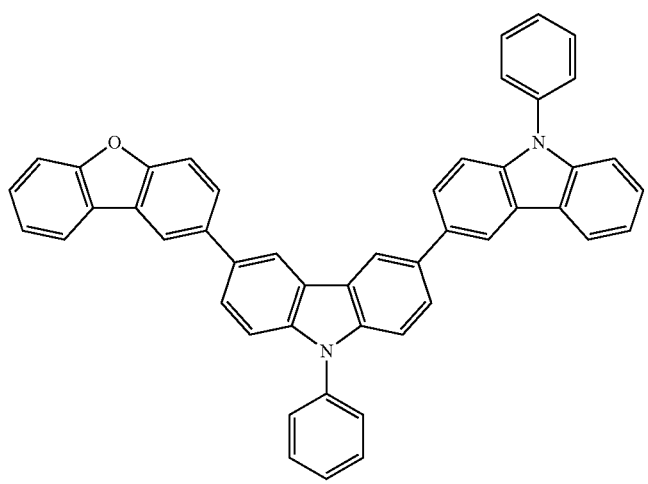 [SMILES: c1ccc(-n2c3ccccc3c3cc(-c4ccc5c(c4)c4cc(-c6ccc7oc8ccccc8c7c6)ccc4n5-c4ccccc4)ccc32)cc1]
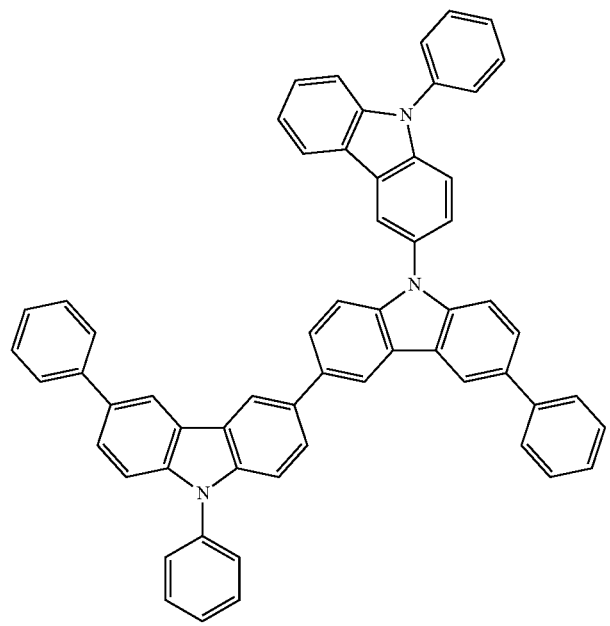 [SMILES: c1ccc(-c2ccc3c(c2)c2cc(-c4ccc5c(c4)c4cc(-c6ccccc6)ccc4n5-c4ccc5c(c4)c4ccccc4n5-c4ccccc4)ccc2n3-c2ccccc2)cc1]

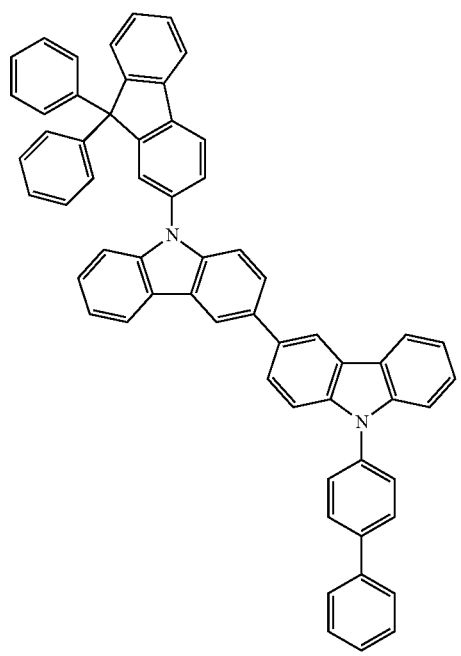 [SMILES: c1ccc(-c2ccc(-n3c4ccccc4c4cc(-c5ccc6c(c5)c5ccccc5n6-c5ccc6c(c5)C(c5ccccc5)(c5ccccc5)c5ccccc5-6)ccc43)cc2)cc1]
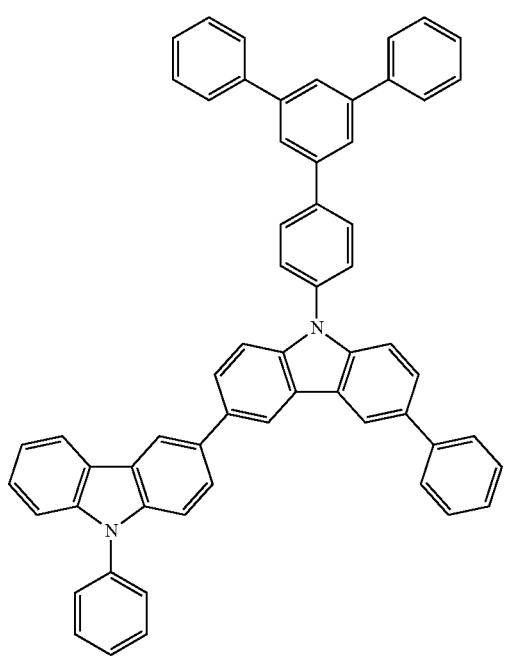 [SMILES: c1ccc(-c2cc(-c3ccccc3)cc(-c3ccc(-n4c5ccc(-c6ccccc6)cc5c5cc(-c6ccc7c(c6)c6ccccc6n7-c6ccccc6)ccc54)cc3)c2)cc1]

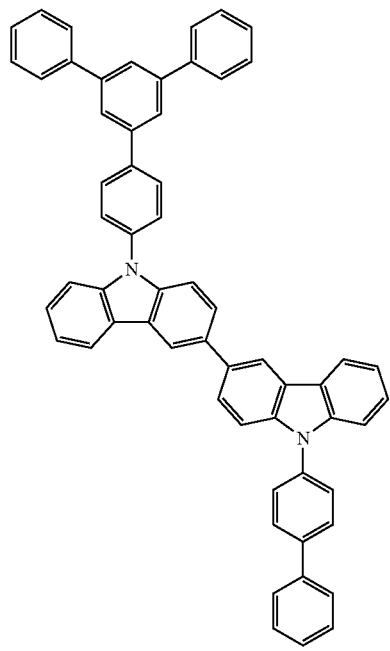 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1]
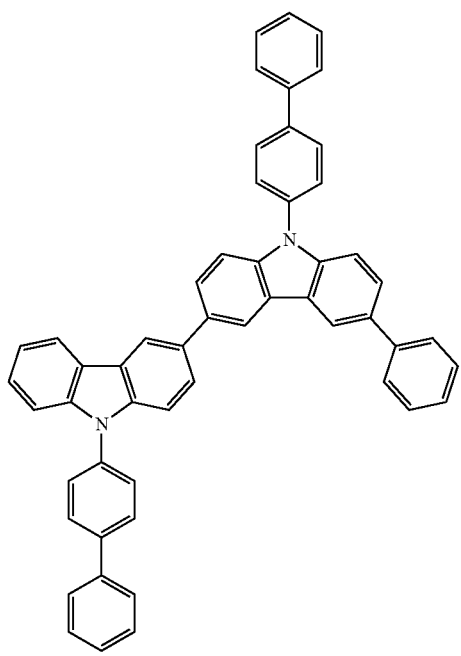 [SMILES: c1ccc(-c2ccc(-n3c4ccccc4c4cc(-c5ccc6c(c5)c5cc(-c7ccccc7)ccc5n6-c5ccc(-c6ccccc6)cc5)ccc43)cc2)cc1]

-continued
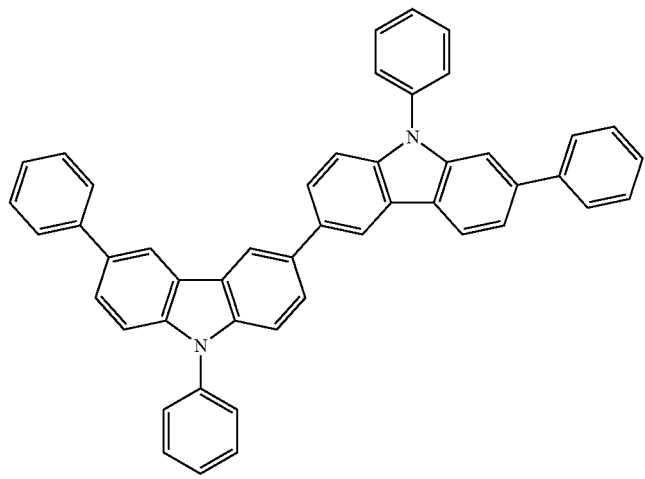 [SMILES: c1ccc(-c2ccc3c(c2)c2cc(-c4ccc5c(c4)c4ccc(-c6ccccc6)cc4n5-c4ccccc4)ccc2n3-c2ccccc2)cc1]
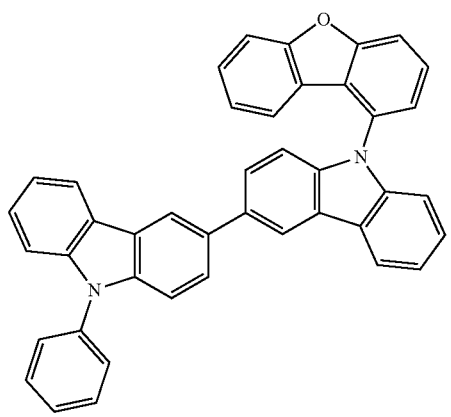 [SMILES: c1ccc(-n2c3ccccc3c3cc(-c4ccc5c(c4)c4ccccc4n5-c4cccc5oc6ccccc6c45)ccc32)cc1]
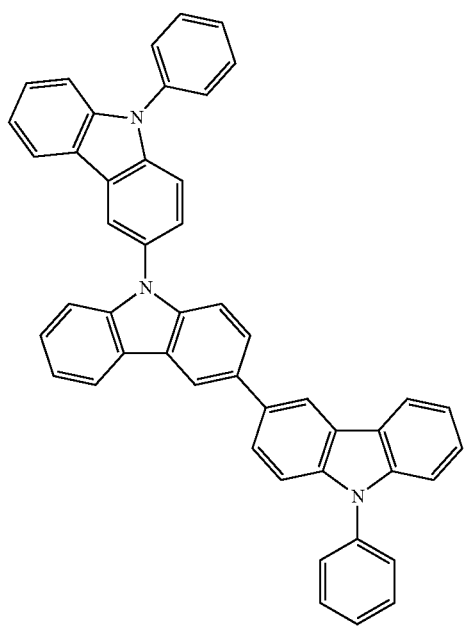 [SMILES: c1ccc(-n2c3ccccc3c3cc(-c4ccc5c(c4)c4ccccc4n5-c4ccc5c(c4)c4ccccc4n5-c4ccccc4)ccc32)cc1]

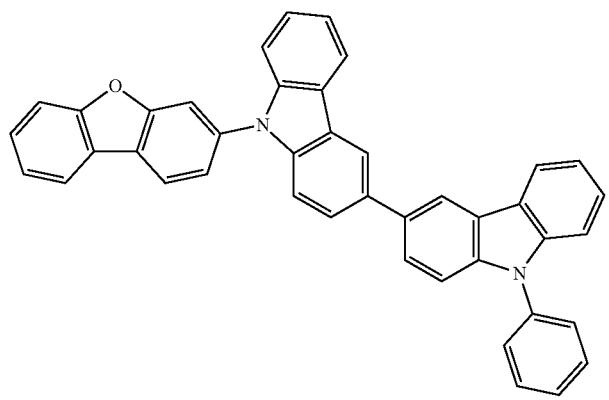 [SMILES: c1ccc(-n2c3ccccc3c3cc(-c4ccc5c(c4)c4ccccc4n5-c4ccc5c(c4)oc4ccccc45)ccc32)cc1]
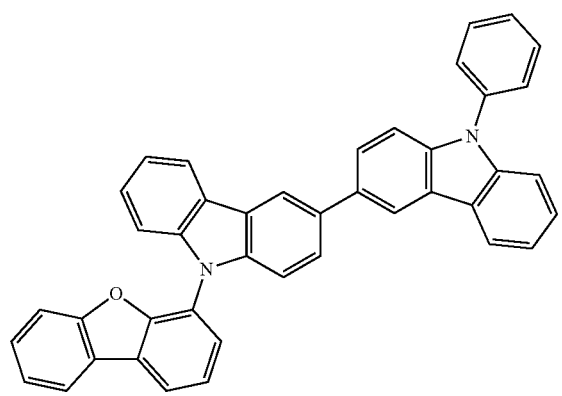 [SMILES: c1ccc(-n2c3ccccc3c3cc(-c4ccc5c(c4)c4ccccc4n5-c4cccc5c4oc4ccccc45)ccc32)cc1]
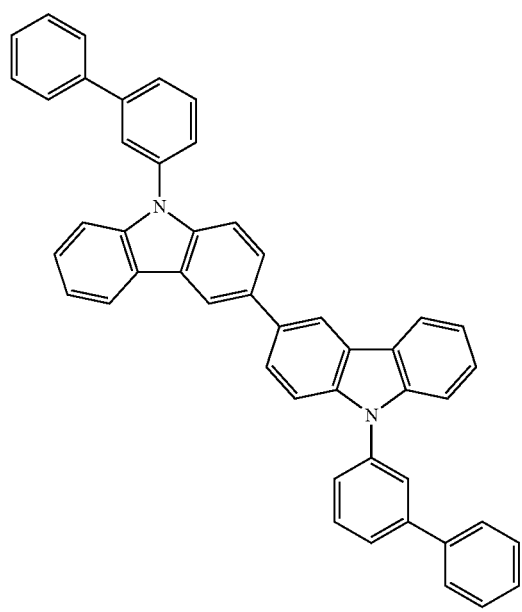 [SMILES: c1ccc(-c2cccc(-n3c4ccccc4c4cc(-c5ccc6c(c5)c5ccccc5n6-c5cccc(-c6ccccc6)c5)ccc43)c2)cc1]

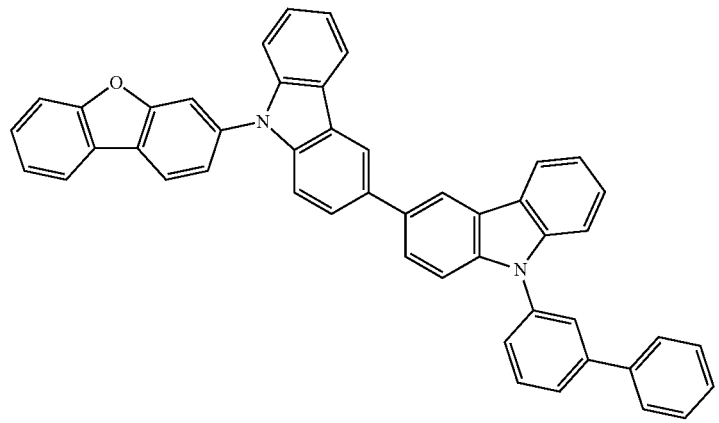 [SMILES: c1ccc(-c2cccc(-n3c4ccccc4c4cc(-c5ccc6c(c5)c5ccccc5n6-c5ccc6c(c5)oc5ccccc56)ccc43)c2)cc1]
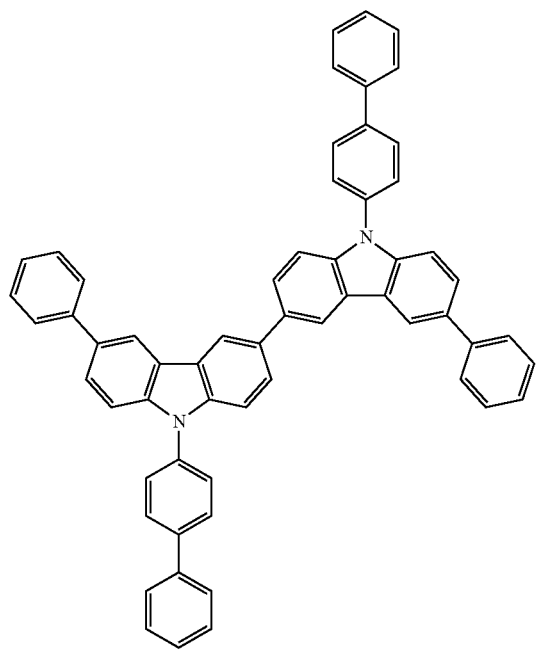 [SMILES: c1ccc(-c2ccc(-n3c4ccc(-c5ccccc5)cc4c4cc(-c5ccc6c(c5)c5cc(-c7ccccc7)ccc5n6-c5ccc(-c6ccccc6)cc5)ccc43)cc2)cc1]
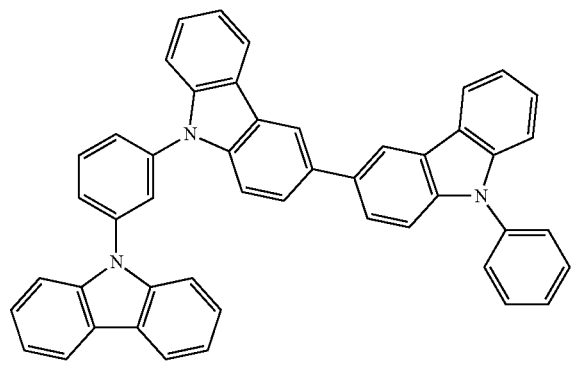 [SMILES: c1ccc(-n2c3ccccc3c3cc(-c4ccc5c(c4)c4ccccc4n5-c4cccc(-n5c6ccccc6c6ccccc65)c4)ccc32)cc1]

-continued
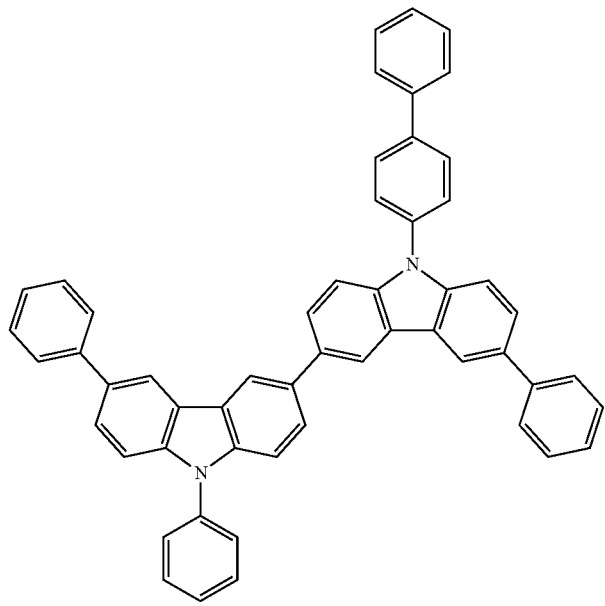 [SMILES: c1ccc(-c2ccc(-n3c4ccc(-c5ccccc5)cc4c4cc(-c5ccc6c(c5)c5cc(-c7ccccc7)ccc5n6-c5ccccc5)ccc43)cc2)cc1]
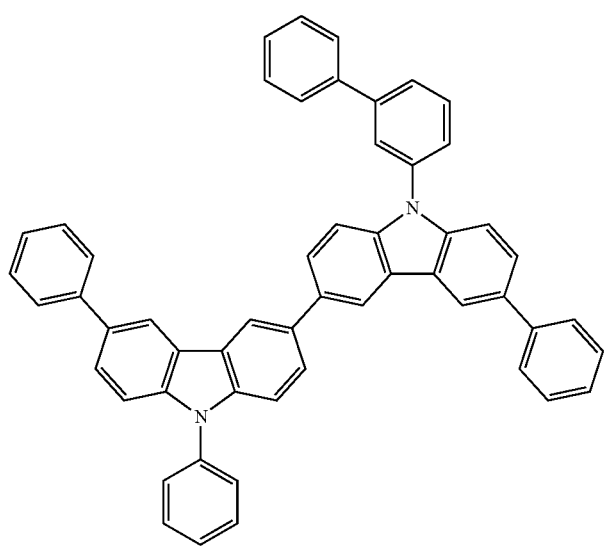 [SMILES: c1ccc(-c2cccc(-n3c4ccc(-c5ccccc5)cc4c4cc(-c5ccc6c(c5)c5cc(-c7ccccc7)ccc5n6-c5ccccc5)ccc43)c2)cc1]

-continued
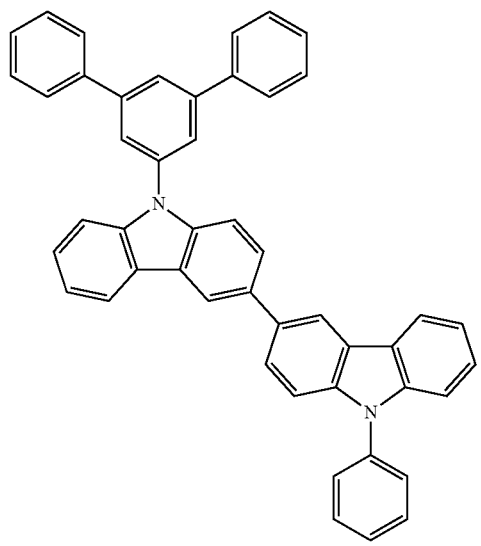 [SMILES: c1ccc(-c2cc(-c3ccccc3)cc(-n3c4ccccc4c4cc(-c5ccc6c(c5)c5ccccc5n6-c5ccccc5)ccc43)c2)cc1]
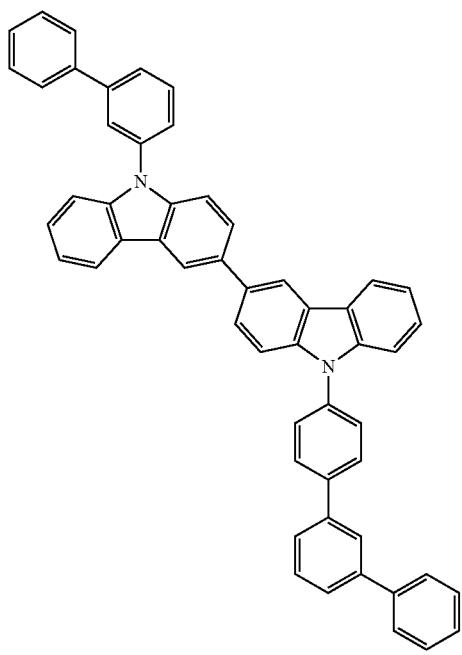 [SMILES: c1ccc(-c2cccc(-c3ccc(-n4c5ccccc5c5cc(-c6ccc7c(c6)c6ccccc6n7-c6cccc(-c7ccccc7)c6)ccc54)cc3)c2)cc1]
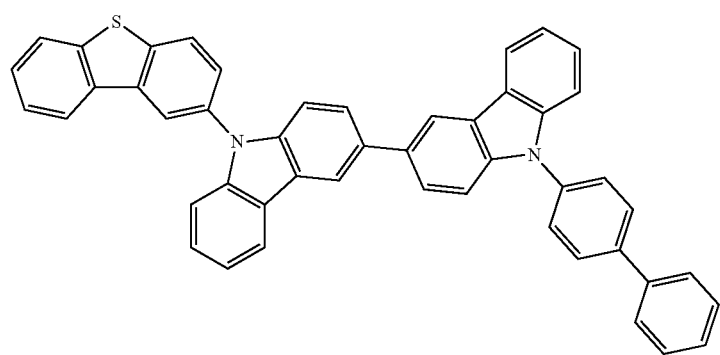 [SMILES: c1ccc(-c2ccc(-n3c4ccccc4c4cc(-c5ccc6c(c5)c5ccccc5n6-c5ccc6sc7ccccc7c6c5)ccc43)cc2)cc1]

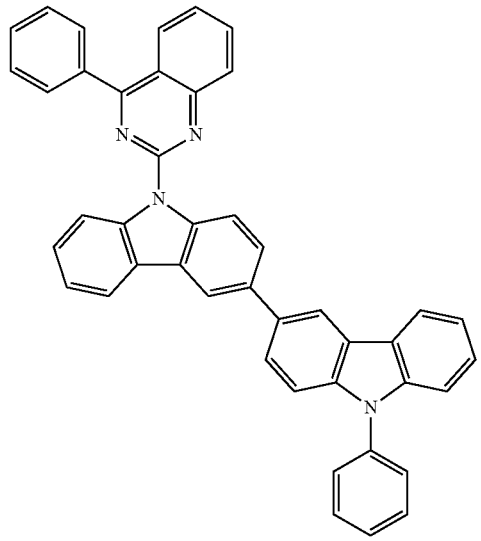 [SMILES: c1ccc(-c2nc(-n3c4ccccc4c4cc(-c5ccc6c(c5)c5ccccc5n6-c5ccccc5)ccc43)nc3ccccc23)cc1]
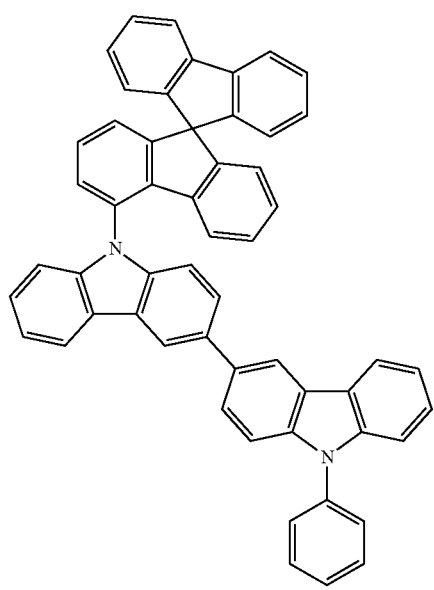 [SMILES: c1ccc(-n2c3ccccc3c3cc(-c4ccc5c(c4)c4ccccc4n5-c4cccc5c4-c4ccccc4C54c5ccccc5-c5ccccc54)ccc32)cc1]

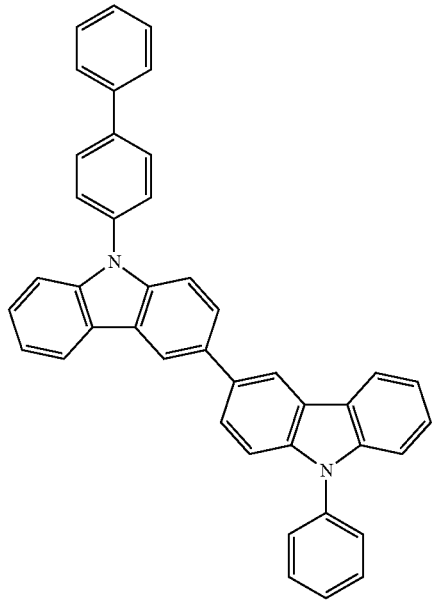 [SMILES: c1ccc(-c2ccc(-n3c4ccccc4c4cc(-c5ccc6c(c5)c5ccccc5n6-c5ccccc5)ccc43)cc2)cc1]
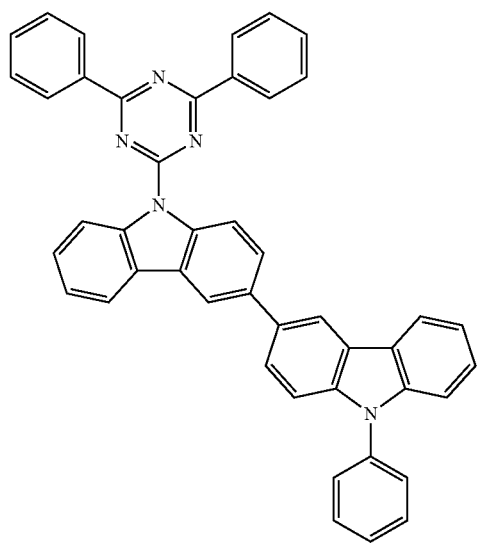 [SMILES: c1ccc(-c2nc(-c3ccccc3)nc(-n3c4ccccc4c4cc(-c5ccc6c(c5)c5ccccc5n6-c5ccccc5)ccc43)n2)cc1]

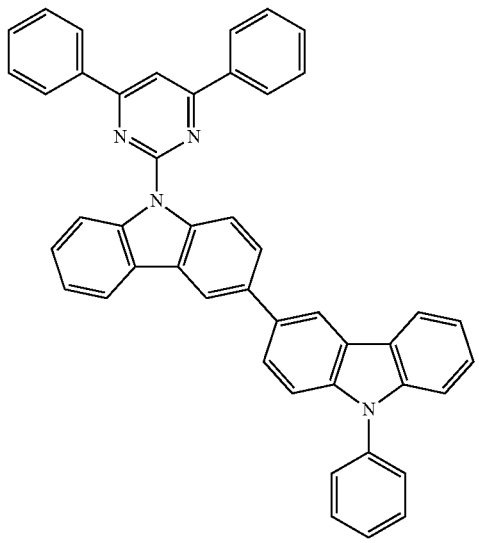 [SMILES: c1ccc(-c2cc(-c3ccccc3)nc(-n3c4ccccc4c4cc(-c5ccc6c(c5)c5ccccc5n6-c5ccccc5)ccc43)n2)cc1]

Preferred lactams which are used as co-host materials together with the compounds of the invention are selected from the compounds of the following formula (LAC-1):

Formula (LAC-1)

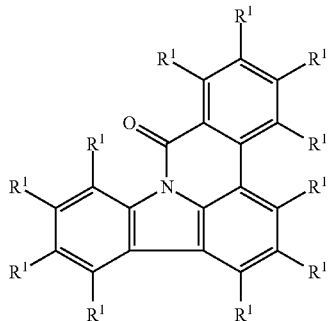

where $R^1$ has the definition listed above, especially for formula (I).

A preferred embodiment of the compounds of the formula (LAC-1) is the compounds of the following formula (LAC-1a):

Formula (LAC-1a)

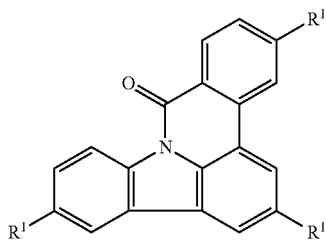

where $R^1$ has the definition given above, especially for formula (I). $R^1$ here is preferably the same or different at each instance and is H or an aromatic or heteroaromatic ring system which has 5 to 40 aromatic ring atoms and may be substituted by one or more $R^2$ radicals, where $R^2$ may have the definition given above, especially for formula (I). Most preferably, the $R^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. Suitable $R^1$ structures here are the same structures as depicted above for R-1 to R-79, more preferably $R^1$-1 to $R^1$-51.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEC. In this case, the matrix material containing compound comprising structures of formula (I) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) or the preferred embodiments recited above and below are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound. Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled.

Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^5$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formula (I) and a matrix material from solution, and to apply a hole blocker layer and/or an electron transport layer thereto by vapor deposition under reduced pressure.

The person skilled in the art is aware of these methods in general terms and is able to apply to them without difficulty to electronic devices, especially organic electroluminescent devices containing compounds of the invention comprising structures of formula (I) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) or the preferred embodiments recited above and hereinafter, especially as electron-conducting materials and/or hole conductor materials or as matrix materials, have a very good lifetime. This is especially true in the case that the compound of the invention is used as matrix material for a red-phosphorescing compound, as hole transport material or as electron transport material.
2. Electronic devices, especially organic electroluminescent devices, comprising compounds, oligomers, polymers or dendrimers having structures of formula (I) or the preferred embodiments recited above and hereinafter, especially as electron transport materials, hole conductor materials and/or as matrix materials, have excellent efficiency. More particularly, efficiency is much higher compared to analogous compounds containing no structural unit of formula (I). In this context, the compounds, oligomers, polymers or dendrimers of the invention having structures of formula (I) or the preferred embodiments recited above and hereinafter bring about a low operating voltage when used in electronic devices. At the same time, these compounds especially bring about low roll-off, i.e. a small drop in power efficiency of the device at high luminances. This is especially true in the case that the compound of the invention is used as matrix material for a red-phosphorescing compound, as hole transport material or as electron transport material.
3. Electronic devices, especially organic electroluminescent devices, comprising compounds, oligomers, polymers or dendrimers having structures of formula (I) or the preferred embodiments recited above and hereinafter, as electron transport materials, hole conductor materials and/or as matrix materials, have excellent color purity.
4. The compounds, oligomers, polymers or dendrimers of the invention having structures of formula (I) or the preferred embodiments recited above and hereinafter exhibit very high thermal and photochemical stability and lead to compounds having a very long lifetime. At the same time, particularly compounds having an arylamine, fluorene or spirobifluorene unit have surprisingly high stability, such that this is conserved even in the case of very efficient and high-performance compounds.
5. With compounds, oligomers, polymers or dendrimers having structures of formula (I) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
6. Compounds, oligomers, polymers or dendrimers having structures of formula (I) or the preferred embodiments recited above and hereinafter have excellent glass film formation.
7. Compounds, oligomers, polymers or dendrimers having structures of formula (I) or the preferred embodiments recited above and hereinafter form very good films from solutions.

These abovementioned advantages are not accompanied by a deterioration in the further electronic properties.

The compounds and mixtures of the invention are suitable for use in an electronic device. An electronic device is understood here to mean a device containing at least one layer containing at least one organic compound. The component may, however, also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as matrix material, hole conductor material, electron injection material and/or electron transport material, preferably as matrix material for a red-phosphorescing compound, hole transport material or electron transport material.

The present invention still further provides an electronic device comprising at least one of the above-detailed compounds or mixtures of the invention. In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices, preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (I) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Any feature disclosed in the present invention, unless stated otherwise, should therefore be considered as an example from a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby. The person skilled in the art will be able to use the details given, without exercising inventive skill, to produce further compounds and electronic devices of the invention and hence to execute the invention over the entire scope claimed.

EXAMPLES

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

Synthesis Examples a) Indolizino[3,4,5-ab]isoindole-2-boronic Acid

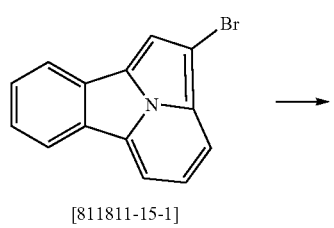

[811811-15-1]

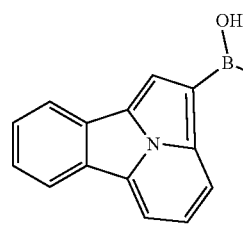

197 g (729 mmol) of 2-bromoindolizino[3,4,5-ab]isoindole are dissolved in 1500 ml of dry THF and cooled to −78° C. At this temperature, 305 ml (764 mmol/2.5 M in hexane) of n-butyllithium are added within about 5 min, and then the mixture is stirred at −78° C. for a further 2.5 h. At this temperature, 150 g (1455 mmol) of trimethyl borate are added very rapidly and the reaction is allowed to come gradually to room temperature (about 18 h). The reaction solution is washed with water and the precipitated solids and the organic phase are subjected to azeotropic drying with toluene. The crude product is extracted while stirring from toluene/methylene chloride at about 40° C. and filtered off with suction. Yield: 148 g (529 mmol), 81% of theory.

b) (2-Chlorophenyl)indolizino[3,4,5-ab]isoindol-2-ylamine

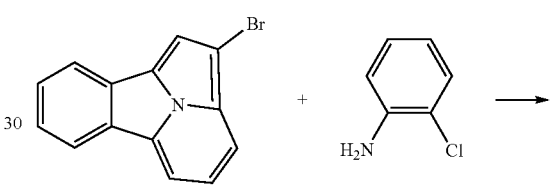

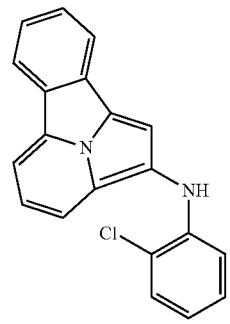

37 g (137 mmol) of 2-bromoindolizino[3,4,5-ab]isoindole, 17.5 g (137 mmol) of 2-chloroaniline, 68.2 g (710 mmol) of sodium tert-butoxide, 613 mg (3 mmol) of palladium(II) acetate and 3.03 g (5 mmol) of 1,1'-bis(diphenylphosphino)ferrocene (dppf) are dissolved in 1.3 l of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 34 g (107 mmol), 80% of theory.

In an analogous manner, it is possible to prepare the following compound:

| Reactant 1 | Reactant 2 | Product | Yield |
|---|---|---|---|
| 1b [811811-15-1] | 7285-66-7 | | 80% | c) Cyclization (Method A)

| | Reactant | Product | Yield |
|---|---|---|---|
| 1c | | | 65% | d) 2-(2-Nitrophenyl)indolizino[3,4,5-ab]isoindole 31.6 g (100 mmol) of (2-chlorophenyl)indolizino[3,4,5-ab]isoindol-2-yl-amine, 56 g (409 mmol) of potassium carbonate, 4.5 g (12 mmol) of tricyclohexylphosphine tetrafluoroborate and 1.38 g (6 mmol) of palladium(II) acetate are suspended in 500 ml of dimethylacetamide and stirred under reflux for 6 h. After cooling, the reaction mixture is extended with 300 ml of water and 400 ml of $CH_2Cl_2$. The mixture is stirred for a further 30 min, the organic phase is separated off and filtered through a short Celite bed, and then the solvent is removed under reduced pressure.

The crude product is subjected to hot extraction with toluene and recrystallized from toluene. The product is isolated as a beige solid. Yield: 19 g (68 mmol), 68% of theory.

In an analogous manner, it is possible to prepare the following compound:

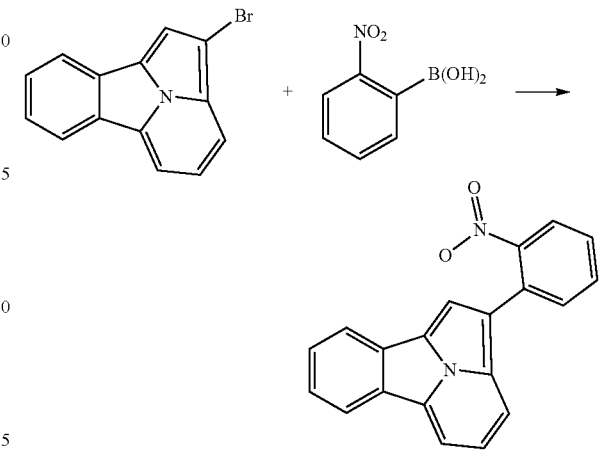

To a well-stirred, degassed suspension of 30 g (184 mmol) of B-(2-nitrophenyl)boronic acid, 49 g (180 mmol) of 2-bromoindolizino[3,4,5-ab]isoindole and 66.5 g (212.7 mmol) of potassium carbonate in a mixture of 250 ml of water and 250 ml of THF are added 1.7 g (1.49 mmol) of Pd(PPh$_3$)$_4$, and the mixture is heated under reflux for 17 h. After cooling, the organic phase is removed, washed three times with 200 ml of water and once with 200 ml of saturated aqueous sodium chloride solution, dried over magnesium sulfate and concentrated to dryness by rotary evaporation. The gray residue is recrystallized from hexane. The precipitated crystals are filtered off with suction, washed with a little MeOH and dried under reduced pressure; yield: 47 g (150 mmol), 82% of theory.

e) Cyclization (Method B)

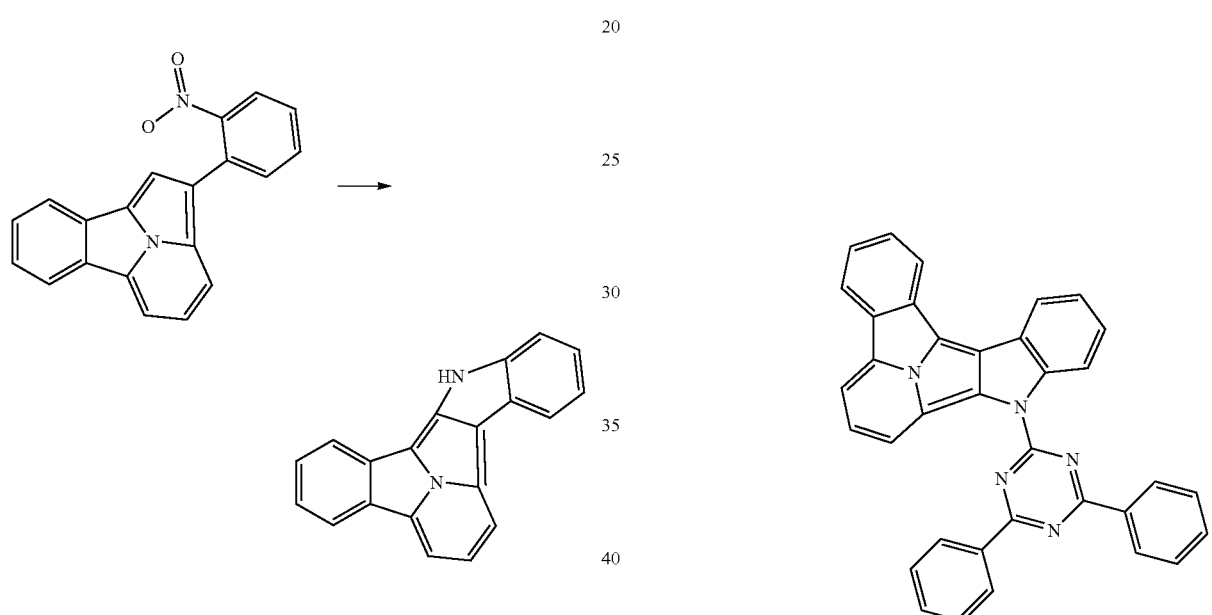

Compound (c)

A mixture of 75 g (240 mmol) of 2-(2-nitrophenyl)indolizino[3,4,5-ab]isoindole and 290.3 ml (1669 mmol) of triethyl phosphite is heated under reflux for 12 h. Subsequently, the rest of the triethyl phosphite is distilled off (72-76° C./9 mmHg). Water/MeOH (1:1) is added to the residue, and the solids are filtered off and recrystallized from toluene. Yield: 47 g (167 mmol), 70% of theory.

f) Nucleophilic Substitution

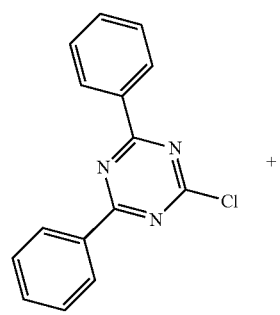

4.2 g of NaH (106 mmol, 60% in mineral oil), are dissolved in 300 ml of dimethylformamide under a protective atmosphere. 29 g (106 mmol) of compound (c) are dissolved in 250 ml of DMF and added dropwise to the reaction mixture. After 1 h at room temperature, a solution of 2-chloro-4,6-diphenyl-[1,3,5]-triazine (34.5 g, 0.122 mol) in 200 ml of THF is added dropwise. The reaction mixture is stirred at room temperature for 12 h and then poured onto ice. After warming to room temperature, the solids that precipitate out are filtered and washed with ethanol and heptane. The residue is subjected to hot extraction with toluene, recrystallized from toluene/n-heptane and finally sublimed under high vacuum. The purity is 99.9%. The yield is 32 g (63 mmol; 60% of theory).

The following compounds can be prepared in an analogous manner:

| | Reactant 1 | Reactant 2 |
|---|---|---|
| 1f | 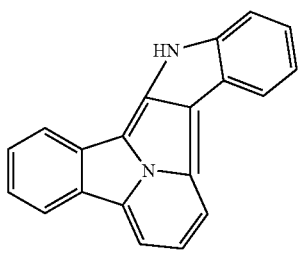 [SMILES: c1ccc2c(c1)[nH]c1c2c2cccc3c4ccccc4c1n32] | 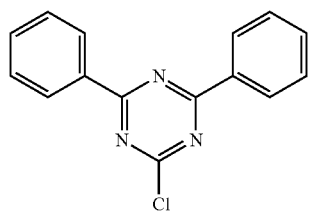<br>3842-55-5 |
| 2f | 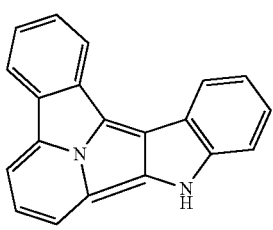 [SMILES: c1ccc2c(c1)[nH]c1c2c2c3ccccc3c3cccc1n32] | 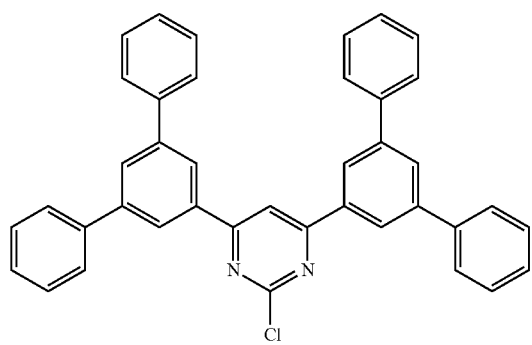<br>1384480-21-0 |
| 3f | 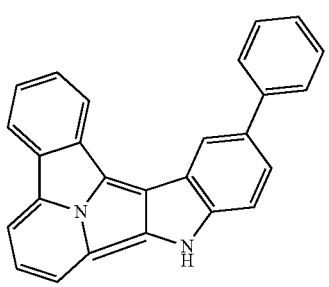 [SMILES: c1ccc(-c2ccc3[nH]c4c(c3c2)c2c3ccccc3c3cccc4n32)cc1] | 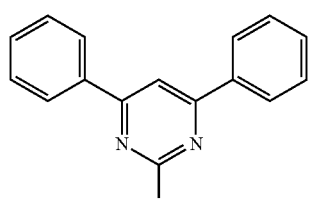<br>2915-16-4 |
| 4f | 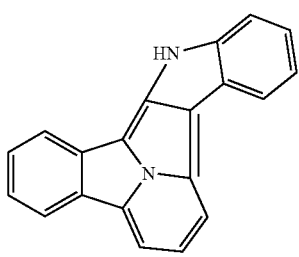 [SMILES: c1ccc2c(c1)[nH]c1c2c2cccc3c4ccccc4c1n32] | 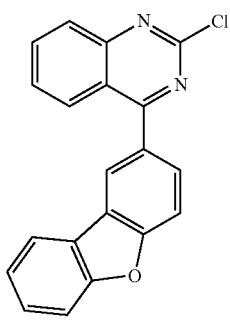<br>[1616499-38-7] |

-continued
| | | | |
|---|---|---|---|
| 5f | 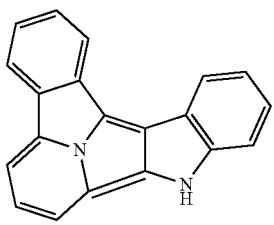 [SMILES: c1ccc2c(c1)[nH]c1c2c2c3ccccc3c3cccc1n32] | | 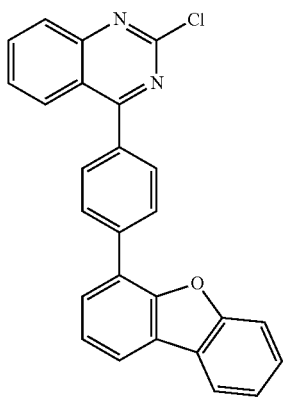 |
| | | | [1403252-58-3] |
| 6f | 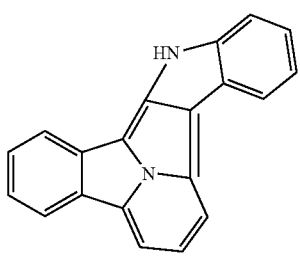 [SMILES: c1ccc2c(c1)[nH]c1c2c2cccc3c4ccccc4c1n32] | | 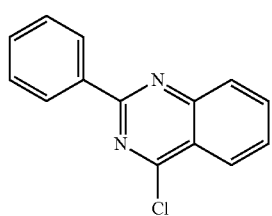 |
| | | | [6484-25-9] |
| 7f | 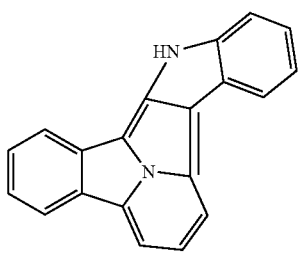 [SMILES: c1ccc2c(c1)[nH]c1c2c2cccc3c4ccccc4c1n32] | | 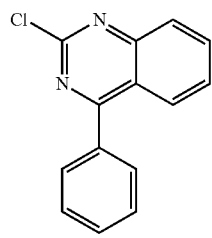 |
| | | | [29874-83-7] |
| 8f | 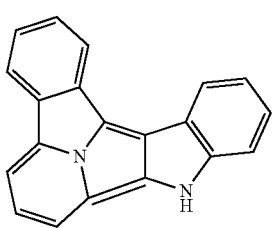 [SMILES: c1ccc2c(c1)[nH]c1c2c2c3ccccc3c3cccc1n32] | | 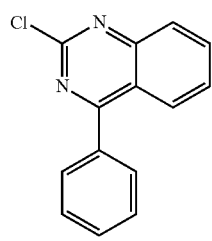 |
| | | | [29874-83-7] |
| 9f | 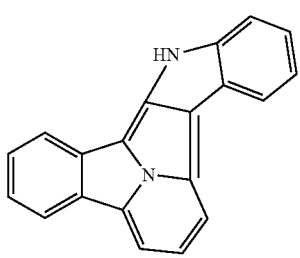 [SMILES: c1ccc2c(c1)[nH]c1c2c2cccc3c4ccccc4c1n32] | | 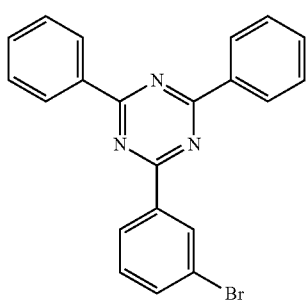 |
| | | | 864377-31-1 |

-continued
| | Product | Yield |
|---|---|---|
| 1f | 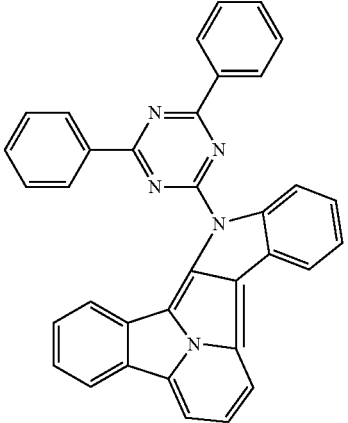 [SMILES: c1ccc(-c2nc(-c3ccccc3)nc(-n3c4ccccc4c4c3c3c5ccccc5c5cccc4n53)n2)cc1] | 61% |
| 2f | 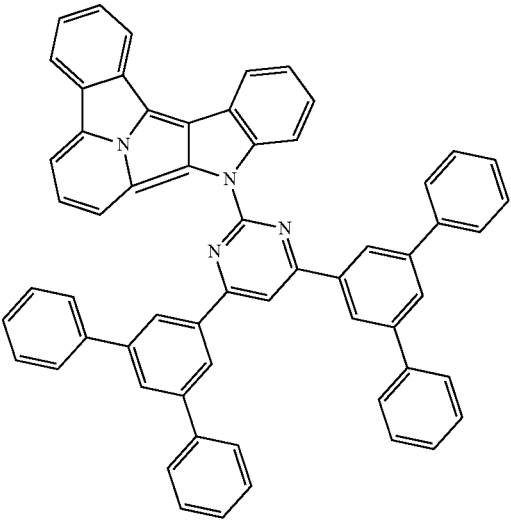 [SMILES: c1ccc(-c2cc(-c3ccccc3)cc(-c3cc(-c4cc(-c5ccccc5)cc(-c5ccccc5)c4)nc(-n4c5ccccc5c5c4c4cccc6c7ccccc7c5n64)n3)c2)cc1] | 60% |
| 3f | 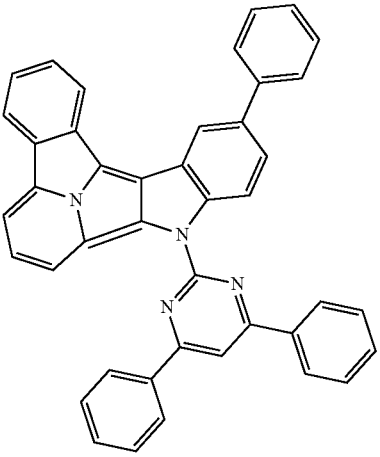 [SMILES: c1ccc(-c2ccc3c(c2)c2c(c4cccc5c6ccccc6c2n54)n3-c2nc(-c3ccccc3)cc(-c3ccccc3)n2)cc1] | 57% |

| | | |
|---|---|---|
| 4f | 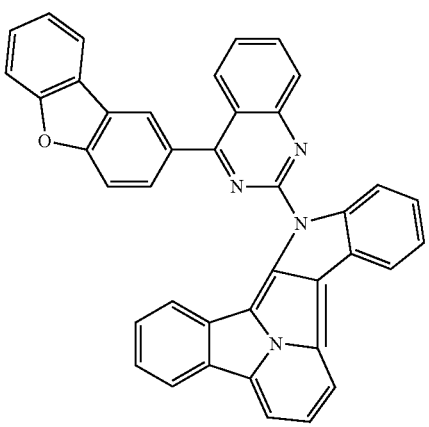 [SMILES: c1ccc2c(-c3ccc4oc5ccccc5c4c3)nc(-n3c4ccccc4c4c3c3c5ccccc5c5cccc4n53)nc2c1] | 61% |
| 5f | 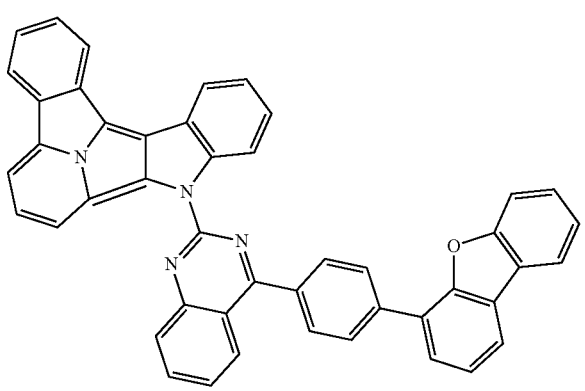 [SMILES: c1ccc2c(-c3ccc(-c4cccc5c4oc4ccccc45)cc3)nc(-n3c4ccccc4c4c3c3cccc5c6ccccc6c4n53)nc2c1] | 55% |
| 6f | 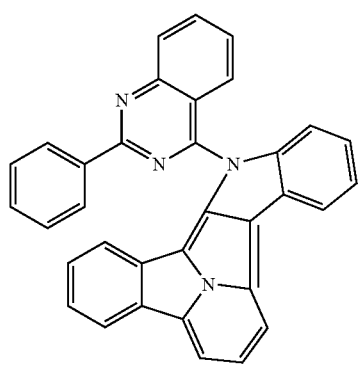 [SMILES: c1ccc(-c2nc(-n3c4ccccc4c4c3c3c5ccccc5c5cccc4n53)c3ccccc3n2)cc1] | 58% |
| 7f | 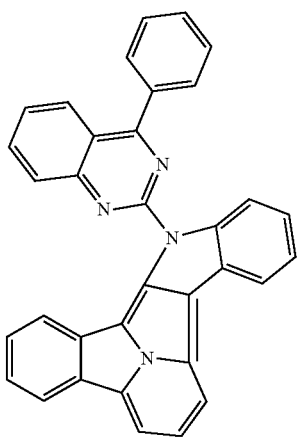 [SMILES: c1ccc(-c2nc(-n3c4ccccc4c4c3c3c5ccccc5c5cccc4n53)nc3ccccc23)cc1] | 54% |

| 8f | 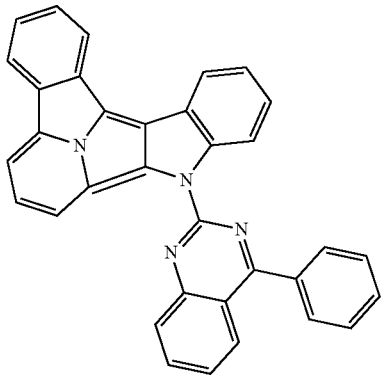 [SMILES: c1ccc(-c2nc(-n3c4ccccc4c4c3c3cccc5c6ccccc6c4n53)nc3ccccc23)cc1] | 62% |
|---|---|---|
| 9f | 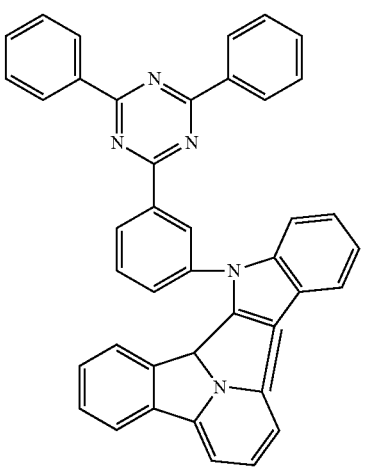 | 60% | g) Buchwald Coupling

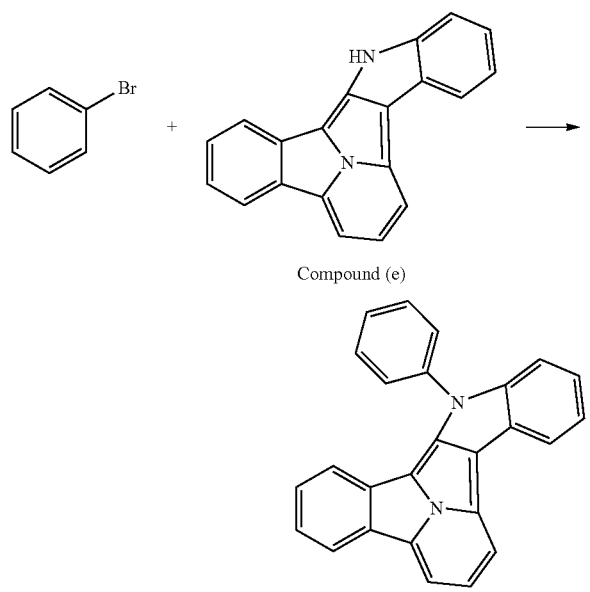

15.1 g (50 mmol) of compound (e) and 8.4 g (54 mmol) of bromobenzene are dissolved in 400 ml of toluene under an argon atmosphere. 1.0 g (5 mmol) of tri-tert-butylphosphine is added and the mixture is stirred under an argon atmosphere. 0.6 g (2 mmol) of Pd(OAc)$_2$ is added and the mixture is stirred under an argon atmosphere, and then 9.5 g (99 mmol) of sodium tert-butoxide are added. The reaction mixture is stirred under reflux for 24 h. After cooling, the organic phase is separated, washed three times with 200 ml of water, dried over MgSO$_4$ and filtered, and the solvent is removed under reduced pressure. The residue is purified by column chromatography using silica gel (eluent: DCM/heptane (1:3)). The residue is subjected to hot extraction with toluene, recrystallized from toluene/n-heptane and finally sublimed under high vacuum. The yield is 16.9 g (47 mmol), 88% of theory.

The following compounds can be prepared in an analogous manner:

| | Reactant 1 | Reactant 2 |
|---|---|---|
| 1g | | [1505512-86-6] |
| 2g | | 1153-85-1 |
| 3g | | [1225053-54-2] |
| 4g | | 212385-73-4 |
| 5g | | |
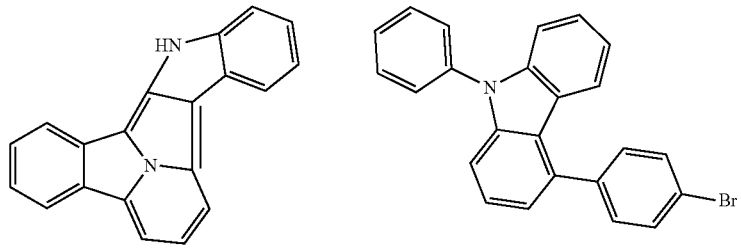
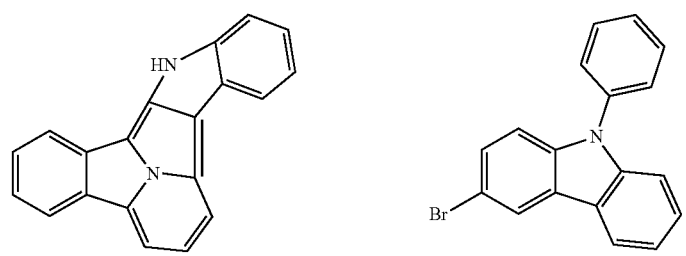
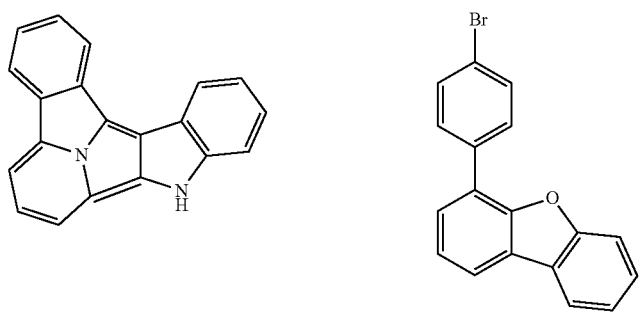
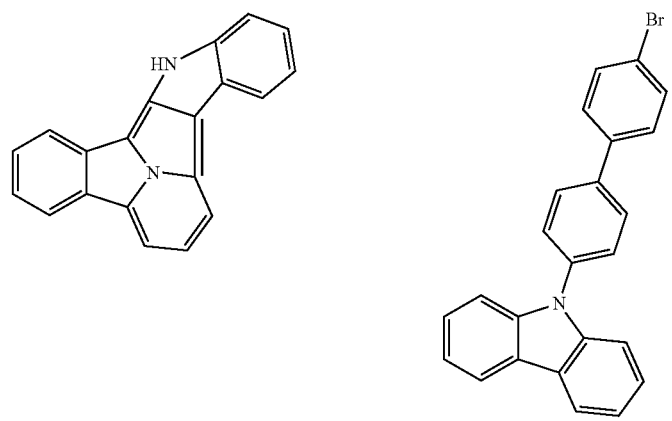
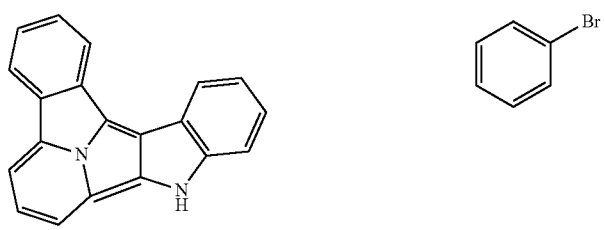

-continued
| | | |
|---|---|---|
| 6g | 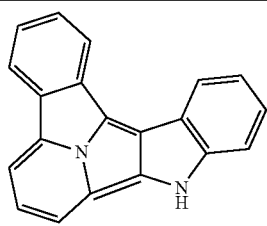 | 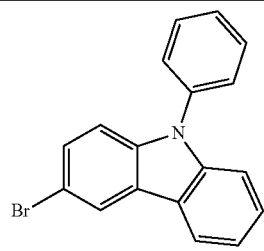 |
| 7g | 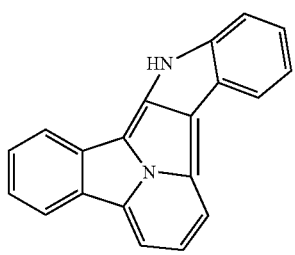 [SMILES: c1ccc2c(c1)[nH]c1c2c2cccc3c4ccccc4c1n32] | 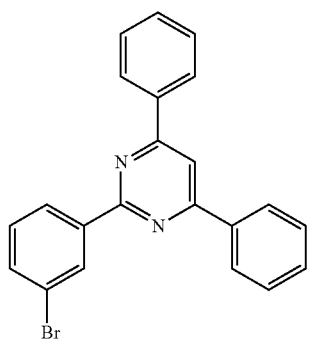<br>[864377-22-0] |
| | Product | Yield |
|---|---|---|
| 1g | 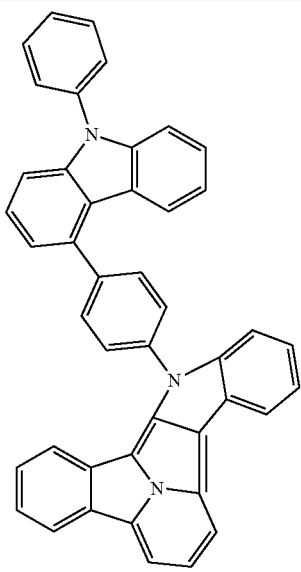 [SMILES: c1ccc(-n2c3ccccc3c3c(-c4ccc(-n5c6ccccc6c6c5c5c7ccccc7c7cccc6n75)cc4)cccc32)cc1] | 71% |
| 2g | 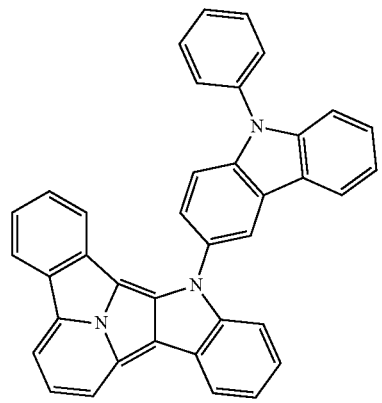 [SMILES: c1ccc(-n2c3ccccc3c3cc(-n4c5ccccc5c5c4c4c6ccccc6c6cccc5n64)ccc32)cc1] | 75% |

| | | |
|---|---|---|
| 3g | 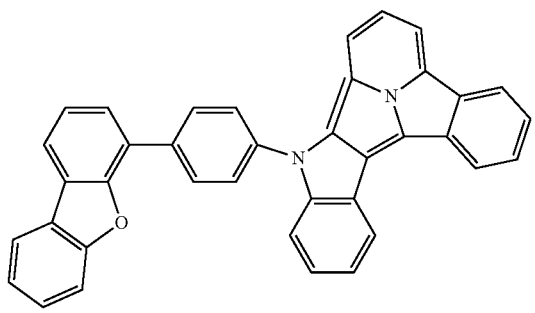 [SMILES: c1ccc2c(c1)oc1c(-c3ccc(-n4c5ccccc5c5c4c4cccc6c7ccccc7c5n64)cc3)cccc12] | 74% |
| 4g | 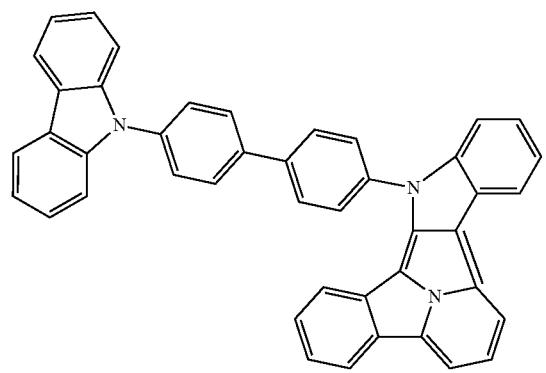 [SMILES: c1ccc2c(c1)c1ccccc1n2-c1ccc(-c2ccc(-n3c4ccccc4c4c3c3c5ccccc5c5cccc4n53)cc2)cc1] | 72% |
| 5g | 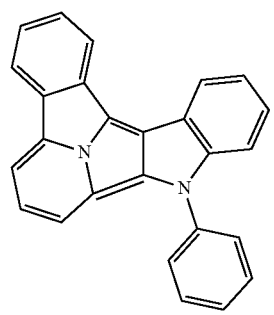 [SMILES: c1ccc(-n2c3ccccc3c3c2c2cccc4c5ccccc5c3n42)cc1] | 78% |

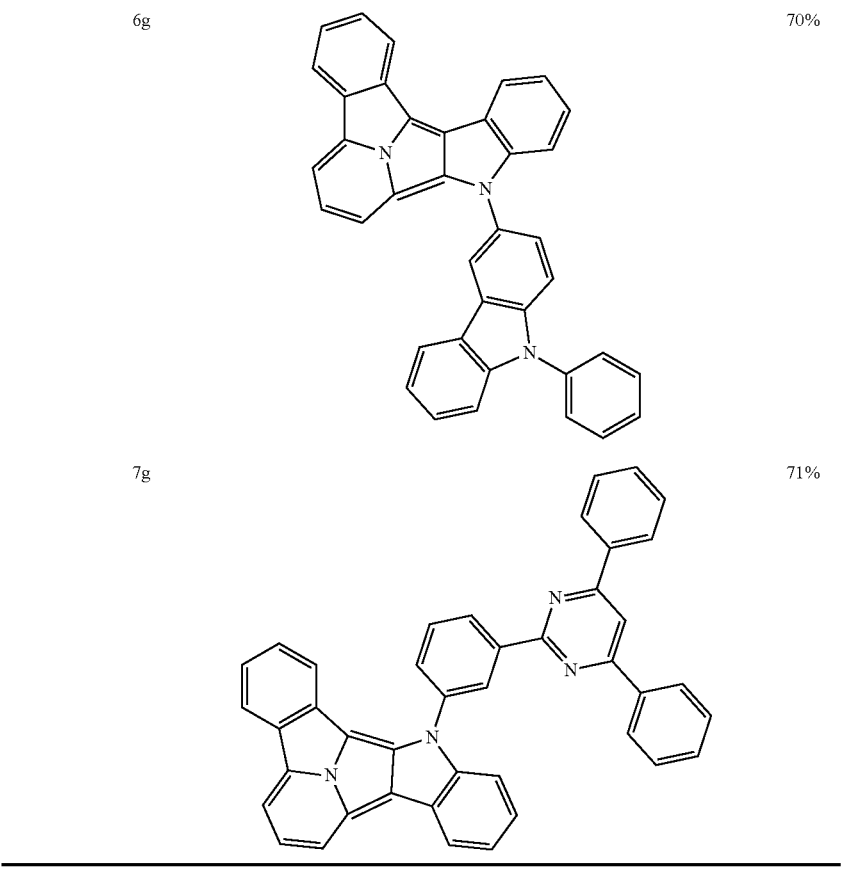

6g 70%

7g 71% h) Bromination

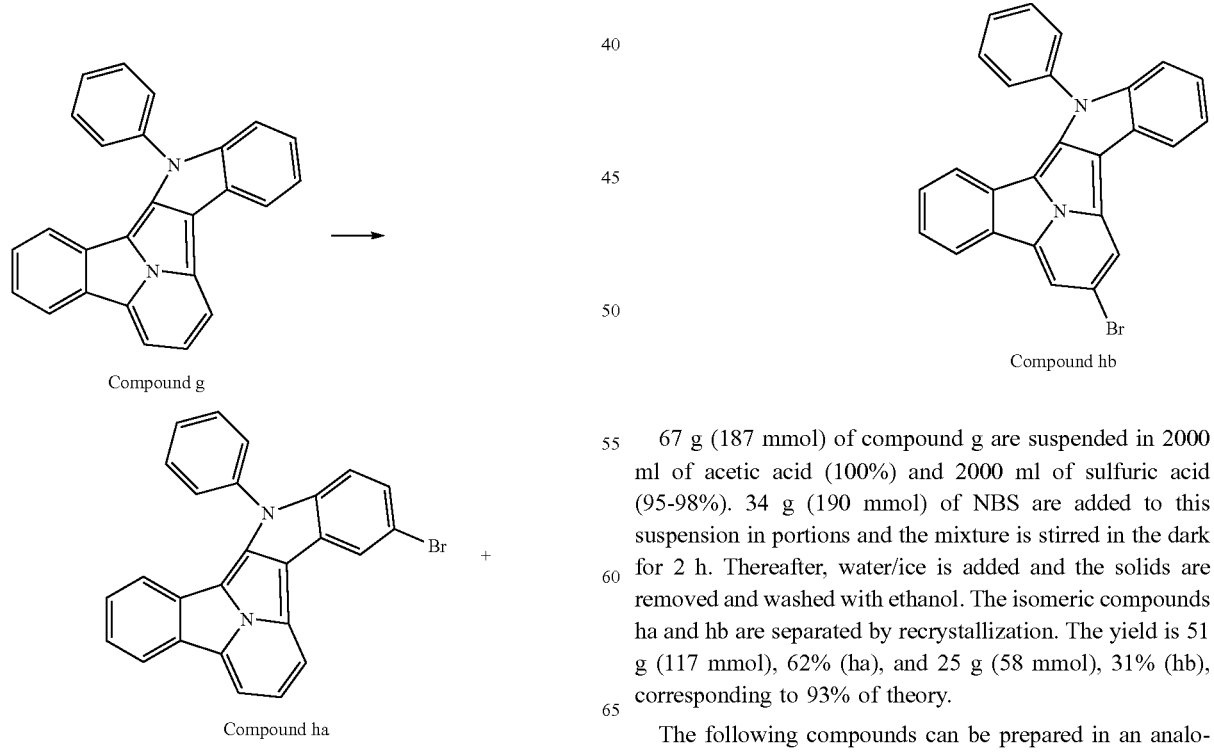

Compound g

Compound ha

Compound hb 67 g (187 mmol) of compound g are suspended in 2000 ml of acetic acid (100%) and 2000 ml of sulfuric acid (95-98%). 34 g (190 mmol) of NBS are added to this suspension in portions and the mixture is stirred in the dark for 2 h. Thereafter, water/ice is added and the solids are removed and washed with ethanol. The isomeric compounds ha and hb are separated by recrystallization. The yield is 51 g (117 mmol), 62% (ha), and 25 g (58 mmol), 31% (hb), corresponding to 93% of theory.

The following compounds can be prepared in an analogous manner:

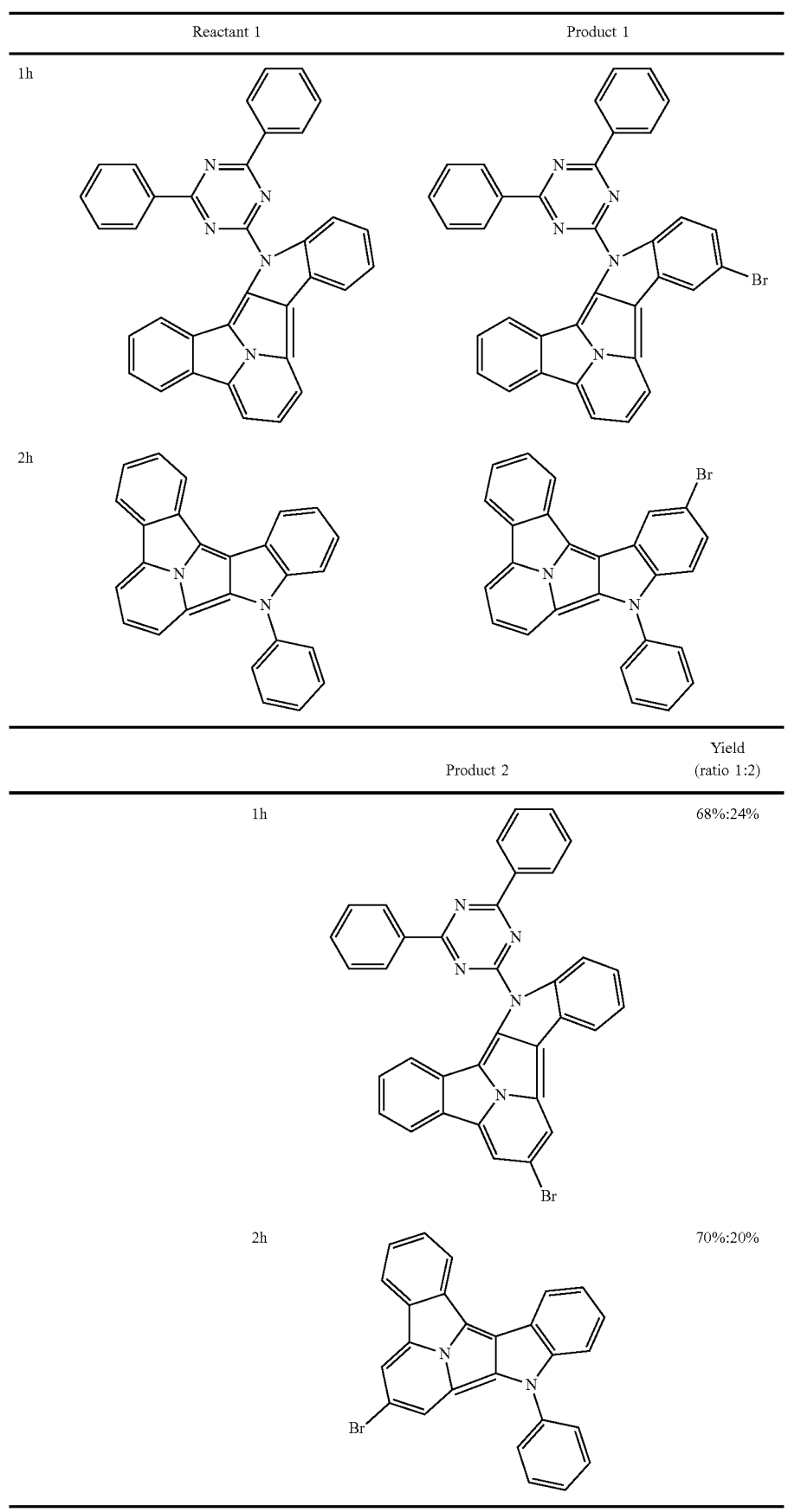

j) Suzuki Coupling

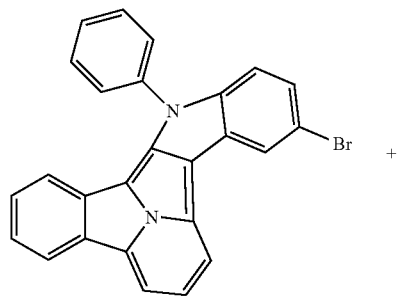

Compound (ha)

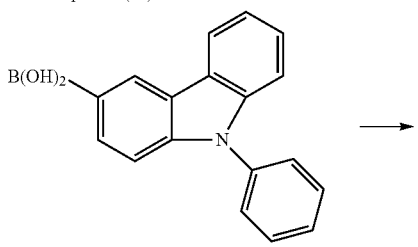

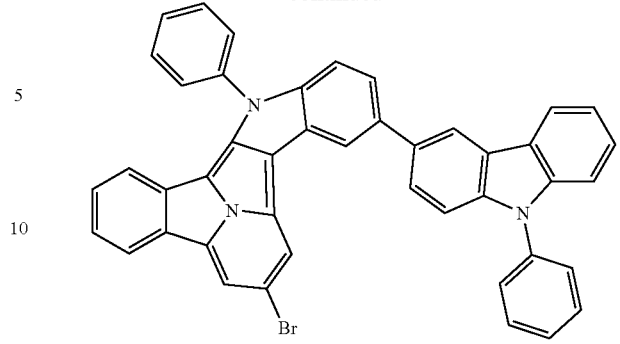

67 g (155 mmol) of compound (ha), 50 g (172 mmol) of N-phenylcarbazole-3-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The yield is 56 g (94 mmol), 61% of theory.

The following compounds can be prepared in an analogous manner:

| | Reactant 1 | Reactant 2 |
|---|---|---|
| 1j | 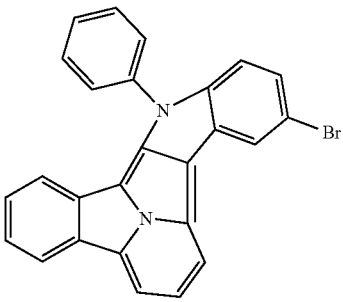 [SMILES: Brc1ccc2c(c1)c1c(c3c4ccccc4c4cccc1n43)n2-c1ccccc1] | 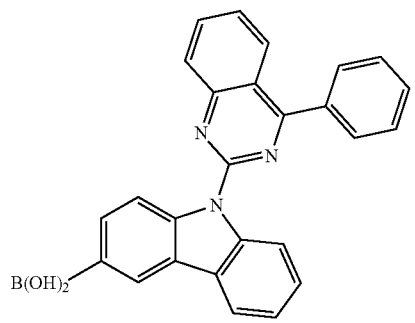 [1642121-58-1] |
| 2j | 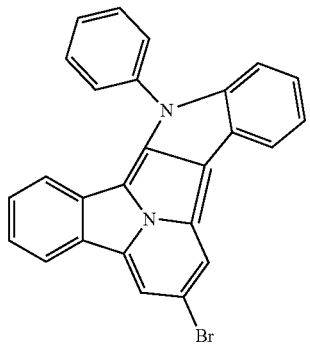 [SMILES: Brc1cc2c3ccccc3c3c4c(c5ccccc5n4-c4ccccc4)c(c1)n23] | 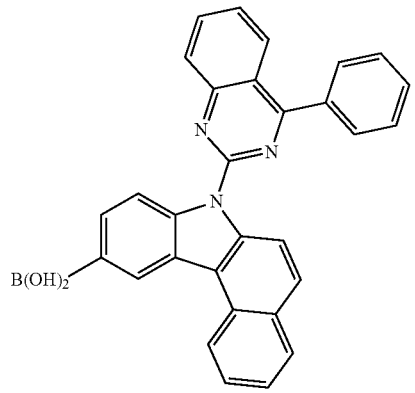 [1365548-86-2] |

3j 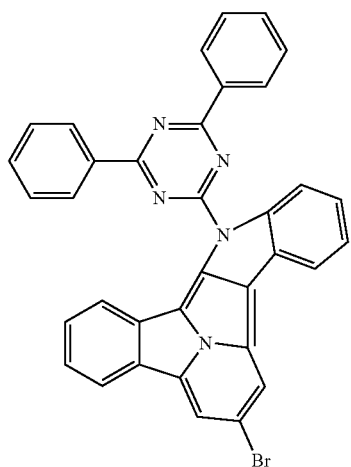 [SMILES: Brc1cc2c3ccccc3c3c4c(c5ccccc5n4-c4nc(-c5ccccc5)nc(-c5ccccc5)n4)c(c1)n23] 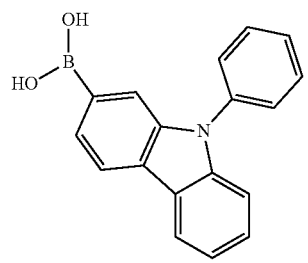
[1001911-63-2]
4j 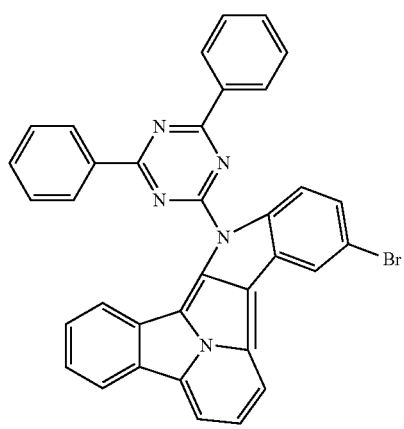 [SMILES: Brc1ccc2c(c1)c1c(c3c4ccccc4c4cccc1n43)n2-c1nc(-c2ccccc2)nc(-c2ccccc2)n1] 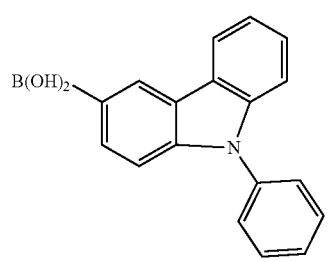 [SMILES: OB(O)c1ccc2c(c1)c1ccccc1n2-c1ccccc1]
5j 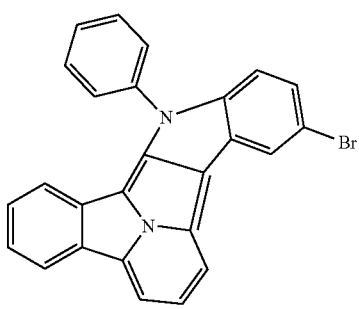 [SMILES: Brc1ccc2c(c1)c1c(c3c4ccccc4c4cccc1n43)n2-c1ccccc1] 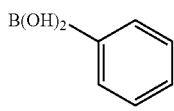
6j 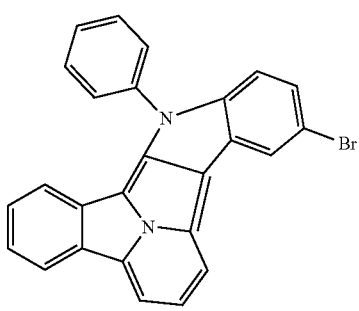 [SMILES: Brc1ccc2c(c1)c1c(c3c4ccccc4c4cccc1n43)n2-c1ccccc1] 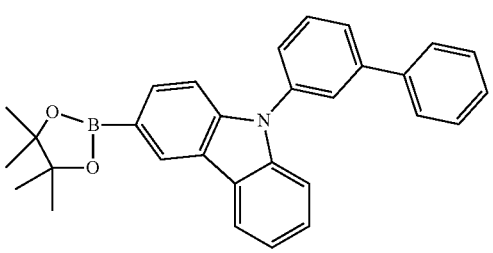
[1416814-68-0]

-continued
7j
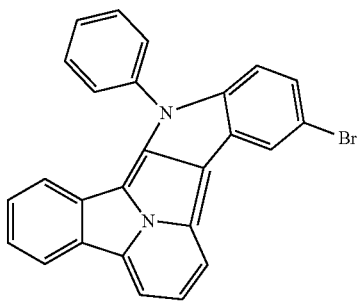 [SMILES: Brc1ccc2c(c1)c1c(c3c4ccccc4c4cccc1n43)n2-c1ccccc1]
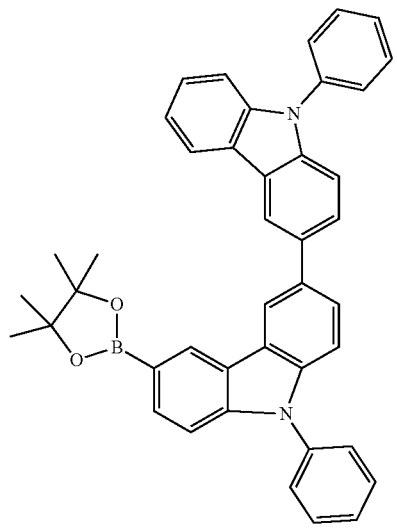
[1572537-61-1]
8j
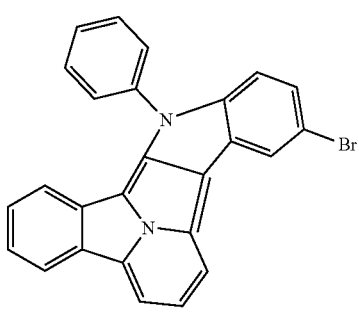 [SMILES: Brc1ccc2c(c1)c1c(c3c4ccccc4c4cccc1n43)n2-c1ccccc1]
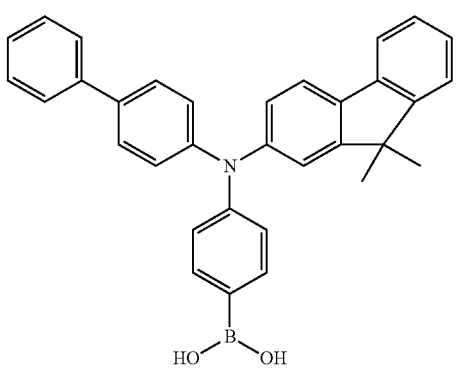
[1265177-27-2]
9j
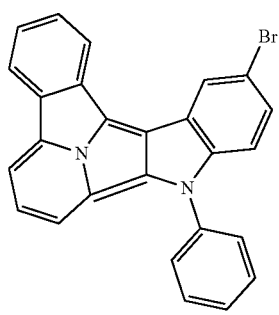 [SMILES: Brc1ccc2c(c1)c1c(c3cccc4c5ccccc5c1n43)n2-c1ccccc1]
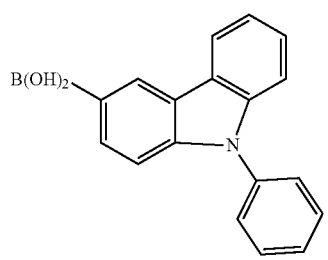 [SMILES: OB(O)c1ccc2c(c1)c1ccccc1n2-c1ccccc1]
10j
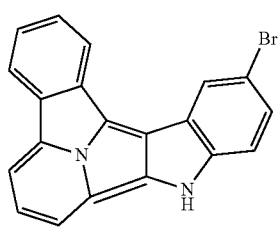 [SMILES: Brc1ccc2[nH]c3c(c2c1)c1c2ccccc2c2cccc3n21]
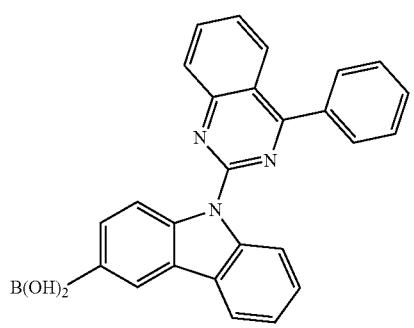
[1642121-58-1]

| | | |
|---|---|---|
| 11j | 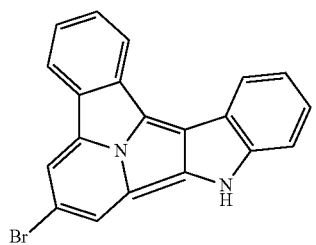 [SMILES: Brc1cc2c3ccccc3c3c4c5ccccc5[nH]c4c(c1)n23] | 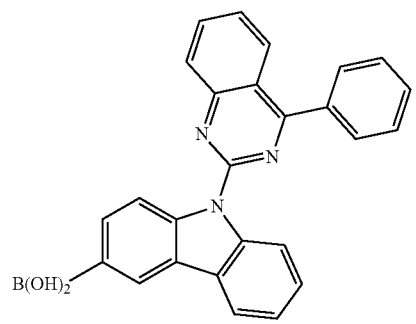<br>[1642121-58-1] |
| 12j | 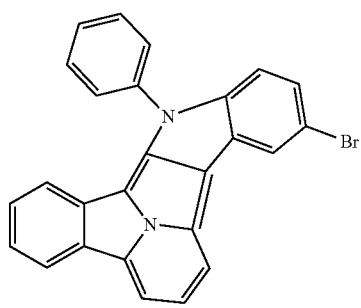 [SMILES: Brc1ccc2c(c1)c1c(c3c4ccccc4c4cccc1n43)n2-c1ccccc1] | 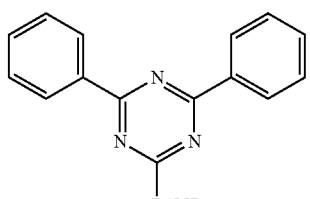<br>[1251825-65-6] |
| | Product | Yield |
|---|---|---|
| 1j | 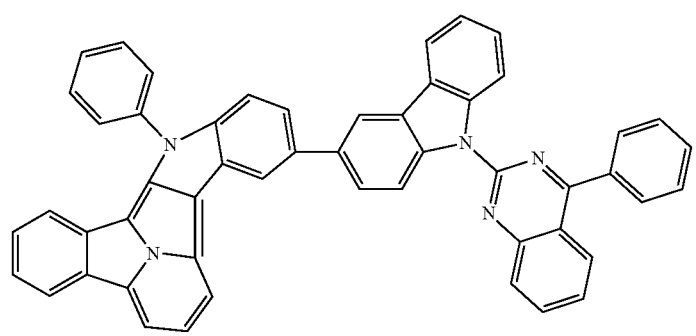 [SMILES: c1ccc(-c2nc(-n3c4ccccc4c4cc(-c5ccc6c(c5)c5c(c7c8ccccc8c8cccc5n87)n6-c5ccccc5)ccc43)nc3ccccc23)cc1] | 57% |

-continued
| 2j | 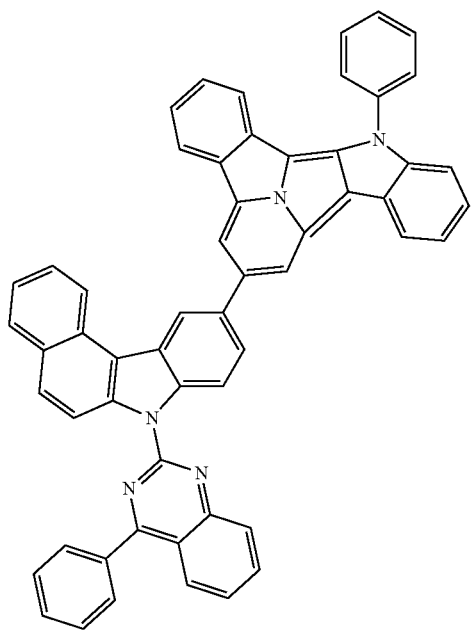 [SMILES: c1ccc(-c2nc(-n3c4ccc(-c5cc6c7ccccc7c7c8c(c9ccccc9n8-c8ccccc8)c(c5)n67)cc4c4c5ccccc5ccc43)nc3ccccc23)cc1] | 60% |
| 3j | 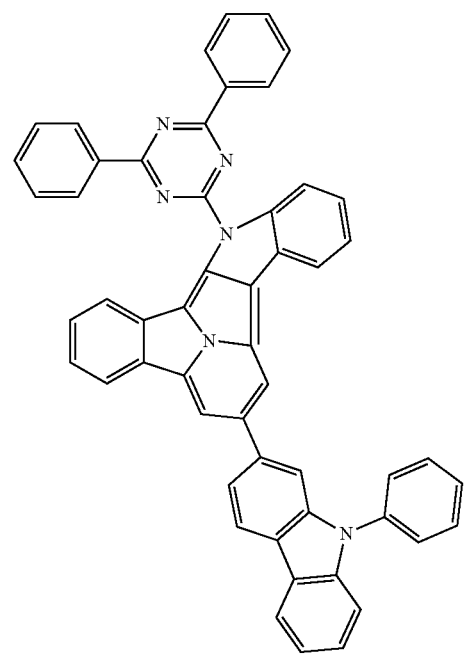 [SMILES: c1ccc(-c2nc(-c3ccccc3)nc(-n3c4ccccc4c4c3c3c5ccccc5c5cc(-c6ccc7c8ccccc8n(-c8ccccc8)c7c6)cc4n53)n2)cc1] | 64% |

| | | |
|---|---|---|
| 4j | 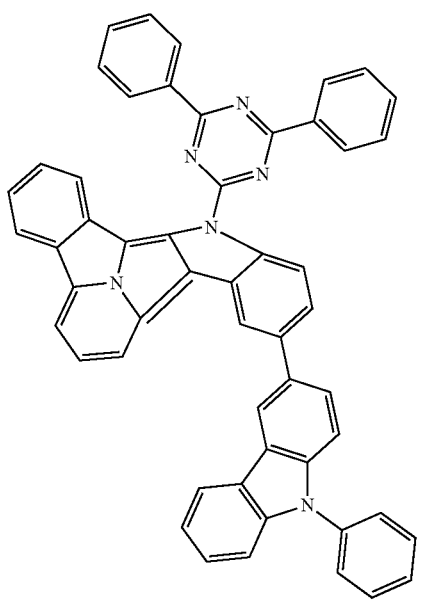 [SMILES: c1ccc(-c2nc(-c3ccccc3)nc(-n3c4ccc(-c5ccc6c(c5)c5ccccc5n6-c5ccccc5)cc4c4c3c3c5ccccc5c5cccc4n53)n2)cc1] | 59% |
| 5j | 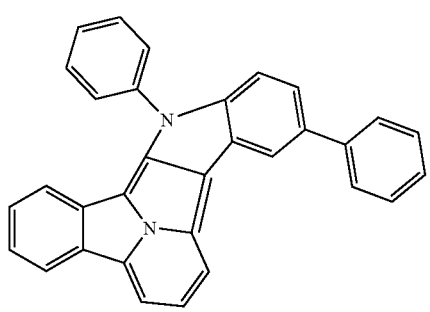 [SMILES: c1ccc(-c2ccc3c(c2)c2c(c4c5ccccc5c5cccc2n54)n3-c2ccccc2)cc1] | 79% |
| 6j | 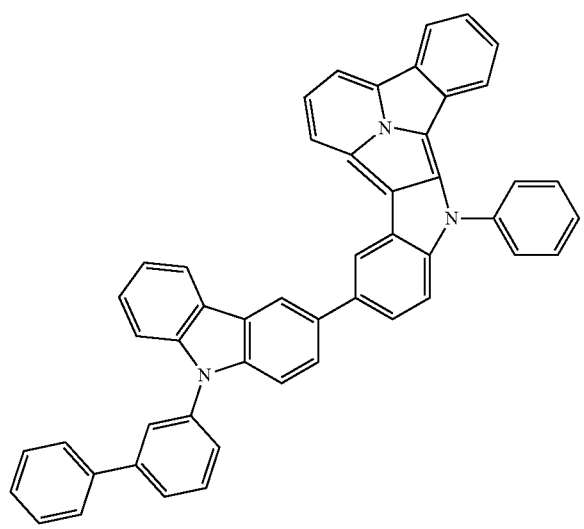 [SMILES: c1ccc(-c2cccc(-n3c4ccccc4c4cc(-c5ccc6c(c5)c5c(c7c8ccccc8c8cccc5n87)n6-c5ccccc5)ccc43)c2)cc1] | 56% |

| | | |
|---|---|---|
| 7j | 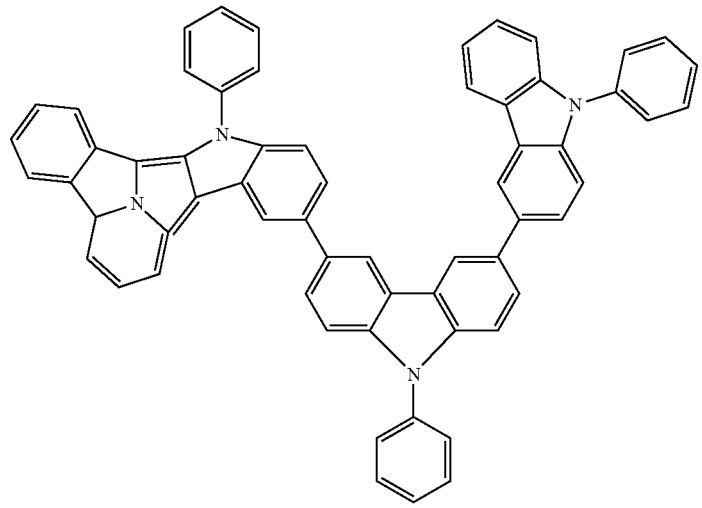 | 72% |
| 8j | 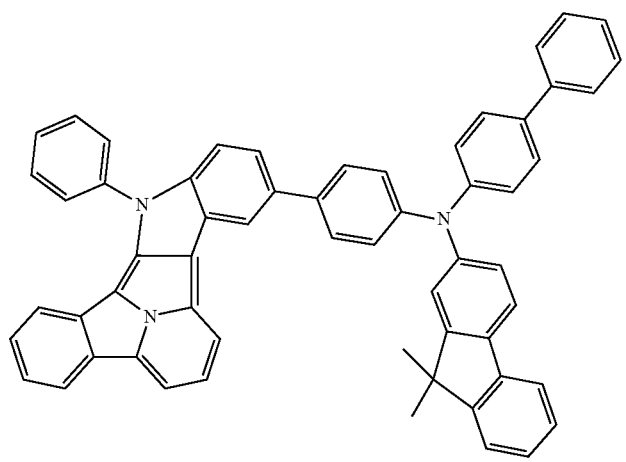 [SMILES: CC1(C)c2ccccc2-c2ccc(N(c3ccc(-c4ccccc4)cc3)c3ccc(-c4ccc5c(c4)c4c(c6c7ccccc7c7cccc4n76)n5-c4ccccc4)cc3)cc21] | 69% |
| 9j | 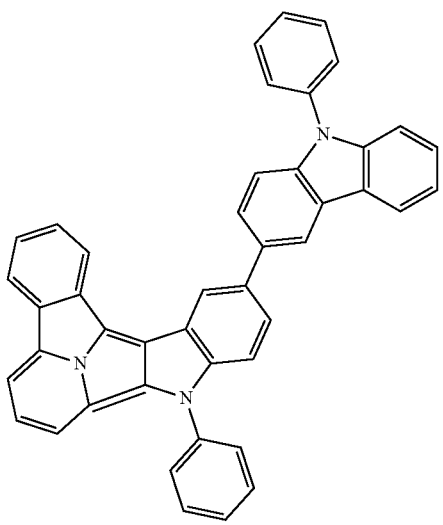 [SMILES: c1ccc(-n2c3ccccc3c3cc(-c4ccc5c(c4)c4c(c6cccc7c8ccccc8c4n76)n5-c4ccccc4)ccc32)cc1] | 65% |

-continued
10j 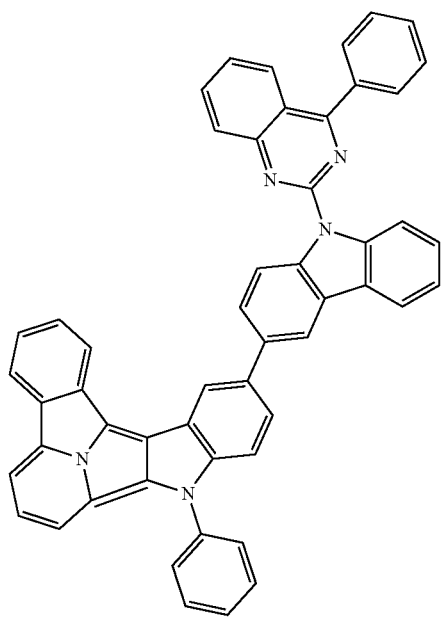 [SMILES: c1ccc(-c2nc(-n3c4ccccc4c4cc(-c5ccc6c(c5)c5c(c7cccc8c9ccccc9c5n87)n6-c5ccccc5)ccc43)nc3ccccc23)cc1] 61%
11j 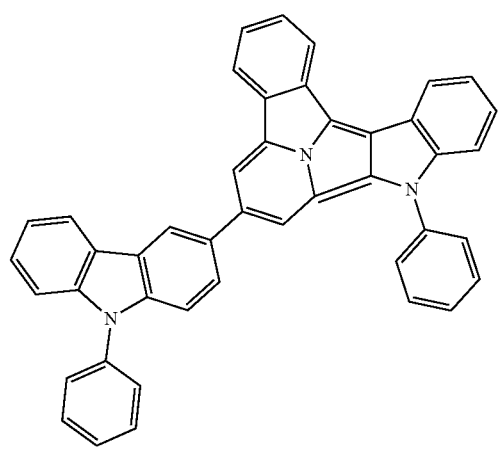 [SMILES: c1ccc(-n2c3ccccc3c3cc(-c4cc5c6ccccc6c6c7c8ccccc8n(-c8ccccc8)c7c(c4)n56)ccc32)cc1] 57%
12j 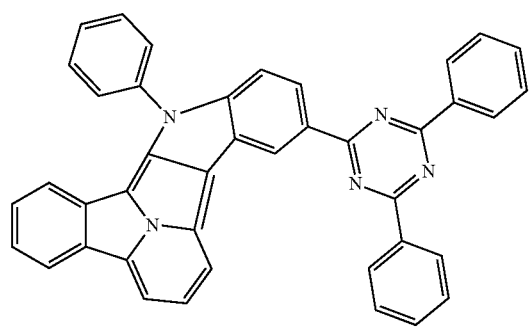 [SMILES: c1ccc(-c2nc(-c3ccccc3)nc(-c3ccc4c(c3)c3c(c5c6ccccc6c6cccc3n65)n4-c3ccccc3)n2)cc1] 61%

Production of the OLEDs

Examples 11 to 17 which follow (see Table 1) present the use of the materials of the invention in OLEDs.

Pretreatment for Examples 11 to 17: Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in Table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC2:TER1 (50%:45%:5%) mean here that the material IC1 is present in the layer in a proportion by volume of 50%, IC2 in a proportion by volume of 45% and TER1 in a proportion by volume of 5%. Analogously, the electron transport layer may also consist of a mixture of two materials. The OLEDs are characterized in a standard manner. The electroluminescence spectra are determined at a luminance of 1000 cd/m², and the CIE 1931 x and y color coordinates are calculated therefrom.

Use of Mixtures of the Invention in OLEDs

The materials of the invention can be used in the emission layer in phosphorescent red OLEDs. The inventive compounds 1f to 12j are used in Examples 11 to 17 as matrix material in the emission layer. The color coordinates of the electroluminescence spectra of the OLEDs are CIEx=0.67 and CIEy=0.33. These examples show that the materials of the invention are suitable for use in the emission layer of red OLEDs.

In addition, the materials of the invention can be used successfully in the electron blocker layer (EBL). This is shown in Example 15. Here too, the color coordinates of the spectrum of each of the OLEDs are CIEx=0.67 and CIEy=0.33.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| I1 | HATCN 5 nm | SpMA1 125 nm | SpMA2 10 nm | 1f:TER1 (95%:5%) 40 nm | — | ST1:LiQ (50%:50%) 35 nm | — |
| I2 | HATCN 5 nm | SpMA1 125 nm | SpMA2 10 nm | 7f:TER1 (95%:5%) 40 nm | — | ST1:LiQ (50%:50%) 35 nm | — |
| I3 | HATCN 5 nm | SpMA1 125 nm | SpMA2 10 nm | 7g:TER1 (95%:5%) 40 nm | — | ST1:LiQ (50%:50%) 35 nm | — |
| I4 | HATCN 5 nm | SpMA1 125 nm | SpMA2 10 nm | IC1:2g:TER1 (50%:45%:5%) 40 nm | — | ST1:LiQ (50%:50%) 35 nm | — |
| I5 | HATCN 5 nm | SpMA1 125 nm | 2 g 10 nm | IC1:2g:TER1 (50%:45%:5%) 40 nm | — | ST1:LiQ (50%:50%) 35 nm | — |
| I6 | HATCN 5 nm | SpMA1 125 nm | SpMA2 10 nm | 12j:TER1 (95%:5%) 40 nm | — | ST1:LiQ (50%:50%) 35 nm | — |
| I7 | HATCN 5 nm | SpMA1 125 nm | SpMA2 10 nm | IC2:12j:TER1 (50%:45%:5%) 40 nm | — | ST1:LiQ (50%:50%) 35 nm | — |

TABLE 2

Structural formulae of the materials for the OLEDs

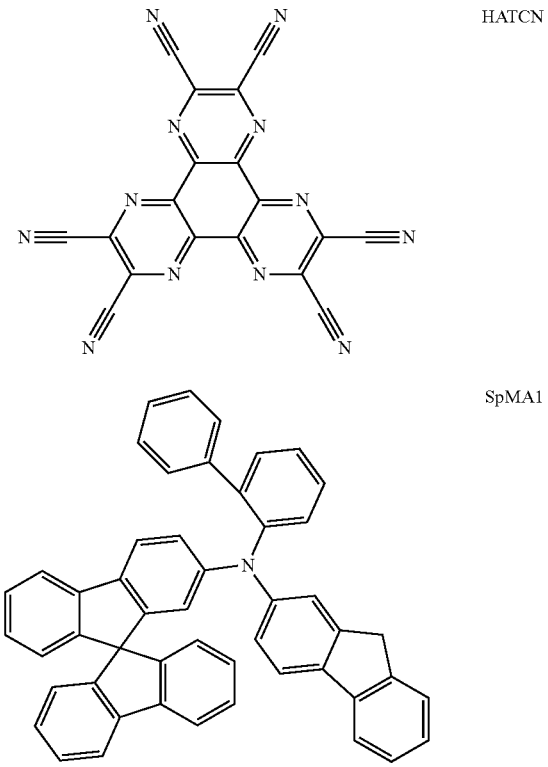

TABLE 2-continued
Structural formulae of the materials for the OLEDs
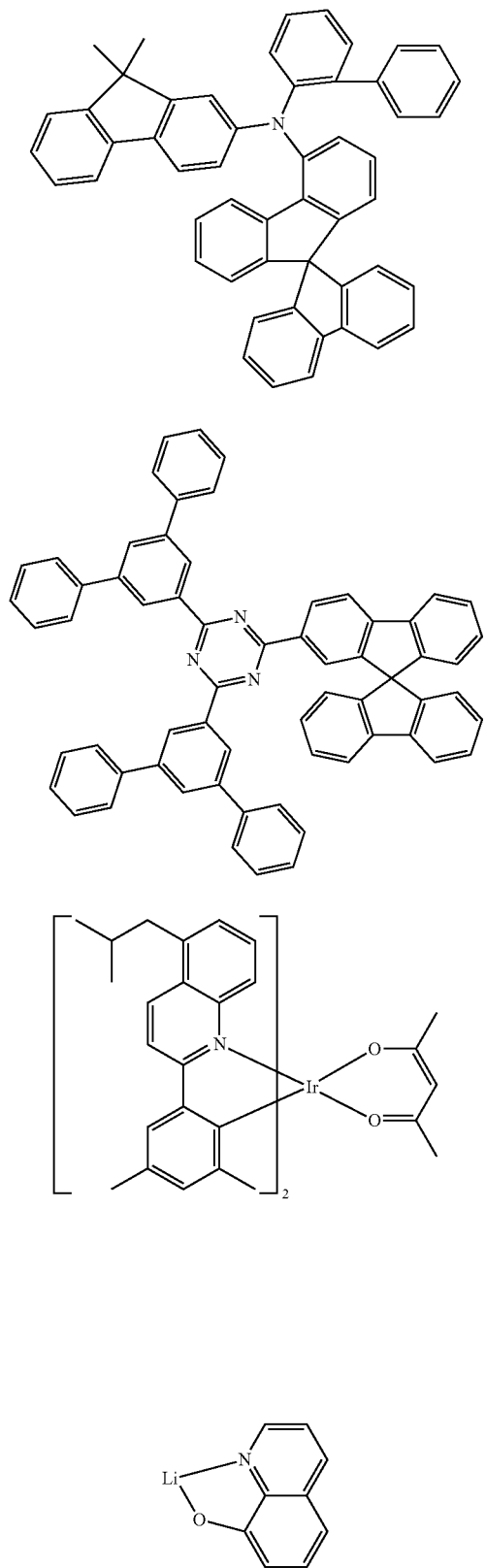

TABLE 2-continued

Structural formulae of the materials for the OLEDs

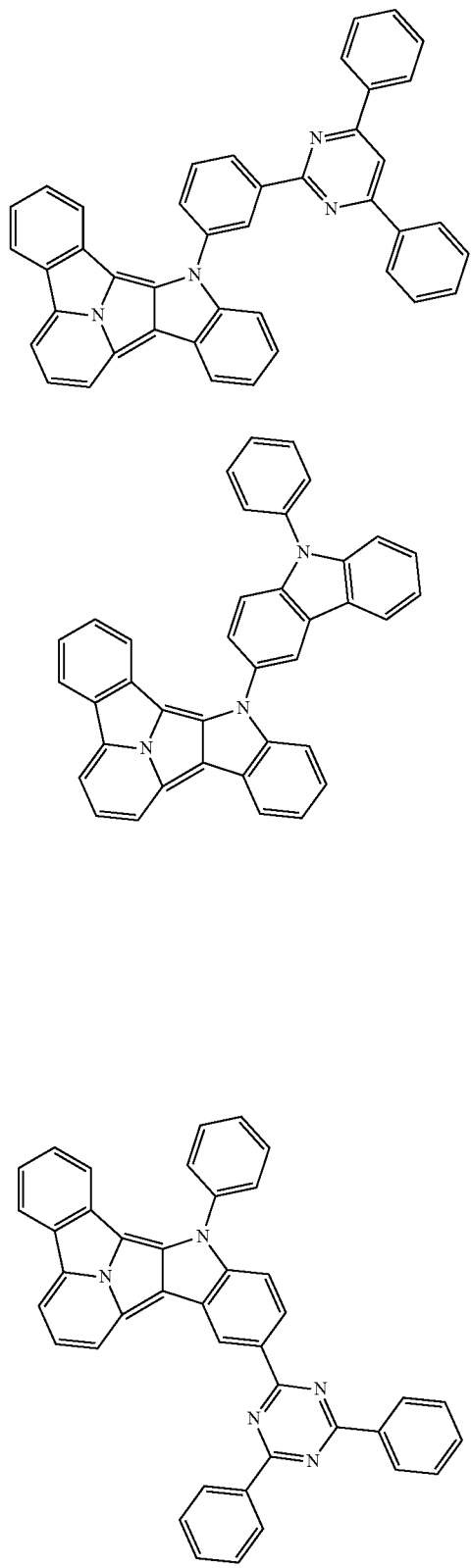

7g

2g

12j

The invention claimed is:
1. A compound comprising at least one structure of the formula (I)

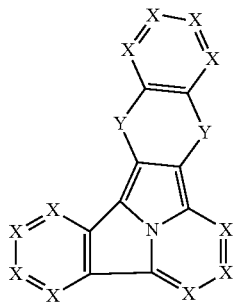

Formula (I)

where the symbols used are as follows:
Y is the same or different at each instance and is a bond or NR$^1$, NAr, O, S, C(R$^1$)$_2$, CArR$^1$, C(Ar)$_2$, Si(Ar)$_2$, SiArR$^1$ or Si(R$^1$)$_2$, where at least one Y group is selected from NR$^1$, NAr, O, S, C(R$^1$)$_2$, CArR$^1$, C(Ar)$_2$, Si(Ar)$_2$, SiArR$^1$ or Si(R$^1$)$_2$;
X is the same or different at each instance and is N or CR$^1$,
Ar is the same or different at each instance and is an aromatic or heteroaromatic ring system which has 5 to 60 aromatic ring atoms and may be substituted by one or more R$^1$ radicals; at the same time, two Ar radicals bonded to the same carbon atom or silicon atom may also be joined to one another by a single bond or a bridge selected from B(R$^1$), C(R$^1$)$_2$, Si(R$^1$)$_2$, C=O, C=NR$^1$, C=C(R$^1$)$_2$, O, S, S=O, SO$_2$, N(R$^1$), P(R$^1$) and P(=O)R$^1$;
R$^1$ is the same or different at each instance and is H, D, OH, OR$^2$, F, Cl, Br, I, CN, NO$_2$, N(Ar$^1$)$_2$, N(R$^2$)$_2$, C(=O)Ar$^1$, C(=O)R$^2$, P(=O)(Ar$^1$)$_2$, P(Ar$^1$)$_2$, B(Ar$^1$)$_2$, B(OR$^2$)$_2$, Si(Ar$^1$)$_3$, Si(R$^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a combination of these systems, at the same time, two or more radicals may form a ring system with one another;
Ar$^1$ is the same or different at each instance and is an aromatic or heteroaromatic ring system which has 5 to 30 aromatic ring atoms and may be substituted by one or more nonaromatic R$^2$ radicals; at the same time, it is possible for two Ar$^1$ radicals bonded to the same silicon atom, nitrogen atom, phosphorus atom or boron atom also to be joined to one another by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is the same or different at each instance and is H, D, F, Cl, Br, I, CN, B(OR$^3$)$_2$, NO$_2$, C(=O)R$^3$, CR$^3$=C(R$^3$)$_2$, C(=O)OR$^3$, C(=O)N(R$^3$)$_2$, Si(R$^3$)$_3$, P(R$^3$)$_2$, B(R$^3$)$_2$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^1$)$_2$, Ge(R$^3$)$_2$, Sn(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more substituents may also form a ring system with one another;

R$^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, it is also possible for two or more substituents to form a ring system with one another.

2. The compound as claimed in claim 1, comprising at least one structure of the formula (IIa) or (IIb)

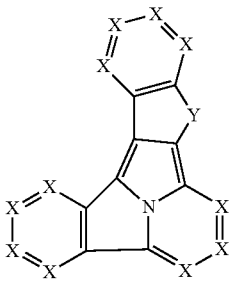

Formula (IIa)

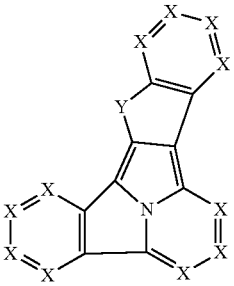

Formula (IIb)

where the symbols Y and X used have the definition given in claim 1.

3. The compound as claimed in claim 1, comprising at least one structure of the formula (IIIa), (IIIb), (IVa), (IVb), (Va) or (Vb)

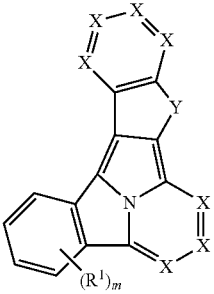

Formula (IIIa)

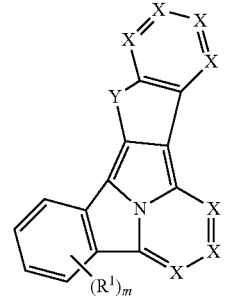

Formula (IIIb)

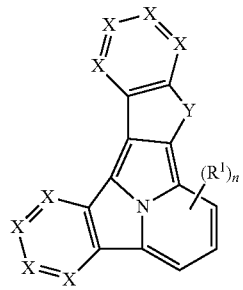

Formula (IVa)

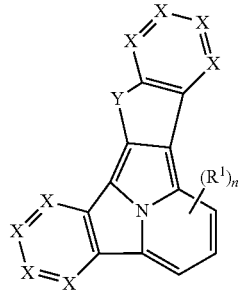

Formula (IVb)

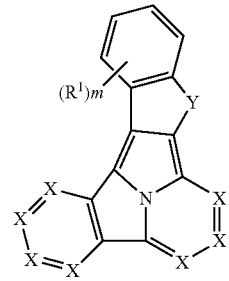

Formula (Va)

-continued

Formula (Vb)

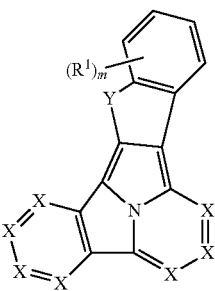

where the symbols $R^1$, Y and X have the definition given in claim 1, in is 0, 1, 2, 3 or 4, and n is, 0, 1, 2 or 3.

4. The compound as claimed in claim 1, comprising at least one structure of the formula (VIa) or (VIb)

Formula (VIa)

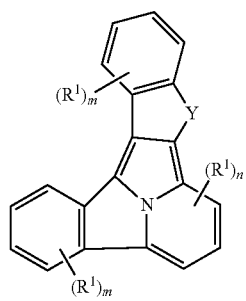

Formula (VIb)

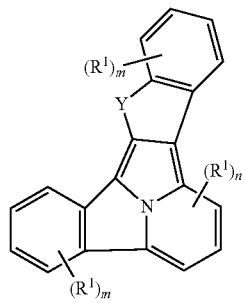

where the symbols $R^1$ and Y have the definition given in claim 1, m is the same or different at each instance and is 0, 1, 2, 3 or 4, and n is 0, 1, 2 or 3.

5. The compound as claimed in claim 1, characterized in that the compound comprises a hole transport group.

6. The compound as claimed in claim 5, characterized in that the hole transport group comprises a group selected from the formulae (H-1) to (H-3)

Formula (H-1)

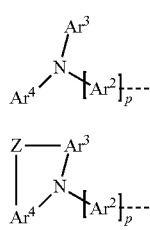

Formula (H-2)

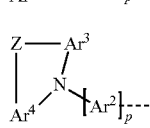

-continued

Formula (H-3)

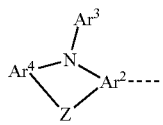

where the dotted bond marks the position of attachment and in addition:

$Ar^2$, $Ar^3$, $Ar^4$ is in each case independently an aromatic ring system having 6 to 40 carbon atoms or a heteroaromatic ring system having 3 to 40 carbon atoms, each of which may be substituted by one or more $R^1$ radicals, p is 0 or 1, Z is $C(R^1)_2$, $Si(R^1)_2$, C=O, N—$Ar^1$, $BR^1$, $PR^1$, $POR^1$, SO, $SOL$, Se, O or S, where the symbols $Ar^1$ and $R^1$ have the definition given in claim 1, where the presence of an N—N bond is ruled out, such that, in the case that Y=NAr, the index p=1.

7. The compound as claimed in claim 5, characterized in that the hole transport group comprises a group selected from the formulae (H-4) to (H-26)

Formula (H-4)

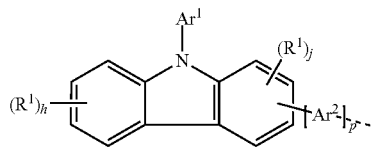

Formula (H-5)

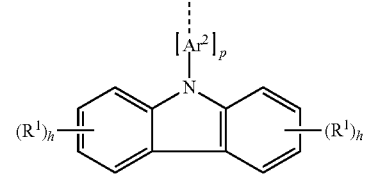

Formula (H-6)

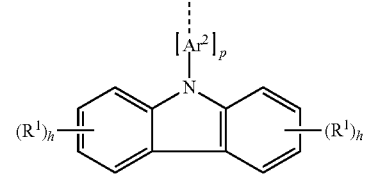

Formula (H-7)

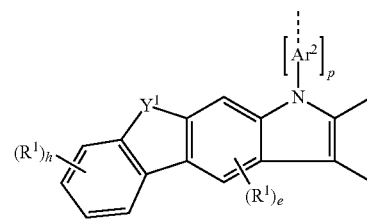

Formula (H-8)

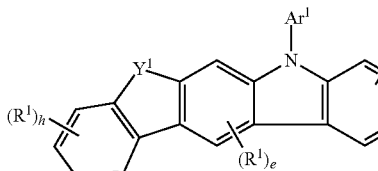

Formula (H-9)
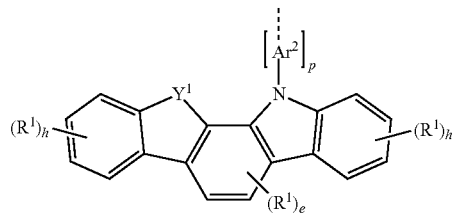
Formula (H-10)
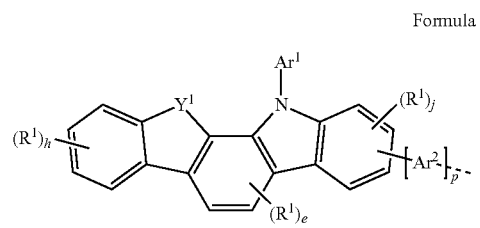
Formula (H-11)
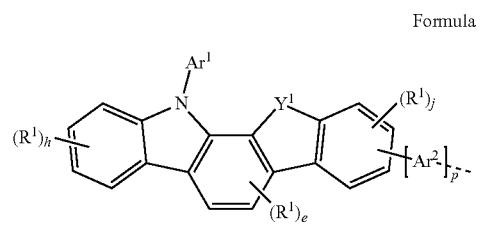
Formula (H-12)
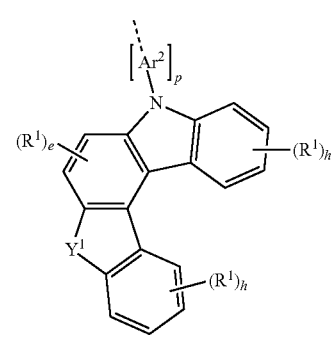
Formula (H-13)
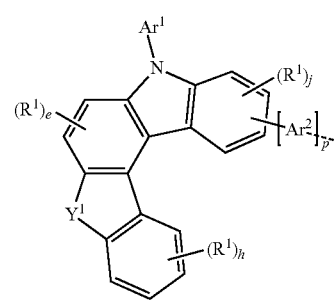
Formula (H-14)
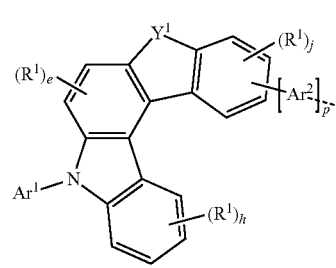
Formula (H-15)
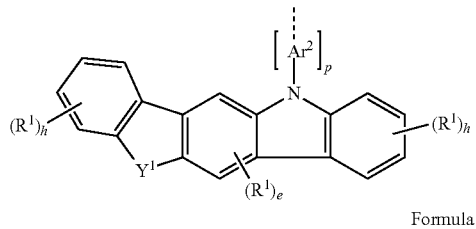
Formula (H-16)
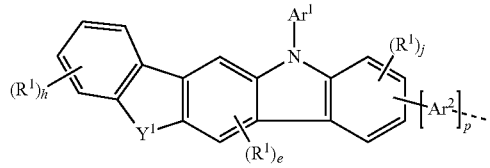
Formula (H-17)
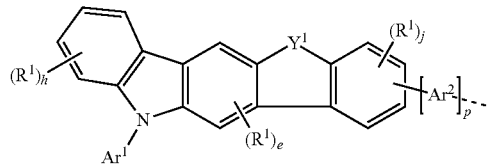
Formula (H-18)
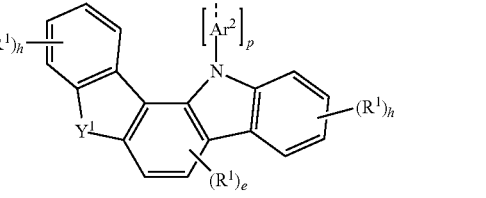
Formula (H-19)
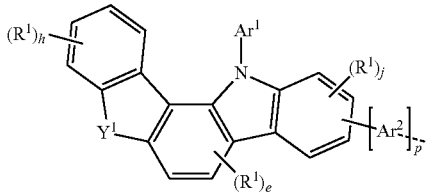
Formula (H-20)
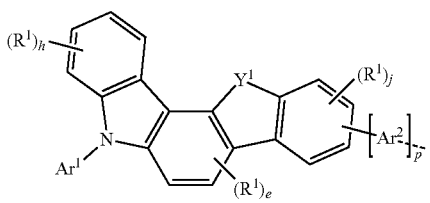
Formula (H-21)
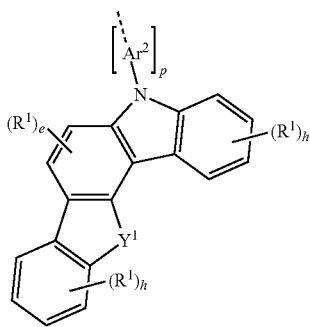

-continued

Formula (H-22)

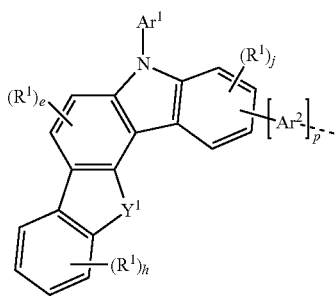

Formula (H-23)

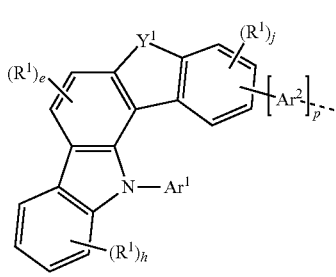

Formula (H-24)

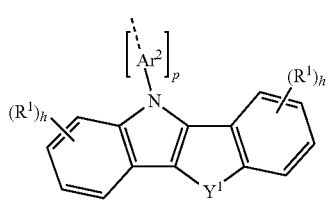

Formula (H-25)

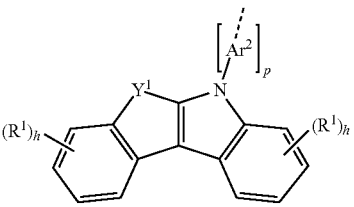

Formula (H-26)

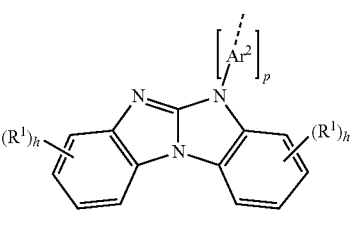

where $Y^1$ represents O, S, $C(R^1)_2$ or $NAr^1$, the dotted bond marks the position of attachment, e is 0, 1 or 2, j is 0, 1, 2 or 3, h is 0, 1, 2, 3 or 4, p is 0 or 1, $R^1$ is the same or different at each instance and is H, D, OH, $OR^2$, F, CL, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems, at the same time, two or more radicals may form a ring system with one another;

$Ar^1$ is the same or different at each instance and is an aromatic or heteroaromatic ring system which has 5 to 30 aromatic ring atoms and may be substituted by one or more nonaromatic $R^2$ radicals; at the same time, it is possible for two $Ar^1$ radicals bonded to the same silicon atom, nitrogen atom, phosphorus atom or boron atom also to be joined to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems, at the same time two or more substituents may also form a ring system with one another;

$R^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, it is also possible for two or more substituents to form a ring system with one another, and $Ar^2$ is in each case independently an aromatic ring system having 6 to 40 carbon atoms or a heteroaromatic ring system having 3 to 40 carbon atoms, each of which may be substituted by one or more $R^1$ radicals:

where the presence of an N—N bond is ruled out, such that, in the case that Y=NAr in the formulae (H-5), (H-6), (H-9), (H-12), (H-15), (H-18), (H-21), (H-24), (H-25) and (H-26), the index p=1.

8. The compound as claimed in claim 1, characterized in that the compound comprises an electron transport group.

9. A compound as claimed in claim 8, characterized in that the Ar group present in a Y group, or an $R^1$ group bonded to the base skeleton, is a group representable by the formula (QL)

Formula (QL)

in which $L^1$ represents a bond or an aromatic or heteroaromatic ring system which has 5 to 40 aromatic ring atoms and may be substituted by one or more $R^1$ radicals, and Q is an electron transport group, where
$R^1$ is the same or different at each instance and is H, D, OH, $OR^2$, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, two or more radicals may form a ring system with one another;
$Ar^1$ is the same or different at each instance and is an aromatic or heteroaromatic ring system which has 5 to 30 aromatic ring atoms and may be substituted by one or more nonaromatic $R^2$ radicals; at the same time, it is possible for two $Ar^1$ radicals bonded to the same silicon atom, nitrogen atom, phosphorus atom or boron atom also to be joined to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$,
$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ group may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems, at the same time, two or more substituents may also form a ring system with one another;

$R^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, it is also possible for two or more substituents to form a ring system with one another.

10. The compound as claimed in claim 9, characterized in that the electron transport group is selected from structures of the formulae (Q-1), (Q-2), (Q-3), (Q-4), (Q-5), (Q-6), (Q-7), (Q-8), (Q-9) and/or (Q-10)

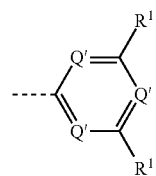
Formula (Q-1)

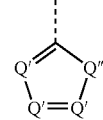
Formula (Q-2)

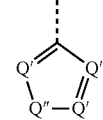
Formula (Q-3)

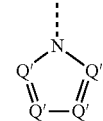
Formula (Q-4)

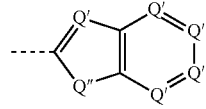
Formula (Q-5)

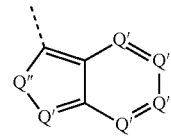
Formula (Q-6)

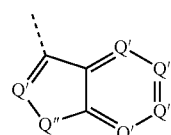
Formula (Q-7)

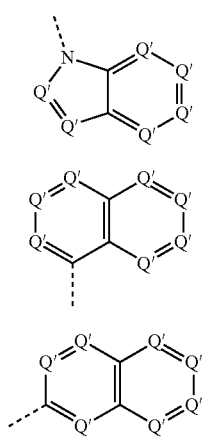

Formula (Q-8)

Formula (Q-9)

Formula (Q-10)

where the dotted bond marks the position of attachment,
Q' is the same or different at each instance and is $CR^1$ or N, where at least one Q' is N;
Q" is $NR^1$, O or S, and
$R^1$ is as defined in claim 9.

11. An oligomer, polymer or dendrimer containing one or more compounds as claimed in claim 1, wherein, rather than a hydrogen atom or a substituent, there are one or more bonds of the compounds to the polymer, oligomer or dendrimer.

12. A composition comprising at least one compound as claimed in claim 1 and at least one further compound selected from the group consisting of fluorescent emitters, phosphorescent emitters, matrix materials, electron transport materials, electron injection materials, hole conductor materials, hole injection materials, electron blocker materials and hole blocker materials.

13. A formulation comprising at least one compound as claimed in claim 1 and at least one solvent.

14. A process for preparing the compound as claimed in claim 1, characterized in that, in a coupling reaction, a compound comprising at least one nitrogen-containing heterocyclic group is joined to a compound comprising at least one aromatic or heteroaromatic group.

15. An electronic device comprising at least one compound as claimed in claim 1.

16. The electronic device as claimed in claim 15 which is an organic electroluminescent device, characterized in that the compound is present as matrix material in an emitting layer, as hole transport material or as electron transport material.

17. The compound as claimed in claim 1, wherein
Y is the same or different at each instance and is $NR^1$ or NAr;
$R^1$ is the same or different at each instance and is H, D, OH, $OR^2$, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(OR^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, two or more adjacent $R^1$ radicals may form a ring system with one another;

$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also form a ring system with one another and $R^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, it is also possible for two or more adjacent $R^3$ substituents to form a ring system with one another.

18. The compound as claimed in claim 1, characterized in that the compound comprises a hole transport group, and the Ar group present in the Y group, or an $R^1$ group bonded to the base skeleton comprises and represents the hole transport group.

19. The compound as claimed in claim 1, characterized in that the Ar group present in a Y group comprises and represents an electron transport group.

* * * * *